(12) United States Patent
Pressato et al.

(10) Patent No.: US 6,723,709 B1
(45) Date of Patent: Apr. 20, 2004

(54) BIOMATERIALS FOR PREVENTING POST-SURGICAL ADHESIONS COMPRISED OF HYALURONIC ACID DERIVATIVES

(75) Inventors: Daniele Pressato, Montegrotto Terme (IT); Alessandra Pavesio, Padova (IT); Lanfranco Callegaro, Vicenza (IT)

(73) Assignee: Fidia Advanced Biopolymers, S.r.l., Brindisi (IT)

( * ) Notice: Subject to any disclaimer, the term of this patent is extended or adjusted under 35 U.S.C. 154(b) by 0 days.

(21) Appl. No.: 09/031,835

(22) Filed: Feb. 27, 1998

Related U.S. Application Data

(63) Continuation-in-part of application No. PCT/EP96/03805, filed on Aug. 29, 1996.

(51) Int. Cl.[7] ........................ A61K 31/728; A61K 9/70; C08B 37/08
(52) U.S. Cl. .................... 514/54; 514/56; 514/62; 536/53; 536/55; 536/55.2; 424/423; 424/443; 424/488
(58) Field of Search .................... 514/56, 62, 54; 536/18.7, 53, 55, 55.2; 424/423, 443, 488

(56) References Cited

U.S. PATENT DOCUMENTS

| 5,326,356 A | * | 7/1994 | Della Valle et al. ......... 623/15 |
| 5,399,351 A | * | 3/1995 | Leshchiner et al. ......... 424/422 |
| 5,520,916 A | * | 5/1996 | Dorigatti et al. ............ 424/402 |
| 5,658,582 A | * | 8/1997 | Dorigatti et al. ............ 424/402 |
| 5,824,335 A | * | 10/1998 | Dorigatti et al. ............ 424/443 |

FOREIGN PATENT DOCUMENTS

| EP | 0216453 A2 | 4/1987 |
| EP | 0341745 A1 | 11/1989 |
| EP | 9213579 A1 | 8/1992 |
| WO | 8600912 A1 | 2/1986 |
| WO | 9311805 A1 | 6/1993 |
| WO | 9403212 A1 | 2/1994 |
| WO | WO 94/17837 | * 8/1994 |

* cited by examiner

*Primary Examiner*—James O. Wilson
*Assistant Examiner*—Leigh C. Maier
(74) *Attorney, Agent, or Firm*—Birch, Stewart, Kolasch & Birch, LLP

(57) ABSTRACT

New biomaterials essentially constituted by esterified derivatives of hyaluronic acid or by cross-linked derivatives of hyaluronic acid for use in the surgical sector, particularly for use in the prevention of post-surgical adhesion.

15 Claims, 26 Drawing Sheets

BIOMATERIALS FOR PREVENTING POST-SURGICAL ADHESIONS COMPRISED OF HYALURONIC ACID DERIVATIVES

This application is a continuation-in-part of PCT international application No. PCT/EP96/03805 which has an international filing date of Aug. 29, 1996 which designated the United States, the entire contents of which are hereby incorporated by reference.

OBJECT OF THE INVENTION

The present invention concerns new biomaterials essentially constituted by esterified derivatives of hyaluronic acid or by cross-linked derivatives of hyaluronic acid for use in the surgical sector, particularly for use in the prevention of post-surgical adhesions.

FIELD OF THE INVENTION

Postoperative adhesion formation is a common complication in abdominal or pelvic surgery which may lead to a substantial morbidity. Many factors may influence the development of adhesions: mechanical trauma, chemical agents, drying of serosa in combination with blood, ischemia, infection and foreign material are all known to increase adhesion formation. Other causes are intraabdominal inflammatory diseases and congenital abnormalities. The pathophysiological mechanism still remain unclear, but a central common pathway in which peritoneal fibrinolysis plays an important role has been suggested.

The surgical trauma of the tissue causes the release of a serosanguinous exudate which forms a fibrinous bridge that persists several days during which cell growth occurs. If the exudate is not absorbed or lysed within this period, it becomes ingrown with fibroblasts and subsequent collagen deposition leads to the formation of a permanent scar connecting the two adjacent surfaces, called an adhesion. Thus, adhesion formation seems to be a result of an inflammatory response.

In this latter case, the research has mainly focused on the search for bioabsorbable materials with a short time of in vivo persistence, to act as barriers to adhesion formation until healing has occurred; in order to obviate the problems caused by non-absorbable materials (infection, calcification of the implants, scar formation, etc.).

One particularly promising polymer is Hyaluronic Acid (HA), a component of extracellular matrix ubiquitously found within the human body. Hyaluronic Acid solutions have been shown to reduce postoperative adhesion formation after abdominal surgery (Urman, B. et al., *Effect of Hyaluronic Acid on Postoperative Intraperitoneal Adhesions Formation in the Rat Model*, Fertil. Steril. 1991; 56:563; Shushan A. et al., Hyaluronic Acid for Preventing Experimental Postoperative-intraperitoneal Adhesions, J. Reprod. Med. 1994; 39:398) and orthopaedic operation (Hagberg, L, Gerdin, B., Sodium Hyaluronate as an adjunctive in adhesion prevention after flexor tendon surgery in rabbits, J. Hand. Surg. 1992; 17A:935).

Fidia Advanced Biopolymers has developed chemical derivatives of hyaluronic acid, i.e. internal esters (ACP series) and esters with non-active alcohols (HYAFF series) Rastrelli, A. et al., Hyaluronic Acid Esters, A New Class of Semisynthetic Biopolymers: Chemical and Physico-chemical Properties, Clinical Implant Materials, Advanced in Biomaterials, G. Heinrike, V. Sollz and AJC Lee (Eds), Elsevier, Amsterdam 1990; 9:199–205, which display physico-chemical properties different from that of HA (i.e. higher residence time and ability to be manufactured to produce devices, but possessing tolerability and biocompatibility properties typical of the original biological polymer). Moreover, these derivatives are characterized from a chemical and toxicological point of view.

The aim of the present invention has been to develop batches of derivatives of hyaluronic acid such as ACP gel and HYAFF in an attempt to evaluate the effect in adhesion prevention.

The onset of adherences, or fibrous masses which form between adjacent tissues affected by trauma or ischemia following surgery, is still one of the most serious complications in numerous surgical procedures. A large number of methods have been proposed to avoid this complication, but the problem has remained mainly unsolved.

One proposed method has been the use of suspensions of dextran (dizerega G. S., "Contemporary adhesion prevention" Fertility and Sterility, Vol. 61, No. 2, February '94) injected into the peritoneal cavity after surgery. The clinical results of the use of such dextran solutions have been largely discordant. Moreover, the use of solutions of dextran has been accompanied by frequent complications, including edema, abdominal pain and dyspnea.

The use of barriers in the form of defined structures (e.g. meshes, membranes) (dizerega G. S., "Contemporary adhesion prevention" Fertility and Sterility, Vol. 61, No. 2, February '94) or viscous gels (Genzyme U.S. Pat. No. 4,937,270—U.S. Pat. No. 5,017,229) placed between the injured organs has also been proposed. However, these barriers have generally proved ineffective because they provoke ischemic or inflammatory reactions due to the presence of foreign bodies. The only materials currently approved for clinical use are barriers based on oxidized regenerated cellulose (INTERCEED®) and barriers based on expanded polytetrafluorine ethylene (e-PTFE) (U.S. Pat. Nos. 4,478,665 and 4,482,516) or polyethylene or polypropylene.

In addition to the fact that clinical investigations into the efficacy of such barriers have produced highly discordant results, it must also be noted that both of the aforesaid materials are associated with major contraindications. The use of barrier membranes of e-PTFE or polyethylene or polypropylene involves the implantation of a synthetic material which is foreign to the human body and not biodegradable, and which may require a second surgical operation to remove or reposition the barrier membrane because of undesirable inflammatory-type reactions.

In preclinical and clinical models, meshes based on oxidized regenerated cellulose have proved to be efficacious in preventing the formation of adherences, but only if their application is preceded by thorough hemostasis.

The use of viscous solutions of high-molecular-weight hyaluronic acid (HA) has, therefore, been proposed as an aid in the prevention of adherence (Grainger D. A. et al., "The use of hyaluronic acid polymers to reduce postoperative adhesions", J. of Gynecol. Surg., Vol. 7, No. 2, 1991; Hurman B. et al., "Effect of hyaluronic acid on postoperative intraperitoneal adhesion formation in the rat model", Fertility and Sterility, Vol. 56, No. 3, September 1991; Shushan A. et al., "Hyaluronic acid for preventing experimental postoperative intraperitoneal adhesions:, J. of Reproductive Med., Vol. 39, No. 5, May 1994; Mitchell J. D. et al., "Reduction in experimental pericardial adhesions using a hyaluronic acid bioabsorbable membrane", Eur. J. Cardiothorac. Surg., 8, 149–152, 1994). Hyaluronic acid as such, however, is characterized by very rapid absorption times which are incompatible with the residence time necessary to prevent adhesion. Moreover, natural hyaluronic acid cannot be processed and as such cannot be transformed into biomaterial form. In order to prolong its degradation times and enable it to be processed into various physical forms for use in different surgical sectors, esters of hyaluronic acid and cross-linked derivatives of hyaluronic acid have been developed. The preparation of esters of hyaluronic acid, wherein all or part of the carboxy groups are esterified, the preparation of cross-linked derivatives of hyaluronic acid, wherein part of the carboxy groups undergo cross-linking and their uses in the pharmaceutical, cosmetic and surgical sectors and in that of biodegradable plastic materials are described in U.S. Pat. Nos. 4,851,521 and 4,965,353, EP 0 216 453 and EP 0 341 745.

SUMMARY OF THE INVENTION

The present invention provides biomaterials for use in the prevention of post-surgical adhesions. The biomaterials are comprised of benzyl esters of hyaluronic acid and/or internally cross-linked derivatives of hyaluronic acid and may be in the form of gels, membranes, woven tissues or meshes and nonwoven tissues.

DETAILED DESCRIPTION OF THE INVENTION

Figure 1:
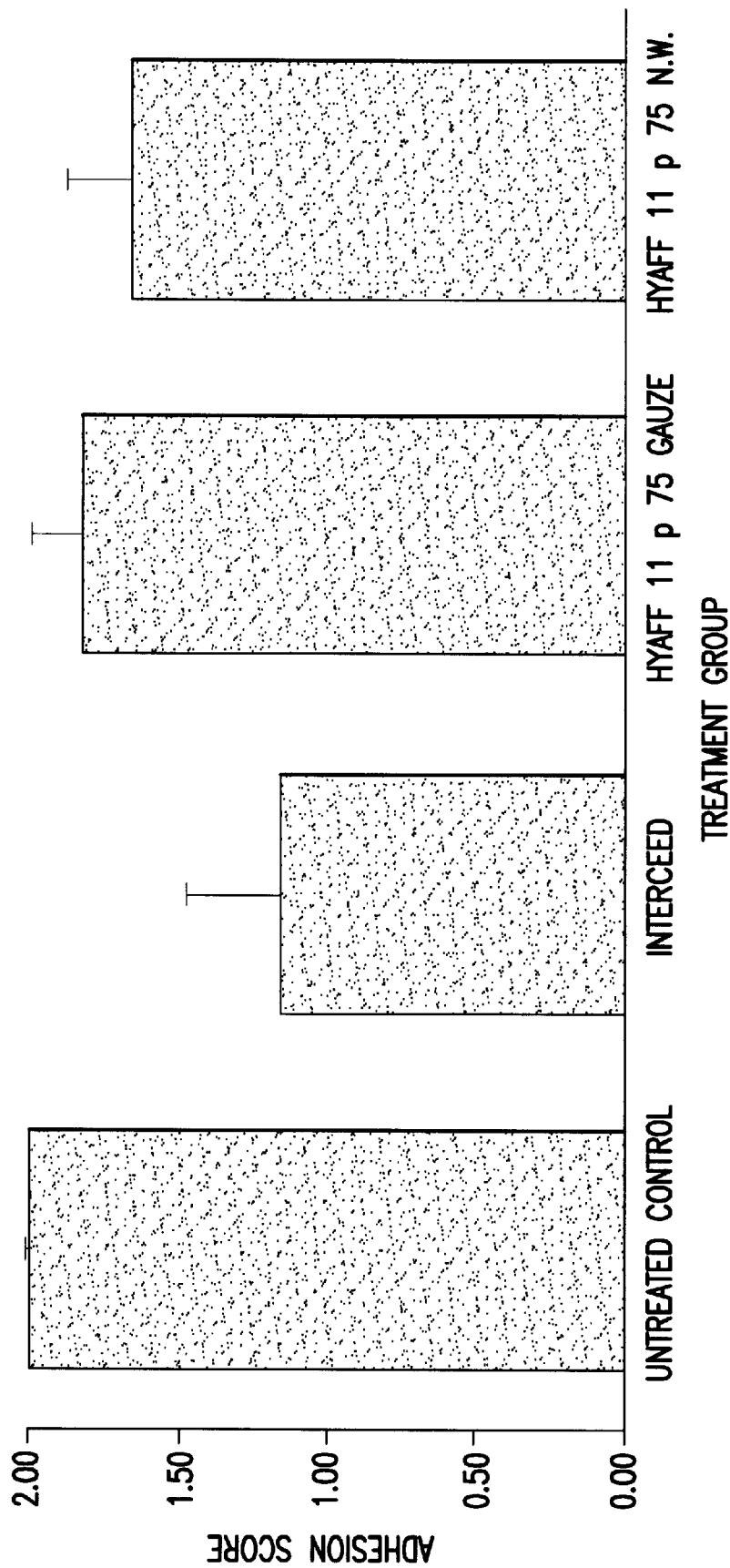
FIGS. 1–26 are graphs of the results of adhesion studies in rat animal models.

The present invention, therefore, describes the preparation of healthcare and surgical articles based on a benzyl ester of hyaluronic acid or on cross-linked derivatives of hyaluronic acid, used singly or in mixtures with one another, characterized by high biocompatibility and transformable into physical forms which make them suitable for various uses in surgery. Surgical fields wherein hyaluronic acid derivatives and materials of the present invention are useful include, but are not limited to, abdominal, laparoscopic, laparotomic, intestinal, gynecological, abdominal pelvic, peritoneal, urogential, orthopedic, spinal, such as dura mater, tendon/nerve such as carpal tunnel, cardiovascular thoracic, oncologic, plastic, esthetic, ENT, paranasal sinuses and transplantation. The materials are also completely biodegradable and do not need to be removed from the application site, thus avoiding a second surgical operation. When prepared in the form of gels, the cross-linked derivatives present materials with significantly greater viscosity than the unmodified polymer and with variable degradation times. Moreover, both the benzyl ester-based materials and the cross-linked derivative-based materials of the present invention can be in the form of membranes, woven tissues or meshes and nonwoven tissues (prepared according to procedures per se described in U.S. Pat. Nos. 4,851,521; 4,956,353,; WO 93/11804; WO 93/11803; WO 94/17837 and EP 0 341 745) and are characterized by the following technical specifications:

the membranes vary in thickness between 10 $\mu$m and 1.5 mm, especially 20–50 $\mu$m;

the tissues or meshes vary in thickness between 200 $\mu$m and 1.5 mm;

the nonwoven tissues are essentially characterized by a basis weight which varies between 20 $g/m^2$ and 500 $g/m^2$ and by a thickness of between 0.2 mm and 5 mm, especially <1 mm.

These materials can be used singly or in association with one another or with other materials constituted by synthetic polymers (e.g. gels based on cross-linked hyaluronic acid+ polypropylene, or membranes essentially constituted by esterified derivatives of HA+polypropylene or membranes comprised of esterified derivatives of HA, coated with a gel of auto-crosslinked HA).

Indeed, the present invention also concerns the use of composite materials in the form of gels (for the cross-linked derivatives), membranes, woven or nonwoven tissues, essentially constituted by the benzyl esters or cross-linked derivatives of hyaluronic acid in association with nonbiodegradable materials in the form of meshes or membranes or nonwoven tissues such as e-PTFE, polyethylene, polypropylene, polyester (Dacron®). The present invention, therefore concerns a new class of healthcare and surgical articles to be used in the field of surgery for the prevention of the formation of post-surgical adherence.

The materials of the present invention can also be used in association with active agents useful in promoting healing, reducing inflammation, preventing infection, etc. Such active agents include steroidal and non-steroidal antiinflammatories, fibrinolytics, hemostatics, antithrombotics, growth factors, antitumorals and antibiotics including antibacterials, antivirals, antifungals. These active agents may be applied separately and immediately prior to or simultaneously with the hyaluronic derivation adhesion prevention material. Alternative, the active agent may be impregnated into the adhesion prevention materials.

Materials

As noted above, the present invention is characterized by materials comprised of derivatives of hyaluronic acid, especially benzyl ester derivatives and internally cross-linked derivatives.

The term "hyaluronic acid" (also referred to as "HA" hereinafter) is used in literature to designate an acidic polysaccharide with various molecular weights constituted by resides of D-glucuronic acid and N-acetyl-D-glucosamine, which naturally occur in cellular surfaces, in the basic extracellular substances of the connective tissues of vertebrates, in the synovial fluid of joints, in the vitreous humor of the eye, in the tissue of the human umbilical cord and in cocks' combs.

Hyaluronic acid plays an important role in the biological organism, firstly as a mechanical support of the cells of many tissues, such as the skin, the tendons, the muscles and cartilage and it is therefore the main component of the extracellular matrix. But hyaluronic acid also performs other functions in the biological processes, such as the hydration of tissues, lubrication, cellular migration, cell function and differentiation. (See for example, A. Balazs et al., Cosmetics & Toiletries, No. 5/84, pages 8–17). Hyaluronic acid may be extracted from the above-mentioned natural tissues, such as cocks' combs, or also from certain bacteria. Today, hyaluronic acid may also be prepared by microbiological methods. The molecular weight of whole hyaluronic acid obtained by extraction is in the region of 8–13 million. However, the molecular chain of the polysaccharide can be degraded quite easily under the influence of various physical and chemical factors, such as mechanical influences or under the influence of radiation, hydrolyzing, oxidizing or enzymatic agents. For this reason, often in the ordinary purification procedures of original extracts, degraded fractions with a lower molecular weight are obtained. (See Balazs et al., cited above). Hyaluronic acid, its molecular fractions and the respective salts have been used as medicaments and their use is also proposed in cosmetics (see for example, the above-mentioned article by Balazs et al., and the French Patent No. 2478468).

Although the term "hyaluronic acid" is commonly used in an improper sense, meaning, as can be seen from above, a whole series of polysaccharides with alternations of residues of D-glucuronic acid and N-acetyl-D-glucosamine with varying molecular weights or even degraded fractions of the same, and although the plural form "hyaluronic acids" may seem more appropriate, the discussion herein shall continue to use the singular form to refer to hyaluronic acid in its various forms including its molecular fractions, and the abbreviation "HA" will also often be used to describe this collective term.

1. The Benzyl Ester Derivatives:

The first preferred material of the invention is based on the benzyl ester of hyaluronic acid, particularly the 80–100% esters wherein 80% to 100% of the HA carboxyl groups are esterified. Those benzyl esters wherein 80–99% of the HA carboxyl groups are esterified with a benzyl group are referred to as "partial esters", because only a portion of the carboxyl groups are esterified and the remaining carboxyl groups are either free or salified with an alkaline or alkaline earth metal, such as sodium, calcium or potassium.

Most preferred for the- biomaterials of the invention are so-called "total" benzyl esters wherein all of the HA carboxy groups are esterified. In these total esters, all of the HA carboxy groups may be esterified with a benzyl group (also referred to as HYAFF 11). A partial ester is one wherein a portion (75 to 99%) but not all of the HA carboxy groups are esterified with a benzyl group. "Mixed" esters are those where in the HA carboxy groups are esterified with more than one type of ester group. The mixed esters may be total esters in that for example, a portion (75–99%) may be esterified with a benzyl group and all of the remaining carboxyl groups esterified with the lipid chain/alkyl residue from a $C_{10-20}$ aliphatic alcohol. Of these aliphatic alcohols, palmitic alcohol ($C_{16}$-hexadecyl) and stearic alcohol ($C_{18}$ octadecyl) are the most preferred. The benzyl esters of hyaluronic acid according to the invention may be prepared by methods known per se for the esterification of carboxylic acids, for example by treatment of free hyaluronic acid with the alcohol (benzyl and/or $C_{10}$–$C_{20}$ alcohol) in the presence of catalyzing substances, such as strong inorganic acids or ionic exchangers of the acid type, or with an etherifying agent capable of introducing the desired alcoholic residue in the presence of inorganic or organic bases.

The benzyl hyaluronic esters may, however, be prepared to advantage according to a particular method described in EP 0 216 453. This method consists of treating a quaternary ammonium salt of hyaluronic acid with an etherifying agent, preferably in an aprotic organic solvent.

For the preparation of the benzyl esters it is possible to use hyaluronic acids of any origin, such as for example, the acids extracted from the above mentioned natural starting materials, for example, from cocks' combs. The preparation of such acids is described in literature: preferably, purified hyaluronic acids are used. According to the invention, especially used are hyaluronic acids comprising molecular fractions of the integral acids obtained directly by extraction of the organic materials with molecular weights varying within a wide range, for example, from about 90%–80% (M=11.7–10.4 million) to 0.2% (M=30,000) of the molecular weight of the integral acid having a molecular weight of 13 million, preferably between 5% and 0.2%. Such fractions may be obtained with various procedures described in literature, such as by hydrolyzing, oxidizing, enzymatic or physical procedures, such as mechanical or radiational procedures. Primordial extracts are therefore often formed during these same purification procedures (for example, see the article by Balazs et al., quoted above in "Cosmetics & Toiletries"). The separation and purification of the molecular fractions obtained are brought about by known techniques, for example by molecular filtration.

One fraction of purified HA suitable for use according to the invention is for example that known as "non-inflammatory-NIF-NaHA sodium hyaluronate described by Balazs in the booklet "Healon"—A guide to its use in Ophthalmic Surgery, D. Miller & R. Stegmann, eds. John Wiley & Sons, N.Y., 81983: p 5.

Particularly important as starting materials for the benzyl ester are two purified fractions obtainable from hyaluronic acid, for example the ones extracted from cocks' combs, known as "Hyalastine" and "Hyalectin". The fraction Hyalastine has an average molecular weight of about 50,000 to 100,000 while the fraction Hyalectin has an average molecular weight of between about 500,000 and 730,000. A combined fraction of these two fractions has also been isolated and characterized as having an average molecular weight of about 250,000 to about 350,000. This combined fraction may be obtained with a yield of 80% of total hyaluronic acid available in the particular starting material, while the fraction Hyalectin may be obtained with a yield of 30% and the fraction Hyalastine with a yield of 50% of the starting HA. The preparation of these fractions is described in EP 0 138 572.

The following Examples describe the preparation of the benzyl esters of HA.

EXAMPLE 1

Preparation of the 100% Benzyl Ester of Hyaluronic Acid (HYAFF 11)

12.4 g of HA tetrabutylammonium salt with a molecular weight of 170,000 corresponding to 20 m.Eq. of a monomeric unit are solubilized in 620 ml of dimethylsulfoxide at 250, 4.5 g (25 m.Eq.) of benzyl bromide and 0.2 g of tetrabutylammonium iodide are added, the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty four hours at 30°.

9 g of the benzyl ester product in the title are obtained. Quantitative determination of the ester groups is carried out according to the method described on pages 169–172 of Siggia S. and Hann J. G. "Quantitative organic analysis via functional groups" 4th edition, John Wiley and Sons.

EXAMPLE 2

Preparation of the 100% Benzyl Ester of Hyaluronic Acid (HYAFF 11)

3 g of the potassium salt of HA with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30°.

3.1 g of the benzyl ester product in the title are obtained. Quantitative determination of the ester groups is carried out according to the method described on pages 1698–172 of Siggia S. and Hanna J. G. "Quantitative organic analysis via functional groups" 4th Edition, John Wiley and Sons.

EXAMPLE 3

Preparation of a Hyaluronic Acid Derivative With 75% of its Carboxyl Functions Esterified With Benzyl Alcohol and the Remaining 25% Esterified With Octadecyl Alcohol (Stearyl Alcohol, $CH_3$—$(CH_2)_{16}$—$CH_2$—$OH$)

6.21 g of tetrabutyl ammonium salt of hyaluronic acid with a molecular weight of 180,000 Daltons (10 mEq) are solubilized in 248 ml of dimethylsulfoxide (DMSO) at room temperature.

This solution is supplemented with 0.89 ml of benzyl bromide (7.5 mEq) and the solution is left to stand at 30° C. for 12 hours. The solution is then cooled to room temperature and supplemented with 0.83 g of octadecyl bromide (2.5 mEq). The solution is heated to 30° C. for 24 hours. A 2.5% solution (w/w) of NaCl in water is then added and the resulting mixture is poured into 750 ml of acetone, stirring the while. A precipitate is formed which is filtered and washed three times in 100 ml of acetone/water 5:1, three times with 100 ml of acetone and then dried in a high vacuum for 24 hours at 30° C. 5.1 grams of the desired product are thus obtained. Quantitative determination of the benzyl alcohol and hexadecyl alcohol content is performed by gas chromatography following alkaline hydrolysis. The total content of ester groups is quantified according to the saponification method described on pages 169–172 of "Quantitative organic analysis via functional group" Fourth Edition (John Wiley and Sons Publication).

EXAMPLE 4

Preparation of a Hyaluronic Acid Derivative With 75% of its Carboxyl Functions Esterified With Benzyl Alcohol and the Remaining 25% Esterified With Hexadecyl Alcohol (Cetyl Palmityl Alcohol, $CH_3$—$(CH_2)_{14}$—$CH_2$—$OH$)

6.21 g of tetrabutyl ammonium salt of hyaluronic acid with a molecular weight of 180,000 Daltons (10 mEq) are solubilized in 248 ml of dimethylsulfoxide (DMSO) at room temperature.

This solution is supplemented with 0.89 ml of benzyl bromide (7.5 mEq) and the solution is left to stand at 30° C. for 12 hours. The solution is then cooled to room temperature and supplemented with 0.76 g of hexadecyl bromide (2.5 mEq). The solution is heated to 30° C. for 24 hours. A 2.5% solution (w/w) of NaCl in water is then added and the resulting mixture is poured into 750 ml of acetone, stirring the while. A precipitate is formed which is filtered and washed three times in 100 ml of acetone/water 5:1, three times with 100 ml of acetone and then dried in a high vacuum for 24 hours at 30° C. Five grams of the desired product are thus obtained. Quantitative determination of the benzyl alcohol and hexadecyl alcohol content is performed by gas chromatography following alkaline hydrolysis. The total content of ester groups is quantified according to the saponification method described on pages 169–172 of "Quantitative organic analysis via functional group" Fourth Edition (John Wiley and Sons Publication).

2. The Internal Cross-linked Hyaluronic Acid Derivatives (ACP Derivatives):

The cross-linked hyaluronic acid derivatives used in the materials of the present invention are described in EP 0 341 745. These cross-linked derivatives are inter and/or intramolecular esters of hyaluronic acid wherein a part of the carboxy groups are esterified with hydroxyl groups of the same molecule and/or of different molecules of hyaluronic acid, thus forming lactone or intermolecular ester bonds. These "inner" esters in which there is no intervention by OH groups of other alcohols, can also be defined as "autocrosslinked hyaluronic acid" since the formation of a mono- or polymolecular cross-link is the consequence of the above-mentioned internal esterification. The adjective "cross-linked" refers to the crosswise connections between the carboxyls and hydroxyls of the hyaluronic acid molecules.

The auto-crosslinked products are particularly partial inner esters wherein the percentage of "cross-links" varies preferably between 0.5 to 20%, especially 4.5/5.0% of the number of carboxy groups in the hyaluronic acid. In the preparation process, the carboxy groups of the HA molecule are activated by the addition of substances capable of inducing such activation. The unstable intermediate products obtained from the activation reaction separate spontaneously, either after the addition of catalysts and/or following a rise in temperature, forming the above mentioned inner ester bonds with hydroxyls of the same or other hyaluronic acid molecule. According to the degree of inner esterification desired, either all or an aliquot part of the carboxy functions are activated (the aliquot part being obtained by using an excess of activating substances or by suitable dosing methods).

The carboxy groups to be converted into inner ester groups can be activated starting from hyaluronic acid containing free carboxy groups, or, preferably, from HA containing salified carboxy groups, for example, metal salts, preferably alkaline or alkaline earth metals, and above all with quaternary ammonium salts, such as those described hereafter. Salts with organic basis such as amines can, however, also be used as starting substances.

Methods for the activation of free or salified carboxy groups are per se known, particularly in the field of peptide synthesis, and those skilled in the art can easily determine which method is the most suitable, especially whether or not to use the starting substances in their free or salified form. Activation methods per se known for peptide synthesis procedures and useful in the preparation procedures of the present invention are described, for example, in Bodanszky, M., In search of new methods in peptide synthesis, Int. J. Peptide Protein Res. 25, 1985, 449–474; and Gross, E. et al, The Peptides, Analysis Synthesis, Biology, Academic Press, Inc., 1979, Vol. 1, Chapter 2. According to such procedures, a carboxyl component is activated, that is, a carboxyl component is converted to a reactive form. Such activation typically involves a reaction between an acid and an activating agent according to the scheme:

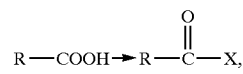

wherein X is an electron withdrawing moiety. Most activated derivatives of carboxylic acids, therefore, are mixed anhydrides, including in the broad sense also acid azides and acid chlorides which can be considered mixed anhydrides of hydrazoic acid and HCl as the activating agents. In addition, activation of a carboxyl component can be accomplished by the formation of intermediate "activated esters". These "activated esters" can be of various types, but particularly useful "activated esters" are those prepared by use of dicyclohexylcarbodiimide, p-nitrophenyl esters, trichlorophenyl esters, pentachlorophenyl esters, and O-acyl derivatives of hydroxylamines, particularly esters of N-hydroxysuccinimide.

All of these various types of activation procedures are useful in the preparation of the cross-linked HA of the invention, as all of these procedures can be characterized as importantly involving the reaction of a carboxyl group with an activating agent which essentially results in the formation of a substituent group that is easily reactive with a hydroxyl group so as to easily form the inner ester bonding characteristic of the products of the invention, the number of carboxy functions to be converted into inner esters in proportion to the number of activated carboxy functions and this number depends on the quality of the activating agent used.

The preferred procedure for preparation of cross-linked HA is therefore characterized by treating HA, having free or salified carboxy groups, with an agent which activates the carboxy function, possibly in the presence of an auxiliary agent favoring the formation of intermediate activated derivatives and/or a tertiary organic or inorganic base, exposing the mixture to heating or irradiation (particularly with UV light), and if desired, by salifying free carboxy groups or by freeing salified carboxy groups. Of the substances able to activate the carboxy group, the conventional ones described in literature can be used, for example, those usually used in the synthesis of peptides, except however those which would have the effect of altering or destroying the molecular structure of the starting HA, such as those used for the formation of carboxyl halides. Preferred substances which lead to the formation of activated esters are those, such as, carbodiimides, dicyclohexylcarbodiimide, benzyl-isopropylcarbodiimide, benzyl-ethyl-carbodiimide; ethoxyacetylene; Woodward's reagent (N-ethyl-5-phenylisoxazolium-3-sulfonate) or halogen derivatives from aliphatic, cycloaliphatic or aromatic hydrocarbons, or from heterocyclic compound with halogen made mobile by the presence of one or more activating groups, such as chloroacetonitryl and especially the salts of 2-chloro-N-alkylpyridine, such as chloride of 2-chloro-N-methylpyridine or other alkyl derivatives with inferior alkyl groups, such as those with up to 6 carbon atoms. In the place of chloride derivatives, other halogen derivatives can of course be used, such as bromide derivatives.

This activation reaction can be carried out in organic solvents, especially aprotic solvents such as dialkylsulfoxides, dialkylcarboxylamides, such as in particular lower alkyl dialkylsulfoxides, particularly dimethylsulfoxide, polymethylene sulfoxides, such as tetramethylene sulfoxide, dialkyls or polymethylene sulfones, such as tetramethylene sulfone, sulfolane and lower alkyl dialkyamides of lower aliphatic acids in which the alkyl groups have a maximum of six carbon atoms, such as dimethyl or diethyl formamide or dimethyl or diethyl acetamide. Other solvents may also be used, however, and these need not always be aprotic, such as alcohols, ethers, ketones, esters, such as lower aliphatic dialkyloxyhydrocarbides, such as dimethoxyethane and especially aliphatic or heterocyclic alcohols and ketones with a low boiling point, such as lower N-alkyl-pyrrolidones, such as N-methylpyrrolidone or N-ethyl-pyrrolidone, hexafluorisopropanol and trifluoroethanol. If halogen derivatives are used as carboxyl-activating substances, especially in the form of salts, such as the above-mentioned 2-chloro-N-methylpyridinium chloride, it is better to use a metal salt or a salt of the organic base of the starting polysaccharide, especially one of the quaternary ammonium salts described hereafter, such as tetrabutyl ammonium salt. These salts have the special advantage of being very soluble in the abovesaid organic solvents in which the cross-linking reaction is best effected, thus guaranteeing an excellent yield It is advisable to add to the mixture a substance capable of subtracting acid, such as organic bases, carbonates, bicarbonates or alkaline or alkaline earth acetates, or organic bases and especially tertiary bases such as pyridine and its homologues, such as collidine, or aliphatic amine bases, such as triethylamine or N-methylpiperazine.

The use of quaternary ammonium salts represents a particularly advantageous procedure. Such ammonium salts are well known and are prepared in the same way as other known salts. They derive from alkyls having preferably between 1 and 6 carbon atoms. It is preferable to use tetrabutyl ammonium salts. One variation in the procedure in which quaternary ammonium salts are used, consists in reacting an alkaline salt, for example, sodium or potassium salt, in the presence of catalyzing quantity of a quaternary ammonium salt, such as tetrabutylammonium iodide.

The substances which catalyze activation of the carboxy groups to be added to the activating agents are reported in literature and these too are preferably bases such as those mentioned previously. Thus, for example, when the carboxy groups are activated with isothiazoline salts it is preferable to add some triethylamine to the reaction mixture.

The reaction of formation of activated intermediates, such as and especially esters, is carried out at the temperature recommended in literature and this temperature can, however, be varied should circumstances require as can be easily determined by one skilled in the art. The formation of inner ester bonds can come about within a fairly wide temperature range, for example between 0° and 150°, preferably room temperature or slightly above, for example between 20° and 75°. Raising the temperature favors the formation of inner ester bonds, as does exposure to radiations of suitable wavelength, such as ultraviolet rays.

The substrate of hyaluronic acid can be of any origin, and can be of the various types discussed above. The preferred HA starting materials are those with an average molecular weight of 150,000 to 730,000, especially 150,000 to 450,000 daltons.

In addition, the amount of internal cross-linking can vary, but preferred materials according to the invention utilize HA cross-linked to a degree of 4.5 to 5.0% of the carboxyl groups.

When prepared in the form of gels, the cross-linked dervatives have greater viscosity than the unmodified hyaluronic acid. By controlling the viscosity, both the degradation time and effect on adhesion prevention can be varied. Preferred are those gels having a viscosity of at least 200 $Pa*sec^{-1}$. More preferred are gels with a viscosity of at least 250 $Pa*sec^{-1}$ or even 300 $Pa*sec^{-1}$ and most preferred are those gels having a viscosity of at least 350 $Pa*sec^{-1}$ or 400 $Pa*sec^{-1}$.

The following Examples describe the preparation of useful cross-linked HA products for making the materials of the invention.

EXAMPLE 5

Preparation of 1% Cross-linked Hyaluronic Acid (ACP 1%)

Product Description:

1% of carboxy groups used in internal esterification.

99% of carboxy groups salified with sodium.

6.21 g of HA tetrabutylammonium salt with a molecular weight of 170,000 corresponding to 10 mEq of a monomeric unit are solubilized in 248 ml of DMSO at 25° C., 0.01 g (0.1 mEq) of triethylamine are added.

EXAMPLE 6

Preparation of 5% Cross-linked Hyaluronic Acid (ACP 5%)

Product Description:
  5% of carboxy groups used in internal esterification.
  95% of carboxy groups salified with sodium.

6.21 g of HA tetrabutylammonium salt with a molecular weight of 85,000 corresponding to 10 mEq of a monomeric unit are solubilized in 248 ml of DMSO at 25° C., 0.051 gr (0.5 mEq) of triethylamine are added and the resulting solution is agitated for 30 minutes.

A solution of 0.128 gr (0.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone water 5:1 and three times with 100 ml of acetone and lastly vacuum-dried for 24 hours at 30°.

3.95 grs of the title compound are obtained. Quantitative determination of the ester groups is carried out according to the saponification method described on pp. 169–172 of "Quantitative Organic Analysis Via Functional Groups", 4th Edition, John Wiley and Sons Publication.

EXAMPLE 7

Preparation of 10% Cross-linked Hyaluronic Acid (ACP 10%)

Product Description:
  10% of carboxy groups used in internal esterification.
  90% of carboxy groups salified with sodium.

6.21 g of HA tetrabutylammonium salt with a molecular weight of 620,000 corresponding to 10 mEq of a monomeric unit are solubilized in 248 ml of DMSO at 25° C. 0.101 gr (1.0 mEq) of triethylamine is added and the resulting solution is agitated for 30 minutes.

A solution of 0.255 gr (1.0 mEq) of 2-chloro-1-methyl-pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed when is then filtered and washed three times in 100 ml of acetone water 5:1 and three times with 100 ml of acetone and lastly vacuum-dried for 24 hours at 30°.

3.93 grs of the title compound are obtained. Quantitative determine of the ester groups is carried out according to the saponification method described on pp. 169–172 of "Quantitative Organic Analysis Via Functional Groups", 4th Edition, John Wiley and Sons Publication.

EXAMPLE 8

Preparation of 10% Cross-linked Hyaluronic Acid (ACP 10%)

Product Description:
  10% of carboxy groups used in internal esterification.
  90% of carboxy groups salified with sodium.

6.21 gr of HA tetrabutylammonium salt with a molecular weight of 170,000 corresponding to 10 mEq of a monomeric unit are solubilized in 248 ml of DMSO at 25° C., 0.118 gr (1 mEq) of pyridine chloride are added and the resulting solution is agitated for 30 minutes.

A solution of 0.16 g (mEq) of N-benzyl-N-ethyl carbodiimide in 20 ml of DMSO is slowly added drop by drop over a time interval of 1 hour and the mixture is kept at a temperature of 300 for 45 hours.

A solution made up of 100 ml of water and 2.5 of sodium chloride is added and the resulting mixture is slowly poured into 750 ml of acetone, maintaining continual agitation. A precipitate is formed which is then filtered and washed three times with 100 ml of acetone/$H_2O$ 5:1 and three times with 100 ml of acetone finally vacuum-dried for 24 hours at a temperature of 30°.

3.9 g of the title compound are obtained. Quantitative determination of the total ester groups is carried out according to the saponification method described on pp. 169–172 of "Quantitative Organic Analysis Via Functional Groups", 4th Edition, John Wiley and Sons Publication.

3. Preparation of the Biomaterials:

The following Examples describe the preparation of surgical/healthcare products according to the invention which comprise the total benzyl ester of HA or an auto-crosslinked HA derivative, or combinations thereof. As noted above, procedures for the preparation of the membranes, woven tissues, woven meshes, and nonwoven tissues are described in U.S. Pat. Nos. 4,851,521; 4,965,353, WO 93/11804; WO 93/11803; WO 94/17837 and EP 0 341 745.

EXAMPLE 9

Preparation of a Product Based on HYAFF 11+ Polypropylene Mesh

A solution of HYAFF 11 (100% benzyl ester) in DMSO is prepared in accordance with Example 1 or 2 (110 mg/ml). Once solubilization is complete, the solution is filtered through a 20 μm filter cloth and degassed by leaving it to stand in a vacuum for 2 hours. 5 ml of the solution are poured out and spread onto a glass plate, after which the polypropylene mesh (preferably 6×11 cm) is placed on top and a further 10 ml of the solution is poured over it. This is spread evenly over the mesh and any excess is eliminated.

The glass plate is immersed in a bath containing ethanol/$H_2O$ (90:10) for 5 hours to allow the preparation to coagulate and the plate to become detached; the preparation is then immersed in a bath of absolute ethanol for 16 hours. It is then dried on a plate in a vacuum for 30 minutes at 63° C.

EXAMPLE 10

Preparation of a Product Based on Woven Tissue of HYAFF 11 Covered With a Film of HYAFF 11

A solution of HYAFF 11 in DMSO is prepared (110 μg/ml) in accordance with Example 1 or 2. Once solubilization is complete, the solution is filtered through a 20 μm filter cloth and degassed by leaving it to stand in a vacuum for 2 hours. 5 ml of the solution are poured out and spread onto a glass plate, after which the HYAFF 11 gauze (10×20 cm) is placed on top, taking care to make it adhere without any creases or air bubbles, and a further 10 ml of the solution is poured over it. This is spread evenly over the gauze and any excess is eliminated.

The glass plate is immersed in a bath containing ethanol for 30 minutes to allow the preparation to coagulate and the plate to become detached. The preparation is then left in ethanol for 16 hours and dried on a plate in a vacuum at 63° C. for 30 minutes.

EXAMPLE 11

Membrane of HYAFF 11 With Reinforcement of HYAFF 7

A composite membrane comprising the hyaluronic acid benzyl ester HYAFF 11, i.e., hyaluronic acid esterified 100% with benzyl alcohol, with a mesh reinforcement comprising the hyaluronic acid ethyl ester HYAFF 7, i.e., hyaluronic acid esterified 100% with ethanol, basis weight 14 mg/cm$^2$, 0.25 mm thick, minimum tensile strength at break and elongation when dry, 400 Kg/cm$^2$ and 7%, respectively, minimum tensile strength and elongation when wet, 50 Kg/cm$^2$ and 55%, respectively, tear strength when dry, 90 Kg/cm$^2$ tear strength when wet, 50 Kg/cm2 was produced according to the following procedure.

The HYAFF 7 mesh was obtained starting with a solution of HYAFF 7 dimethylsulfoxide at a concentration of 125 mg/ml. The solution is fed by a gear metering pump into a spinneret for wet extrusion composed of 100 holes each measuring 65 microns in diameter.

The extruded multiple thread is passed into a coagulation bath containing absolute ethanol and is then moved over transporting rollers into three successive rinsing baths, also containing absolute ethanol. The ratio between the speed of the third roller (III) and the speed of the first roller (I) is called the drafting ratio, and has a value of 1.05, while the speeds of the single rollers are: 23 rpm (roller I), 24 rpm (rollers II and III), 25 rpm (roller IV). Once the multiple thread has been passed through the rinsing baths it is dried with warm air at a temperature of 45° C. and wound onto a winding frame. The thread is 237 denier. The multiple thread is then twisted 135 times per meter and woven on a loom into a smooth knitted fabric with a gauge of 14. From the loom the fabric is fed through a calendar, which thins it down.

The polymeric matrix is applied by two airbrushes which spray a solution of HYAFF 11 in dimethylsulfoxide at a concentration of 40 mg/ml. The mesh thus sprayed is passed into a coagulation bath containing absolute ethanol, into a rinsing chamber containing pure, distilled water and into a special drying chamber with a temperature of 50° C.

EXAMPLE 12

Nonwoven Fabric Comprised of HYAFF 11

A nonwoven fabric comprising hyaluronic acid benzyl ester HYAFF 11, weighing 40 g/mq, 0.5 mm thick, was produced by the following procedure.

A solution of HYAFF 11 in dimethylsulfoxide at a concentration of 135 mg/ml is prepared in a tank and fed by a gear metering pump into a spinneret for wet extrusion composed of 3000 holes each measuring 65 microns.

The extruded mass of threads passes into a coagulation bath containing absolute ethanol. It is then moved over transporting rollers into two successive rinsing baths containing absolute ethanol. The drafting ratio of the first roller is set at zero while the drafting ratio between the other rollers is set at 1.05. Once it has been passed through the rinsing baths, the hank of threads is blown dry with hot air at 45°–50° C. and cut with a roller cutter into 40 mm fibers.

The mass of fibers thus obtained is tipped into a chute leading to a carding/cross lapping machine from which it emerges as a web, 1 mm thick and weighing 40 mg/mq. The web is then sprayed with a solution of HYAFF 11 in dimethylsulfoxide at 80 mg/ml, placed in an ethanol coagulation bath, in a rinsing chamber, and lastly in a drying chamber.

The final thickness of the material is 0.5 mm.

EXAMPLE 13

Nonwoven Fabric Comprised of HYAFF 11 and HYAFF 7

A nonwoven fabric weighing 200 gr/mq and 1.5 mm thick comprising a mixture of the ethyl ester of hyaluronic acid, HYAFF 7, and of hyaluronic acid benzyl ester, HYAFF 11, in equal quantities, was obtained by the following procedure.

Fibers of HYAFF 7 and HYAFF 11, measuring 3 mm in length, obtained by the spinning process described in Example 10 were thoroughly mixed in a spiral mixer. The mixture of fibers was fed into a carding machine from which it emerged as a 1.8 mm thick web weighing 200 g/mq.

The web was put through a needle punching machine, which transformed it into a 1.5 mm thick unwoven fabric weighing 200 g/mq, with the two materials perfectly mixed together.

EXAMPLE 14

Nonwoven Fabric of Partial and Total Benzyl Ester

A nonwoven fabric weighing 40 g/mq and 0.5 mm thick comprising a mixture of hyaluronic acid benzyl ester, HYAFF 11, and a partial (75%) benzyl ester of hyaluronic acid, HYAFF 11p75, wherein 75% of the carboxy groups are the benzyl ester and the remaining 25% are salified with sodium, in equal percentages, was produced by the following procedure.

HYAFF 11p75 is prepared as follows. 10 g of hyaluronic acid tetrabutylammonium salt, mw=620.76, equal to 16.1 nmole, are solubilized in a mixture of N-methyl pyrrolidone/$H_2O$, 90/10, 2.5% in weight, to obtain 400 mls of solution. The solution is cooled to 10° C., then purified $N_2$ is bubbled through it for 30 minutes. This is then esterified with 1.49 ml (equal to 12.54 mmole) of benzyl bromide. The solution is gently shaken for 60 hours at 15–20° C.

Subsequent purification is achieved by precipitation in ethyl acetate following the addition of a saturated solution of sodium chloride, and subsequent washings with a mixture of ethyl acetate/absolute ethanol, 80/20. The solid phase is separated by filtration, and treated with anhydrous acetone. 6.8 g of product are thus obtained, equal to a yield of about 95%.

Fibers of HYAFF 11 and HYAFF 11p75, 40 mm long, obtained by the process described in Example 12, were thoroughly mixed in a spiral mixer.

The mixed fibers were fed into a carding machine from which they emerged as a 1 mm thick web weighing 40 mg/mq. The web was then sprayed with a solution of HYAFF 11 in dimethylsulfoxide at 80 mg/ml, placed in an ethanol coagulation bath, then in a rinsing chamber containing water or a mixture of water and ethanol in a ratio of from 10 to 95% ethanol, and finally in a drying chamber.

The material has a final thickness of 0.5 mm, and the fibers of HYAFF 11 and HYAFF 11p75 are perfectly mixed and adhered together.

EXAMPLE 15

Multilayer Nonwoven Tissue Based on HYAFF 11

A multilayer nonwoven tissue composed of a layer of hyaluronic acid benzyl ester, HYAFF 11, and a layer of nonwoven viscose (Jettex 2005 from ORSA), basis weight 80 g/mq, thickness 2 mm, and water absorption percentage 560% by weight, was obtained by the following procedure.

The layer which comes into contact with the skin comprises fibers of HYAFF 11 produced by the wet-spinning technique in the form of 30 g/mq sheet. Fibers were made into sheets.

This layer is joined by stitching to a second layer of nonwoven viscose tissue with a basis weight of 30 g/mq.

The final nonwoven product thus comprises two perfectly adhered layers with a total basis weight of 80 g/mq, a thickness of 2 mm, and a water absorption percentage of 560% by weight.

EXAMPLE 16

Multilayer Nonwoven Tissue Based on HYAFF 11

A multilayer nonwoven tissue comprising a mixed layer of hyaluronic acid benzyl ester, HYAFF 11, and calcium alginate in a 1:1 ratio and a reinforcing nonwoven tissue of polypropylene (spunbonded nonwoven base, 50 g/mq from NEUBERGER) with a basis weight of 70 g/mq, a thickness of 1.5 mm, and a water absorption percentage of 450% by weight, was obtained by the following procedure.

Fibers of HYAFF 11 and calcium alginate, 40 mm in length, obtained by conventional wet-spinning techniques, were mixed, made into a 20 g/mq sheet, and joined by stitching to a spunbonded nonwoven tissue with a basis weight of 50 g/mq.

The resulting material comprises two layers of nonwoven tissue with a total basis weight of 70 g/mq, a thickness of 1.5 mm, and a water absorption percentage of 450% by weight.

EXAMPLE 17

Multilayer Nonwoven Tissue Based on HYAFF 11

A multilayer nonwoven tissue comprising a layer of hyaluronic acid benzyl ester HYAFF 11 and a layer of polyurethane foam such as LYOBEND (from DELCON) with a basis weight of 100 g/mq, a thickness of 6 mm, and a water absorption percentage of 860% by weight, was obtained by the following procedure.

The layer which comes into contact with the skin comprises fibers of HYAFF 11 produced by the wet-spinning technique and made into a 45 g/mq sheet which is joined by stitching to a second layer of polyurethane foam.

The resulting nonwoven product comprises two perfectly adhered layers with a total basis weight of 100 g/mq, a thickness of 6 mm, and a water absorption percentage of 860% by weight.

EXAMPLE 18

Preparation of a Membrane Made of a Derivative of Hyaluronic Acid With 80% of the Carboxy Functions Esterified With Benzyl Alcohol ($C_6H_5$—$CH_2$—OH), 10% of the Carboxy Functions Involved in the Formation of Inner Ester Bonds and the Remaining 10% Salified With Sodium 6.21 g of the tetrabutylammonium salt of hyaluronic acid with a molecular weight of 180,000 Daltons (10 mEq) are solubilized in 248 ml of dimethylsulfoxide (DMSO) at ambient temperature. To this solution are added 0.951 ml of benzyl bromide (8.0 mEq) and the solution is left to stand for 12 hours at 30° C. 0.101 g of triethylamine (1.0 mEq) are added and the solution is stirred for 30 minutes. A solution of 0.255 g (1.0 mEq) of 2-chloro-1-methyl-pyridine iodide in 60 ml of DMSO is added and the mixture is left to stand for 15 hours at 30° C.

A 2.5% solution (w/v) of NaCl in water is added and the resulting mixture is poured into 750 ml of acetone, while stirred. A precipitate is formed which is filtered and washed three times in 100 ml of acetone/water 5:1, three times with 100 ml of acetone and finally vacuum-dried for 24 hours at 30° C. 4.5 g of the desired product are thus obtained. Quantitative determination of the benzyl alcohol content is performed by gas chromatography following alkaline hydrolysis. The total ester group content is measured by the saponification method described on pages 169–172 of "Quantitative analysis via functional groups", fourth edition, John Wiley and Sons Publication.

The ester derivative thus prepared is solubilized to a concentration of 150 mg/ml in DMSO at a temperature of 30° C. The solubilized derivative is filtered through a 20 micron mesh and placed in an extrusion reactor connected to a film extruder with a thickness of <1 mm. The product is extruded in a coagulation bath containing a solvent which enables the DMSO to be extracted from the product (e.g. ethanol), and the material from the film extruder is wound onto a series of rolls equipped with air fans to dry the membrane.

Preclinical/Clinical Studies

The following studies report results which show the usefulness of the products of the invention in preventing post-surgical adhesions and show the improved results for those products as compared to prior existing products.

Study 1

This study demonstrates the high incidence of surgical adhesion formation observed in a model of lesion induced in rat liver, established as the positive control to compare the preventive action of healthcare and surgical articles derived from HA, in adherence formation.

For these experiments, Sprague Dawley rats weighing between 275 and 300 g were used. 21 animals were subjected to lesions.

Each animal underwent laparotomy by abdominal incision after anaesthetic with a dilution of Ketamine, 100 mg/Kg and Xylazine 11 mg/Kg, prepared in sterile conditions and injected by the intramuscular route.

The liver was located and exposed; an abrasion was produced on the lower lobe by applying slight pressure with a sterile tampon until blood was drawn. After hemostasis of the injured surface, the laparotomy was closed with a size 3.0 silk suture. The animals were sacrificed after 7 to 21 days.

Adhesion was assessed according to the ease with which the adjacent surfaces (upper and lower) of the lobe could be separated by surgical pincers, on the basis of the following scale:

0 no adhesion—the two surfaces can be separated 1 slight—moderate adhesion, the surfaces can be separated by pulling them apart with pincers;

2 notable adhesion between the two surfaces, any attempt to separate them causes the tissues to tear;

In this animal model, adherences which scored 2 were considered clinically significant.

In this positive control group (adherence formation) 17 animals out of 21 (80.9%) presented the formation of adherence with a score of 2.

Study 2

This study illustrates the significant reduction in the formation of adherences when a gel made of cross-linked hyaluronic acid (ACP) is used or a gauze based on HYAFF 11 (benzyl ester of HA) is used alone or in combination with hemostatic SURGICEL™ and Heparin 50 IU/ml. The ACP gel was spread over the surface to be treated.

The surgical protocol described in Example 1 was used as an animal model to induce adhesion formation.

The significant reduction in adhesion formation between the two adjacent surfaces of the left lobe of the liver is illustrated in Table 1.

TABLE 1

| MATERIAL | NUMBER OF ANIMALS | % OF SIGNIFICANT ADHESIONS (score 2) |
| --- | --- | --- |
| HYAFF 11 woven tissue | 6 | 50% |
| HYAFF 11 woven tissue + SURGICEL ™ | 6 | 16% |
| HYAFF 11 woven tissue + SURGICEL ™ + heparin | 6 | 16% |
| HYAFF 11 woven tissue + heparin | 6 | 33% |
| HYAFF 11 membrane (20-mm thick) | 11 | 36% |
| HYAFF 11 non-woven tissue + SURGICEL ™ | 6 | 33% |
| ACP 5% | 24 | 20% |

It is evident that the use of these slowly biodependable biomaterials as an impermeable barrier to inflammatory cells between two adjacent surfaces reduces the formation of adhesions, as compared to 80.9% of adhesion observed in the control group described in Example 1.

Study 3

This example shows the high incidence of surgical adhesion formation observed in a model of surgical lesion induced on the abdominal wall in rat to establish as a positive control and to compare that with the preventive action of healthcare articles comprised of HA derivatives of the invention (HYAFF 11+a polypropylene mesh) in adherence formation.

A total of 24 animals (12 control, 12 test) underwent lesion.

Each animal underwent laparotomy by abdominal incision following anaesthesia with a dilution of Ketamine 100 mg/kg and Xylazine 11 mg/kg prepared in sterile conditions and injected by the intramuscular route.

The flap to the left of the incision was raised with two surgical pincers in order to expose the abdominal wall. An area of 1.5 cm×1.5 cm of the peritoneal surface was removed with surgical scissors until exudate appeared, without removing the muscle bundle. In the control group, it was necessary to stitch a polypropylene mesh (measuring twice the area of the lesion) with a size 6.0 bioabsorbable Vycil suture over the injured surface in order to guarantee the tensile resistance of the abdominal wall. Before applying the material, the injured surface had to undergo thorough hemostasis.

After sacrifice at 14 days, the intermediate time of the range cited in Example 1, adherence was assessed according to the following scale:

0 absence of adhesion;
1 slight adhesion with no vascularization, can easily be separated;
2 moderate adhesion with no vascularization, can be pulled apart manually;
3 firm adherence, opaque and vascularized, difficult to separate, requiring the use of a scalpel;
4 very firm adherence, thick, opaque and vascularized, can only be cut apart with surgical scissors, with consequent destruction of tissues.

Adherences with a score of >2 were considered significant.

In the positive control group (adherence formation) 12 animals out of 12 (100%) presented adherence formation with a score of >2; whereas there was a significant reduction in the incidence of adhesion formation between the abdominal wall and inner organs when utilizing the product of the invention, as shown in Table 2.

TABLE 2

| MATERIAL | NUMBER OF ANIMALS | % OF SIGNIFICANT ADHESIONS (score 2) |
| --- | --- | --- |
| HYAFF 11 + polypropylene mesh | 12 | 25% |
| Control − polypropylene mesh | 12 | 100% |

It is evident that the use of the said HYAFF 11 material of the invention as a barrier (impermeable to inflammatory cells) between an injured, inside surface (abdominal wall) and the adjacent organs, reduces the formation of adhesions, as compared to 100% of adhesions in the control group treated with only a polypropylene mesh.

Study 4

This study illustrates the ability of auto-crosslinked hyaluronic acid (ACP) in the form of a gel and used as a coating to reduce surgical adhesion formation, in a model of lesion induced in the blind intestine of rat.

This type of lesion induces the formation of adhesions when treated with saline washing and hemostasis alone after surgery, as reported hereafter.

As in Example 1, Sprague Dawley rats weighing 275–300 g were used. Each animal underwent laparotomy by abdominal incision after anaesthetic with a dilution of Ketamine, 100 mg/Kg and Xylazine 11 mg/Kg, prepared in sterile conditions and injected by the intramuscular route. The blind intestine was located and exposed. A thermal lesion was induced on the surface of the intestine with a solid body using a copper disc with a diameter of 1 cm connected to a soldering appliance electronically set at a temperature of 69.5° C. This was left in contact with the intestinal surface for 15 seconds. A well-defined lesion with exudate was produced. After washing the injured area with saline and performing hemostasis with SURGICEL™, the laparotomy was closed with a size 3.0 silk suture.

After sacrifice at 14 days, the intermediate time of the range cited in Example 1, adherence was assessed according to the following scale:

0 absence of adhesion;
1 slight adhesion with no vascularization, can easily be separated;
2 moderate adhesion with no vascularization, can be pulled apart manually;
3 firm adherence, opaque and vascularized, difficult to separate, requiring the use of a scalpel;
4 very firm adherence, thick, opaque and vascularized, can only be cut apart with surgical scissors, with consequent destruction of tissues.

In this animal model, adherences with a score of >2 were considered significant.

There is an evident reduction in the formation of adhesions when ACP gel is used as a barrier, as compared to the controls treated with saline washing and hemostasis alone (Table 3).

TABLE 3

| MATERIAL | NUMBER OF ANIMALS | % of SIGNIFICANT ADHESIONS (score 2) |
| --- | --- | --- |
| Control (saline + hemostasis) | 17 | 70% |
| ACP 5% | 11 | 40% |

It is evident that the use of said material as a barrier reduces the formation of adhesions, as compared with the control treatment of saline washing and hemostasis alone.
Study 5—Effect of Hyaluronic Acid Derivatives HYAFF-7 and HYAFF 11p75 in the Prevention of Postsurgical Adhesions in the Hepatic Lesion Model in Rat Animal Model:
Male, Harlan SD rat weighing 250 g.
Type of Lesion:
The abdominal area was thoroughly cleansed with an iodine solution, then a laparotomy of about 3 cm was performed to expose the liver. The lower right lobe of the liver was damaged by abrasion and a lesion produced with a sterile wooden spatula until blood was drawn.

Test Materials:
Experiment 1: HYAFF 11p75, 75% partial benzyl ester of hyaluronic acid in the form of a gauze and a nonwoven tissue.
Experiment 2: HYAFF 7, total ethyl ester of hyaluronic acid in the form of a gauze and a nonwoven tissue.
Application of the material: after careful hemostasis with a conventional hemostatic, the test and control materials were placed between the lower (lesion area) and the upper hepatic lobes (adjacent surfaces) without the use of suture so as to form a barrier effect and prevent the formation of adhesions.

Assessments and Observations:
Observations were made between seven and twenty-one days following surgery. The adhesions which had formed were assessed on the basis of the following visual score:
0=Absence of adhesions
1=Slight adhesions
2=Notable presence of adhesions
Besides assessment by the adhesion score, the degree of inflammation was assessed by microscopic observation (tissue reaction to application of the material), staining the histological samples with hematoxylin/eosin and Mallory's triple stain.

Figure 2:
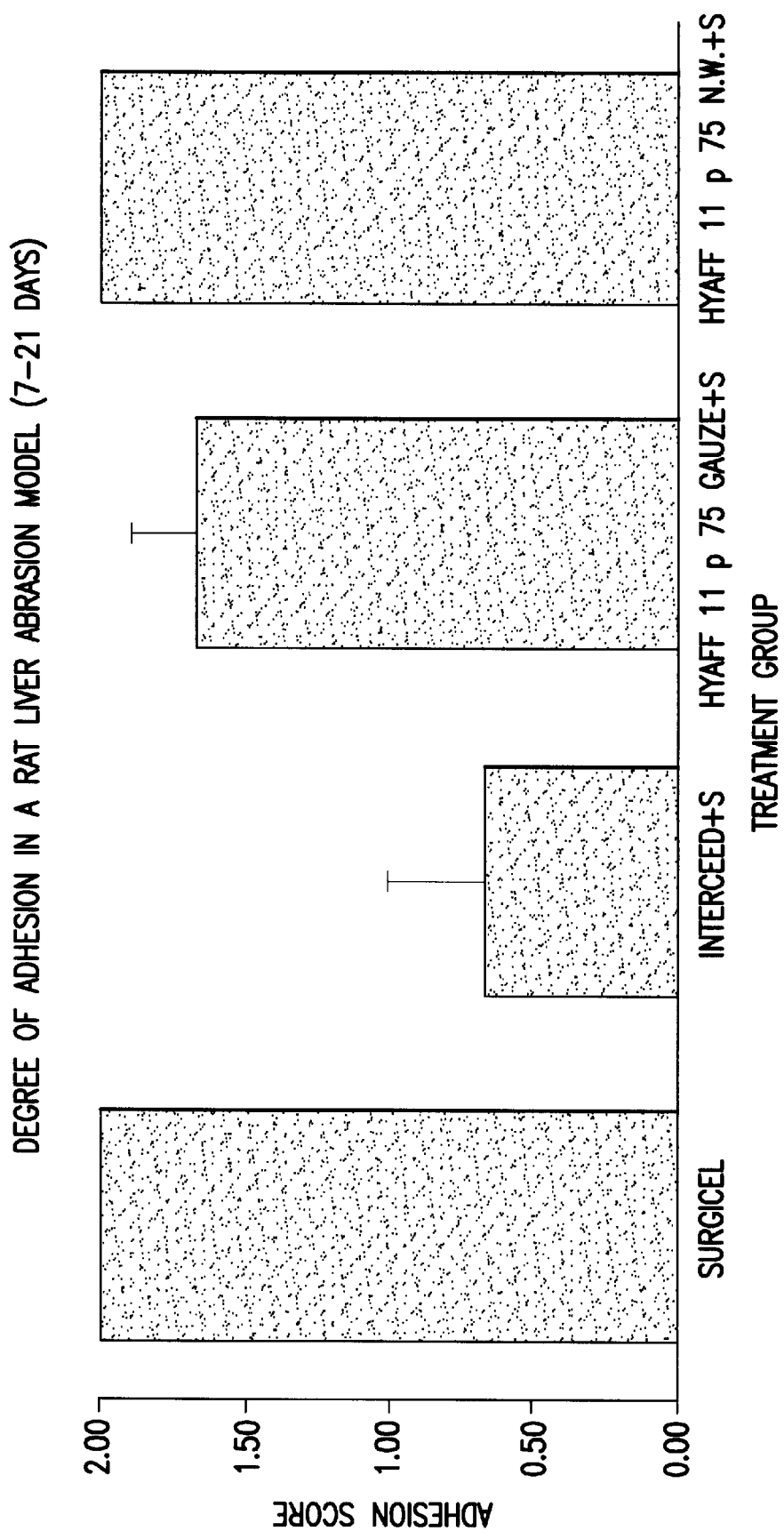
Figure 3:
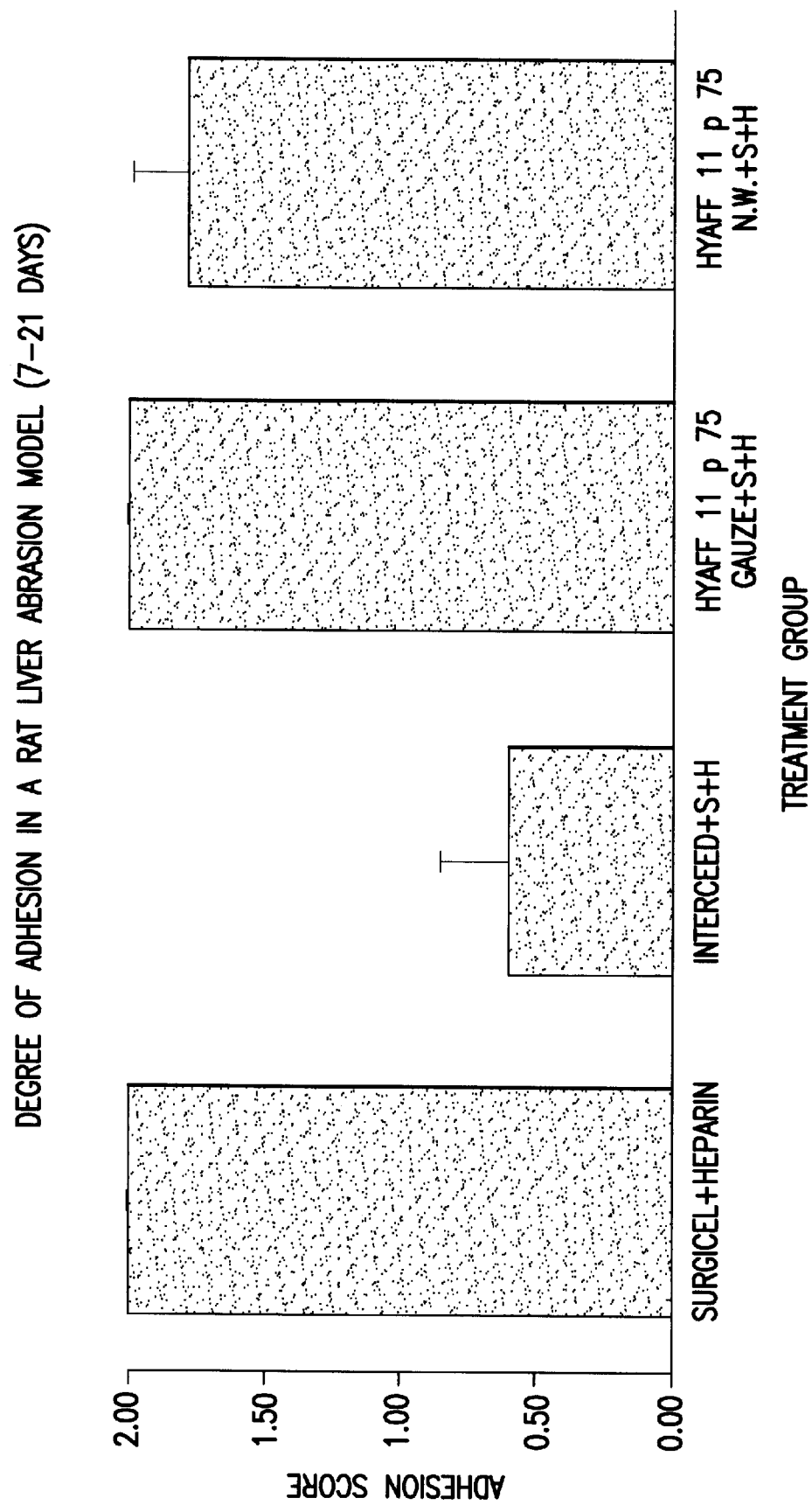

Results
Experiment 1:
In Experiment 1, the materials based on HYAFF 11p75, partial benzyl ester of hyaluronic acid, were tested alone, in combination with SURGICEL hemostatic and in combination with the hemostatic plus heparin saturation (1,000 Uml). These procedures are common practice in surgery.
FIG. 1 is a graph showing the performance of the biomaterials when used alone. No effect on adhesion prevention was observed in the case of the biomaterials based on HYAFF 11p75 and INTERCEED, and even though the trend did seem better, albeit not significantly different, in the latter case, the hepatic lobes were completely adhered and a significant inflammatory reaction could be seen. The same was observed on histological observation of the biopsies, where a notable presence of inflammatory cells, neutrophils and macrophages, and mature collagenous fibers could be seen.
In FIGS. 2 and 3 the materials were used in combination with SURGICEL and SURGICEL+heparin. The trend observed in FIG. 1 was confirmed by the materials based on HYAFF 11p75, while INTERCEED saturated with heparin seemed to give better effects. This situation was confirmed by the histological observations.
In conclusion, the materials based on HYAFF 11p75 cannot be used in the prevention of postsurgical adhesions, as the inflammatory effect is probably due to the release of oligomers of low-molecular-weight hyaluronic acid, in view of the extremely brief degradation times of the products.

Figure 4:
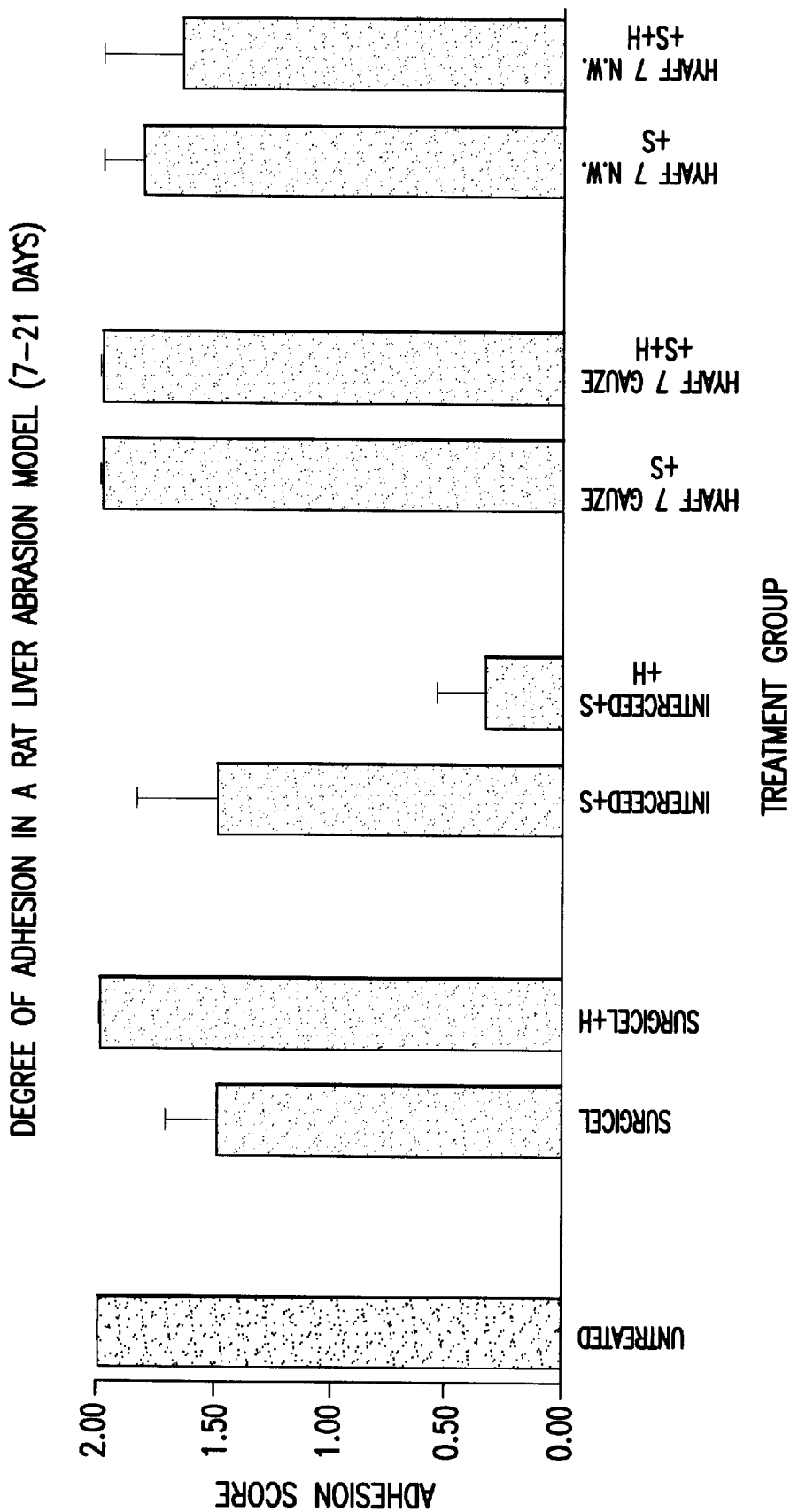

Experiment 2:
In Experiment 2, the biomaterials based on HYAFF 7, ethyl ester of hyaluronic acid, were tested in combination with SURGICEL and SURGICEL+heparin. In neither case was an effect on the prevention of postsurgical adhesions to be observed. INTERCEED used with SURGICEL+heparin seemed to have the more positive effect (FIG. 4).
Microscopic observation confirmed these data and revealed a notable quantity of inflammatory cells and collagen fibers in the case of treatment with HYAFF 7. In this case, as in the last, the biomaterials based on HYAFF 7 cannot be used in the prevention of postsurgical adhesions, as it is likely that there is a progressive release of ethanol into the organism.
Study 6—Efficacy of HYAFF 11-Based Biomaterials in the Prevention of Postsurgical Adhesions in Two Different Models of Lesion Induced in Animals: 1) Intrahepatic Abrasion in Rat; 2) Lesion of the Abdominal Wall in Rat Animal Model 1:
Once the abdominal area had been disinfected with iodine and ethanol, a medial incision was made to expose the liver.
In this animal model, the inner surface of the lower hepatic lobe was scraped until exudate began to emerge. The abrasion received careful hemostasis with TABOTAMP (Ethicon) and the material was left on the damaged surface without the aid of suture because of the product's highly mucoadhesive characteristics.
Two HYAFF 11-based products were tested, both commercial versions of a 20 μm thick, continuous membrane, called TRANSPROCESS and HYALOBARRIER 20. Macroscopic assessment was made 14 days after surgery using a score system described above to define the adhesions. A further assessment was made of the percentage of animals with adhesion score=2 (significant adhesion).

Figure 5:
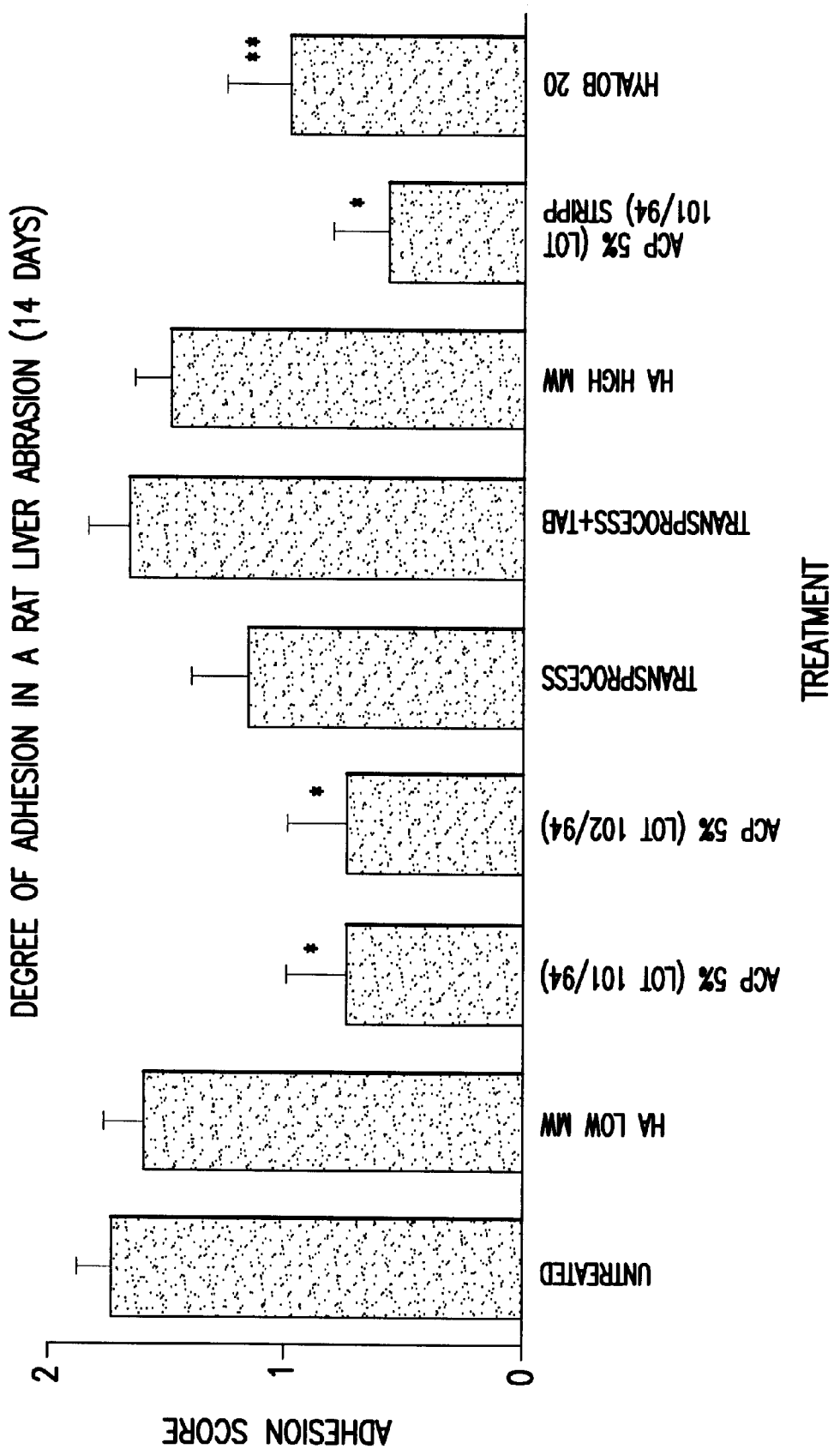
Figure 6:
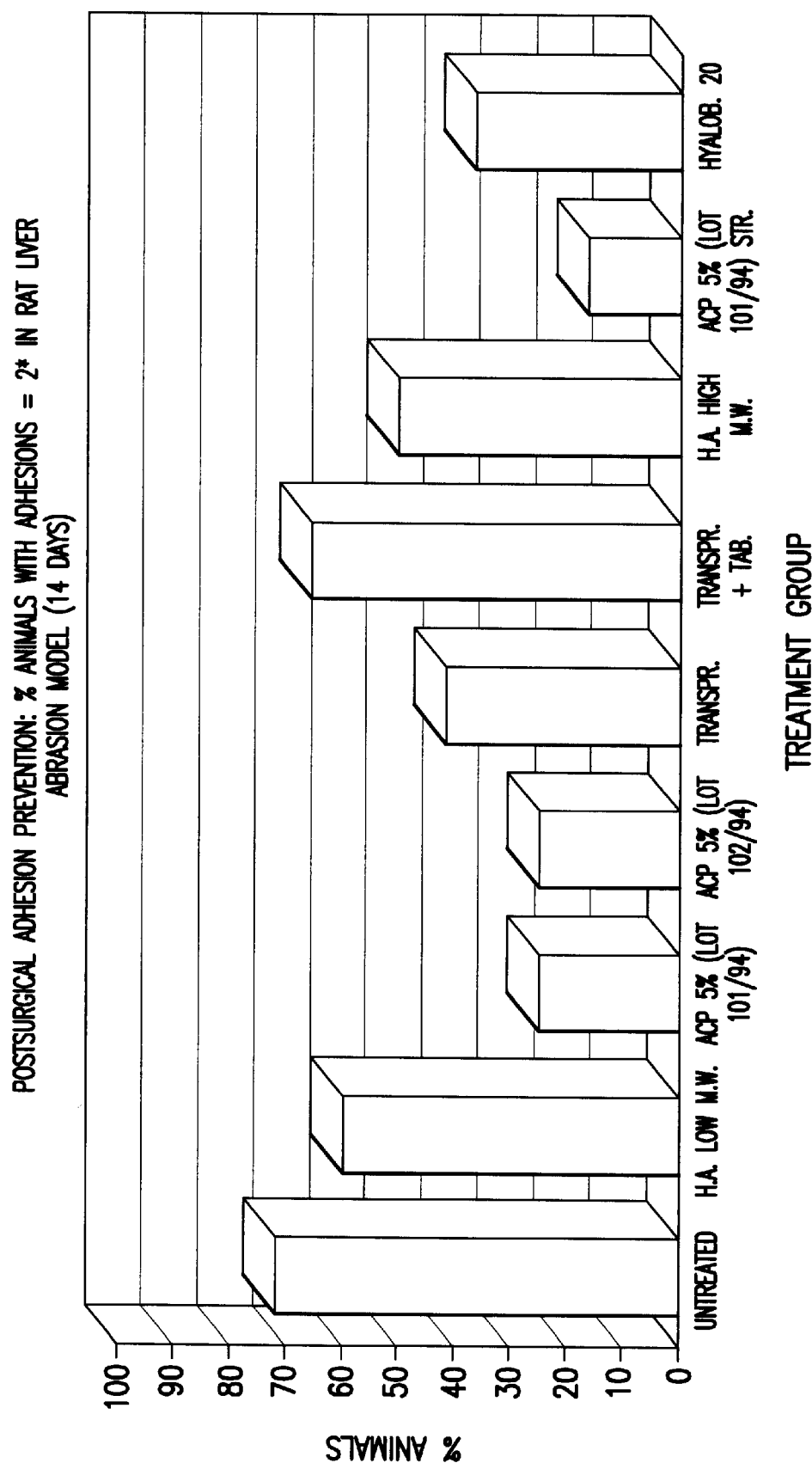

Results:
FIG. 5 is a graph representation of the adhesion scores obtained in the experiment. HYALOBARRIER 20 reduces the incidence of adhesion formation compared to the nontreated controls and to the two treatments with high- and low-molecular weight hyaluronic acid. A similar trend was recorded, albeit without any statistically significant differences, in the case of the other HYAFF 11-based material, Transprocess. FIG. 6 shows the percentages of cases of adhesion score=2 in each treatment group (surgically significant adhesion). The tendency revealed by the previous graph (FIG. 1) was confirmed in this case too, with a reduction in adhesion scores=2 (percentage of less than 50% for the HYALOBARRIER 20 and TRANSPROCESS treatments.

Animal Model 2:
Once the abdominal area had been disinfected with iodine and ethanol, a median laparotomy of about 5 cm in length was made to expose the abdominal wall and peritoneum.

An incision of 2 cm×2 cm was made with a scalpel and then the peritoneum and the muscular layer were removed. In this type of operation, it is necessary to suture to the damaged area a material which favors tissue growth while guaranteeing adequate tensile strength, in order to avoid the collapse of the peritoneal wall. Generally, nondegradable materials with a polymeric matrix are used, such as meshes of polypropylene, polyester or expanded polytetrafluoroethylene (e-PTFE). The use of such materials alone, however, is not sufficient to avoid the formation of adhesions to the intestinal loops, with consequent intestinal obstruction and chronic pain.

Macroscopic assessments were made 14 days after surgery by applying adhesion scores running from 0 to 4. A further assessment was made of the percentage of animals with an adhesion score of >2 (significant adhesions).

Figure 7:
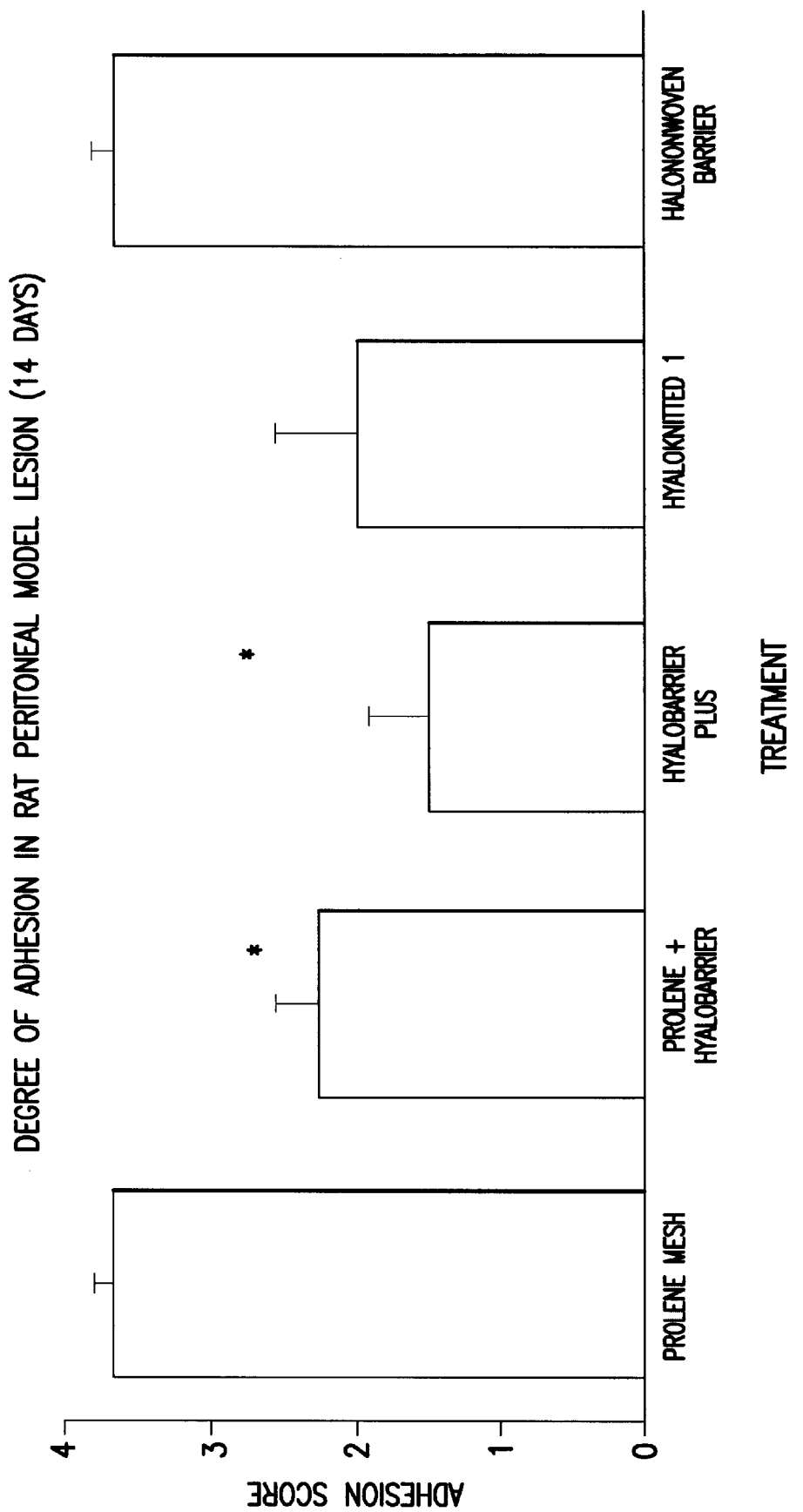
Figure 8:
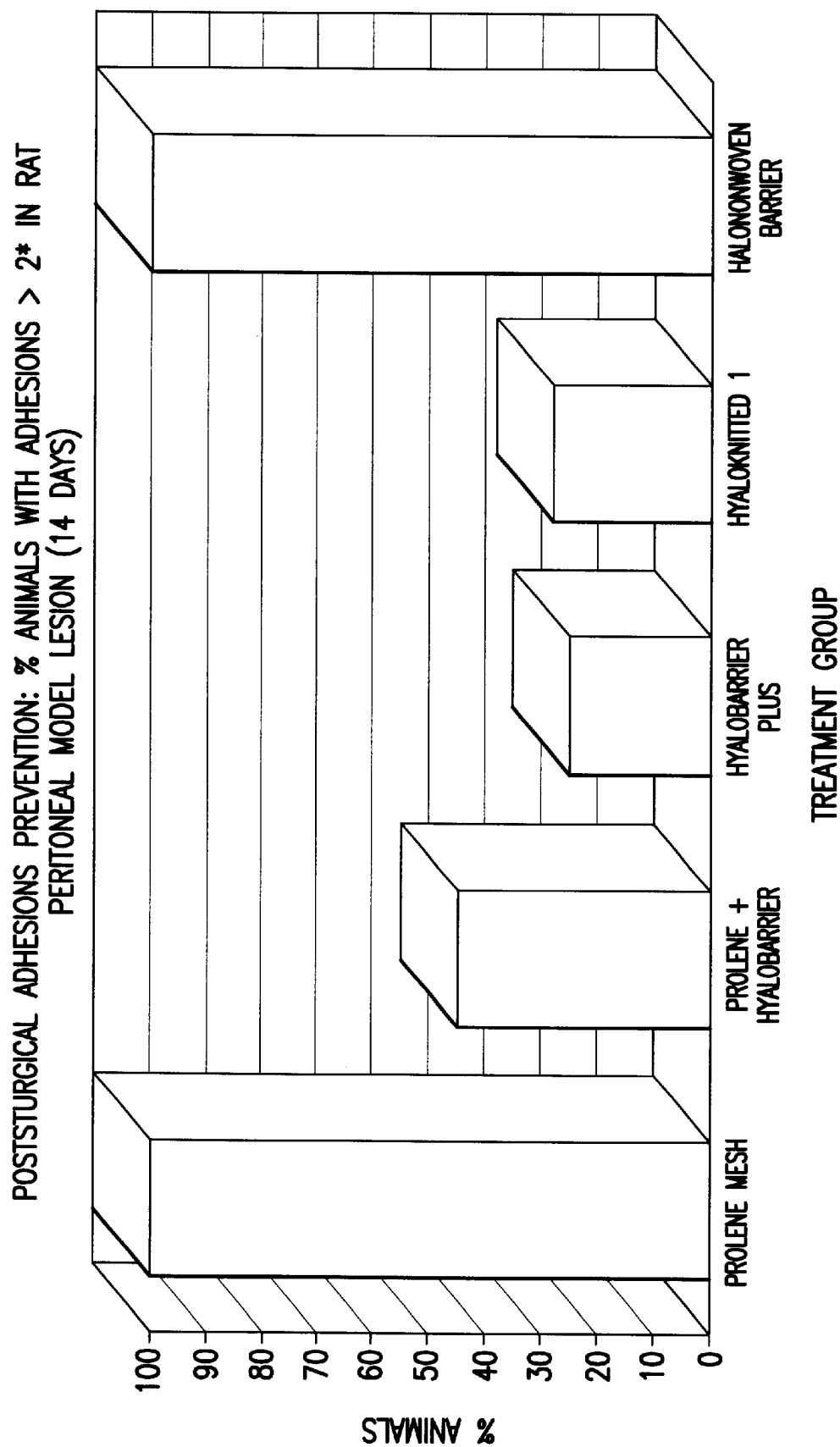

Results:

This experiment demonstrates that a coating of HYAFF 11 on a synthetic PROLENE mesh (polypropylene mesh, widely used in abdominal surgery) and a sheet of HYAFF 11 on a PROLENE mesh attached by suture can reduce the formation of postsurgical adhesions. FIG. 7 shows that the combined product called HYALOBARRIER Plus (HYAFF 11 spread and coagulated on PROLENE) and the HYALOBARRIER film suture on PROLENE significantly reduce adhesions compared to PROLENE mesh alone. FIG. 8 confirms this trend, with a lower percentage of adhesions >2 (significant adhesions) following treatment with HYAFF 11 than was observed after treatment with PROLENE mesh alone.

Study 7—Effects of ACP Gel Biomaterials on the Prevention of Postsurgical Adhesions Formation at 14 Days in a Rat Liver Injury Model and in a Rat Intestine Injury Model The purpose of this study was to evaluate the efficacy of ACP gel-based biomaterials, to reduce or prevent postoperative adhesions formation. The performances of the test materials were assessed in comparison to the hyaluronic acid high molecular weight and to the commercially available biomaterials, oxidized regenerated cellulose (TC 7 INTERCEED) used in abdominopelvic and gynecological surgery to prevent adhesion formation.

A rat liver lesion model and a rat intestine burn model were used since they are characterized models of experimental adhesion induction. The effects of the test and control materials on the prevention of postsurgical adhesion were evaluated by gross observation of the site of lesion applying an adhesion score.

A rat liver injury model (Experiment 1) and a rat intestine injury model (Experiment 2) were used since they are standardized and reproducible models of experimental adhesion induction. ACP based biomaterials were used after injury as a barrier between adjacent surfaces of the epatic lobe and internal organs.

In both experiments the efficacy of ACP gels was evaluated for their ability to prevent or reduce adhesion formation in comparison with TC7 INTERCEED, an absorbable oxidized cellulose adhesion barrier widely used in clinical practice, a copolymeric solution "THERMOGEL", a solution of high molecular weight hyaluronic acid and a group of untreated animals (sham operated).

Start Date:

Experiment 1—Rat Liver Abrasion

Tested Materials:

|  | 1 | 2 |
| --- | --- | --- |
| PRODUCT CODE | SMK 0002 | SMK 0002 |
| COMMON NAME | ACP Gel 5% | ACP Gel 5% |
| COMMERCIAL NAME | Hyalogel Barrier | Hyalogel Barrier |
| SUPPLIER | FAB | FAB |
| LOT NUMBER | 101/96 | 104/96 |
| EXPIRY DATE | 20 Feb. 1996 | 20 Feb. 1996 |
| STORAGE | below 30° C. | below 30° C. |
| PRECAUTIONS | none | none |

ACP gels were suspended in water at the concentration of 60 mg/ml. The test materials were supplied sterile by autoclave and in 5 ml syringe and manipulated in sterile conditions. The ACP gels were applied as to coat the abraded liver lobe surfaces after hemostasis with TABOTAMP®. Each animal received an amount sufficient to completely coat the injured area (about 2 ml) by single administration at time of surgery.

Control Materials:

|  | 1 | 2 | 3 |
| --- | --- | --- | --- |
| TRADE NAME | TC7 INTERCEED* | HYAL | THERMOGEL |
| MANUFACTURER/ SUPPLIER | Johnson & Johnson Patient Care, New Brunswick, NJ | FAB | BASF Pharma |
| DESCRIPTION | Oxidized regenerated cellulose barrier | Hyaluronic Acid (M.W. 800,000) | Pluronic Acid |
| LOT NUMBER | 2710TCM | 0108 st | 1/95 |
| EXPIRY DATE | November 1997 | May 1997 | — |
| STORAGE | below 30° | below 30 | below 8° C. |
| PRECAUTIONS | none | none |  |

INTERCEED was cut under sterile handling conditions, it was used alone and saturated in Heparin (500 U/ml), then applied so as to keep separated the two adjacent surfaces of the hepatic lobes to a size exceeding the borders of the injured area by several mm. HYAL, Hyaluronic Acid High Molecular Weight (solubilized in water at the concentration of 10 mg/ml) and THERMOGEL were purchase in sterile syringe.

INTERCEED was applied by direct application without surgical suture. HYAL and THERMOGEL were applied to the injured surface (coating) with a syringe after hemostasis. Each animal received an amount sufficient to completely coat or cover the injured area by single administration at time of surgery.

Experimental Design:

Sprague Dawley rats (275–300 g) were utilized for this experiment. From the experience gained from previous experiments, a period of 14 days was considered an adequate time point to evaluate adhesion formation in these animal models. Given the number of animals required for this study, animals were prepared on successive days.

A total number of 78 animals were used according to the following scheme:

| GROUP | TREATMENT | NUMBER OF ANIMALS |
|---|---|---|
| Sham Operated | Untreated | 12 |
| Controls | TC7 INTERCEED ™ Alone | 12 |
| Controls | TC7 INTERCEED ™ + Heparin | 6 |
| Controls | HYAL ® | 12 |
| Controls | THERMOGEL | 12 |
| Treated | ACP 5% (batch 101/96) | 12 |
| Treated | ACP 5% (batch 104/96) | 12 |

Preparation of the Animals:

Animals were anesthetized by i.m. Ketamine (Gellini Pharmaceutical)/Xylazine (Bayer) injection, shaved and then disinfected with iodine solution and ethanol. Following laparotomy on the left side, the left lobe of the liver was reflected upwards and the inner surfaces of the left and medial lobes of the liver were abraded by gentle rubbing with a wooden applicator until evidence of bleeding or serous exudate was obtained.

Administration of Materials:

After hemostasis obtained with SURGICEL® or TABOTAMP™, test and control materials were placed between the surfaces of the two lobes so as to cover the entire abraded area and to create a barrier between the lobes.

The surgical site was closed in two layers with 3.0 silk sutures.

At the end of surgery an antibiotic (Procacillina subcutaneous 30,000 I.U./rat) and an analgesic (Temgesic I.M. 0.05 mg/Kg) were administered for 4 days.

Adhesion Grade:

14 days after surgery, animals were euthanized by $CO_2$.

The adhesion grade was evaluated by gross observation. The following adhesion score was applied:

0=No adhesion

1=Low to moderate adhesion. The two epatic lobes were surgically separated by mechanical traction by forceps.

2=Marked adhesion, the two epatic lobes were completely sticked, any attempt to separation caused the breaking of the tissue.

The resorbability of the materials was evaluated by visual assessment of the presence of the materials; furthermore, the site of treatment was photographed.

After gross observations were made, the entire liver was surgically removed and placed in 10% buffered formalin for 48 hours. After fixation, a 2.0 mm cross-section including the abraded area, was removed from the liver by using a dissecting blade. The specimens so obtained were subjected to histological analysis.

Analysis of the Tissue

Histological Analysis:

Specimens were fixed in neutral buffered formalin 10% and subsequently dehydrated and embedded in paraffin by standard techniques; 8 $\mu$m section was stained with Masson's Trichnome (for tissue inflammatory reaction) and Toluidine Blue if necessary (for material remnants presence).

Experiment 2—Rat Intestine Burn

Tested Materials

| | 1 | 2 |
|---|---|---|
| PRODUCT CODE | SMK 0002 | SMK 0002 |
| COMMON NAME | ACP 5% High Mol. Weight | ACP 5% |
| COMMERCIAL NAME | Hyalogel Barrier | Hyalogel Barrier |
| SUPPLIER | FAB | FAB |
| LOT NUMBER | 3/94 | 101/94 |
| EXPIRY DATE | July 1995 | July 1995 |
| STORAGE | below 30° C. | below 30° C. |
| PRECAUTIONS | none | none |

ACP 5% gels High M.W. batch 3/94 was suspended in water at the concentration of 20 mg/ml, ACP 5% batch 101/94 was suspended at the concentration of 50 mg/ml. All the test materials were supplied sterile by autoclave and in 5 ml syringe and manipulated in sterile conditions. ACP gels were applied as to as to coat the burnt intestinal surfaces after hemostasis with TABOTAMP®. Each animal received an amount sufficient to completely coat the injured area (about 2 ml) in a single dose administration at time of surgery.

Control Materials:

| | 1 | 2 | 3 |
|---|---|---|---|
| TRADE NAME | TC7 INTERCEED* | HYAL | THERMOGEL |
| MANUFACTURER/ SUPPLIER | Johnson & Johnson Patient Care, New Brunswick, NJ | FAB | BASF Pharma |
| DESCRIPTION | Oxidized regenerated cellulose barrier | Hyaluronic Acid (M.W. 1,200,000) | Pluronic Acid |
| LOT NUMBER | 2710TCM | 0108 st | 1/94 |
| EXPIRY DATE | November 1997 | May 1997 | — |
| STORAGE | below 30° | below 30 | below 8° C. |
| PRECAUTIONS | none | none | |

INTERCEED was cut under sterile handling conditions, it was used alone and saturated in Heparin (500 U/ml), then applied so as to keep separated the two adjacent surfaces of the hepatic lobes to a size exceeding the borders of the injured area by several mm. HYAL, Hyaluronic Acid High Molecular Weight (solubilized in water at the concentration of 10 mg/ml) and THERMOGEL were applied in a sterile syringe.

INTERCEED was applied by direct application without surgical suture. HYAL and THERMOGEL were applied to the injured surface (coating) with a syringe after hemostasis. Each animal received an amount sufficient to completely coat or cover the injured area by single dose administration at time of surgery.

Experimental Design:

Sprague Dawley rats (275–300 g) were utilized for this experiment. From the experience gained from previous experiments, a period of 14 days was considered an adequate time point to evaluate adhesion formation in this animal model.

Given the number of animals required for this study, animals were prepared on successive days.

A total number of 59 animals were used according with the following scheme:

Experiment 2:

| GROUP | TREATMENT | NUMBER OF ANIMALS |
|---|---|---|
| Sham Operated | Untreated | 10 |
| Control | TC7 INTERCEED ™ | 6 |
| Control | Hyaluronic Acid (M.W. 1 200 000) | 12 |
| Control | THERMOGEL | 13 |
| Treated | ACP 5% (batch 101/94) | 12 |
| Treated | ACP 5% High Mol. weight (batch 3/94) | 6 |

Preparation of the Animals:

Animals were anaesthetized by i.m. Ketamine (Gellini Pharmaceutical)/Xylazine (Bayer) injection, shaved and then disinfected with iodine solution and ethanol. A midline abdominal incision was made through the skin and muscle tissue so as to expose the intestine. Burn was produced by application to the cecum surface of an electronically controlled heated copper disk (1 cm diameter) using a standard pressure for 15 sec. at 158° F. (69.3° C.).

Administration of Materials:

After hemostasis obtained with SURGICEL® or TABOTAMP™, test and control materials were placed on the intestine surface without suture so as to cover the entire burned area and to create a barrier between the peritoneum and internal organs.

The musculo peritoneal layer were closed with continuous 3-0 silk sutures, the cutaneous layer with skin staples and 3-0 silk interrupt suture.

At the end of surgery an antibiotic (Procacillina subcutaneous 30,000 I.U./rat) and an analgesic (Temgesic I.M. 0.05 mg/Kg) were administered for 4 days.

Observations and Determinations:

Adhesion Grade:

14 days after surgery, animals were euthanized by $C_O2$. The adhesion grade was evaluated by gross observation. The following adhesion score was applied:

0=No adhesion

1=Low, avascular, easily dissected

2=Moderate, avascular, continuous, manual dissected

3=Opaque, vascular, difficult to section requiring scalpel separation

4=Dense, opaque, vascular, dissected only with surgical scissors and tissue damage.

The resorbability of the materials was evaluated by visual assessment of the presence of the materials; furthermore, the site of treatment was photographed.

Results

Experiment 1:

One animal died during anaesthesia administration, the placement of the biomaterials was easily accomplished. The materials were noted to adhere to the tissue of the lower epatic lobe. No clinical signal of disease or suffering was noted after surgery in the treated animals with ACP.

Two animals treated with Hyaluronic Acid died two days after surgery. Necroscopic examination showed internal hemorrhage.

Figure 9:
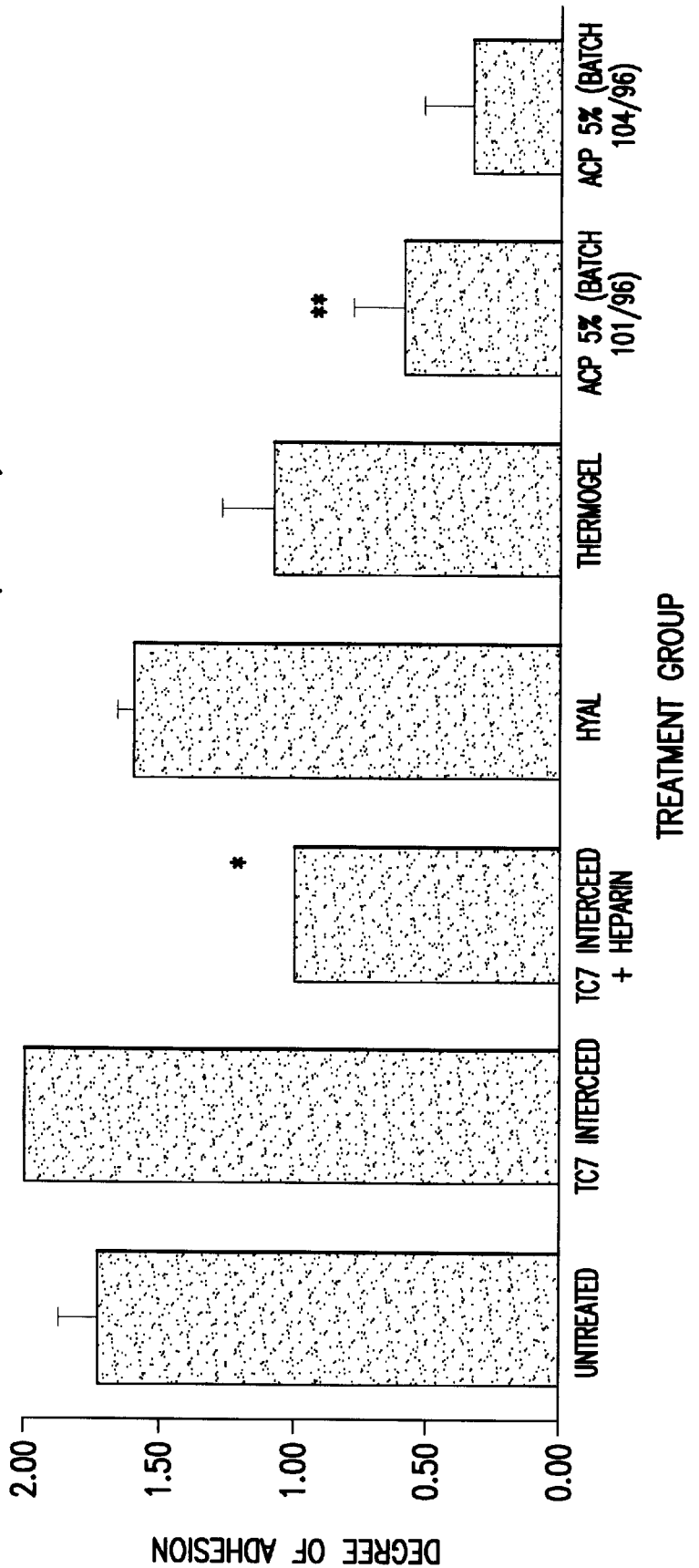

Evaluation of Adhesion Formation:

The adhesions formed between the two adjacent surfaces of the epatic lobe following tissue damage, were evaluated at 14 days. All treatments were degradated at the time of observation; the adhesion score (FIG. 9) in the animals treated with ACP 5% (batch 104/96) biomaterial was significantly lower than all control materials and untreated control. In the ACP 5% (batch 101/96) treatment, the reduction of adhesion was superior than TC 7 INTERCEED saturated with heparin but no statistical differences were noted; nevertheless both treatments showed significant differences ($p<0.05$) if compared to the controls and untreated.

Histomorphological Observation:

At microscopic examination, 14 days after surgery, the ACP treatments were found to be highly biocompatible and a very low inflammatory reaction was observed, in particular, few inflammatory cells, as neutrophils and giant cells, were present, no migration or enhancements of these cells inside the gap between the two lobes was noted, TC 7 INTERCEED showed tissue reaction consequently in many cases the epatic surfaces were partially sticked; the scope observation emphasized the presence of organized collagen fibrils, the inflammatory reaction seems to decrease if this treatment is saturated with heparin solution. In the majority of the slides the biomaterials appeared completely biodegradated. The untreated control gave moderate-high inflammatory reaction.

Experiment 2:

A total number of 2 animals died during anaesthesia administration, the placement of the biomaterials was easily accomplished and they did not move after placement. No clinical signal of disease or suffering was noted after surgery in the ACP treatment group animals.

Four animals treated with Hyaluronic Acid mol. weight $1.2\times10^6$ and three animals with THERMOGEL died between two and five days after surgery. Necroscopic examination showed internal hemorrhage in all animals.

Figure 10:
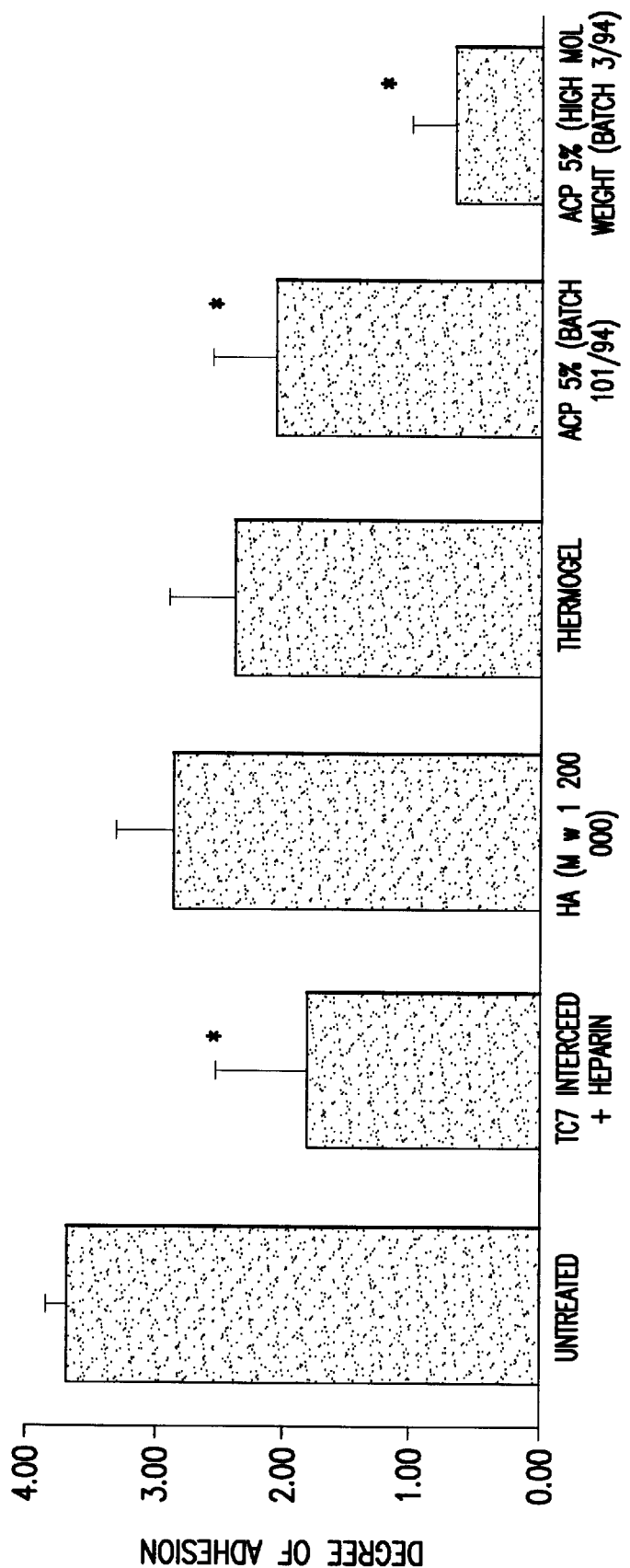

Evaluation of Adhesion Formation:

In this experiment, 14 days after surgery (FIG. 10), the ACP 5% gels (Lots 101/94 and 3/94), showed a reduction of postsurgical adhesion formations if compared to Hyaluronic Acid mol. weight $1.2\times10^6$ and untreated control, the performance of ACP gels was comparable to that of an INTERCEED Barrier, heparin saturated, statistical difference was found between these treatments and untreated control groups ($P<0.05$); all treatments and controls were completely absorbed.

Histomorphological Observation:

At scope observation at 14 days, the ACP treatments showed a low tissue inflammatory reaction, the thickness of granulation tissue was very low and no unfavorable reaction on the intestine as adhesion to the adjacent peritoneal surface were noted. The fibrils collagens begin to organize and healing process was completed. An inflammatory reaction was observed in hyaluronic acid treatments with considerable presence of collagen fibers that induce adhesion; a thick granulation tissue was seen. The same histomorphological appearance was noted in the untreated control.

Discussion:

Adhesions formation are among the leading cause of postoperative morbidity following abdominopelvic surgery, frequently leading to small bowel obstruction and other important pathologies. When the pelvic viscera are involved, these adhesions have the potential to impair physiologic function and result in infertility. The mechanism of postsurgical adhesion formation and reformation remain poorly understood. The experimental evidence suggest that adhesions form between two surgically traumatized surfaces in natural apposition during the healing process because it is more efficient to combine two site of tissue repair into a single healing site, resulting in coalescing adhesions between two adjacent surfaces.

In this screening, it was found that the use of a conventional surgical hemostatic agent (SURGICEL®) after surgery and the successive placement of a biodegradable hyaluronic acid derivative barrier, prevents the formation of adhesions. In addition, the materials may be used in conjunction with fibrinolytic agents. The adhesion reduction compared favorably with that of oxidized regenerated cellulose TC 7 INTERCEED*.

HYAFF® 11 biomaterials showed good biocompatibility and very low inflammation. The rate of degradation of the FAB biomaterials tested was different and depend from the different physical form of the treatment; HYAFF 11® biomaterials persisted several weeks. The range of controlled degradation rates which may be achieved with these Hyaluronic Acid derivatives may be usefully exploited for the prevention of postsurgical adhesions in different anatomical sites and applications, e.g. gynecological or abdominopelvic areas.

The results suggest that hyaluronic acid derivatives (HYAFF® 11 gauze and membranes) have a role in the prevention of adhesion formation following surgery.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Study 8—Effect of Different Batches of ACP Gel on the Prevention of Post Surgical Adhesions Formation in a Rat Liver Model The aim of the present study was to screen various batches of ACP gel to evaluate its effect in the postsurgical adhesions prevention. The performances of the test materials were assessed in comparison with TC7 Intercede.

Experimental Design:

Five batches of ACP gel were provided; information about biomaterials such as concentration, molecular weight of starting Hyaluronic Acid remained unknown to the operator until the Histological analysis (the last step of experiment) was completed. The physico-chemical characteristic of each batch (viscosity and pH) are reported in the successive scheme. Adhesion formation was evaluated after 14 days.

A total number of 96 animals were used according with following scheme:

| No | Group | Treatment | Number of animals | Batch Corresp ACP 200 | Viscosity (Pa*sec−1) (60 mg/ml) | pH |
|---|---|---|---|---|---|---|
| 1 | Sham operated | Untreated | 24 | | | |
| 2 | Control | TC 7 INTERCEED | 12 | | | |
| 3 | Treated | ACP gel — A | 12 | 106/95B | 277.8 | 5.2 |
| 4 | Treated | ACP gel — B | 12 | 105/95A | 38.1 | ND |
| 5 | Treated | ACP gel — C | 12 | 101/94s | 153.8 | 5.2 |
| 6 | Treated | ACP gel — D | 12 | 108/95s | 408 | 5.4 |
| 7 | Treated | ACP gel — E | 12 | 106/95A | 277 | 5.2 |

Each animal death was replaced.

Preparation of the Animals:

Animals were anesthetized by i.m. injection of a solution of Ketamine+Xylazime (4.5 mg,+0.8 mg/100 g of body weight), shaved and then disinfected with iodine solution and ethanol. Following laparotomy on the left side, the left lobe of the liver was reflected upwards and the inner surfaces of the left and medial lobes of the liver were abraded by gentle rubbing with a wooden applicator until evidence of bleeding or serous exudate was obtained.

Administration of Materials:

After hemostatis obtained with TABOTAMP, TC7 INTERCEED control material was placed between the surfaces of the two lobes so as to cover the entire abraded area and to create a barrier between the lobes. ACP gels were administered in a standard volume of 2 ml. The surgical site was closed in two layers with 3.0 silk sutures.

At the end of surgery an antibiotic (Procacillina Subcutaneous 30 000 I.U./rat) and an analgesic (Nefam, 0.02 ml/rat sub cutaneous corresponding to 0.4 mg) were administered for 4 days.

Observations and Determinations

Adhesion Grade:

At the termination of the experiment, animals were euthanized by $CO_2$. The adhesions formed were evaluated by gross observations according to the following adhesion score:

0=No adhesions

1=Low to moderate adhesions

2=Marked adhesions and tissue damage

The resorbability of the materials were evaluated by visual assessment of the presence of the materials and the site of treatment photographed.

After gross observations, the entire liver was surgically removed and placed in 10% buffered formalin for 48 hours. After fixation, a 2.0 mm cross section including the abraded area was removed from the liver by using a dissecting blade. The specimen so obtained was subjected to histological analysis.

Percent of Animals With Adhesion Grade=2:

An adjunctive evaluation of percentage of animals with adhesion grade=2, in each treatment group, was made.

Histological Analysis:

Specimens were fixed in neutral buffered formalin 10% and subsequently dehydrated and embedded in paraffin by standard techniques. An 8 $\mu$m section was stained with Ematoxilin/Eosin and Mallory's trichrome for evaluation of tissue inflammatory reaction and material remnants presence.

Results:

The placement of the biomaterials was easily accomplished and ACP gels did not move after placement. No clinical signal of disease or suffering were noted after surgery in the treated animals.

Gross Observation, Evaluation of Adhesions Formation:

At the time of evaluations (14 days after the application) all treatments and control substances were completely absorbed.

Adhesions formation: ACP 5% batch B and ACP 5% batch C gave the highest adhesion grade among the Hyaluronate derivatives, no differences statistically significant were noted in comparison to the untreated and TC7 INTERCEED controls.

The ACP 5% gels batches A and D, showed a remarkable reduction of postsurgical adhesions compared to TC7 INTERCEED and untreated control, statistical analysis showed significant differences ($P<0.05$).

The ACP gel batch E also showed a reduction of adhesions although statistically significant differences were noted only in comparison to TC7 INTERCEED treatment that gave the highest rate of adhesions.

Figure 11:
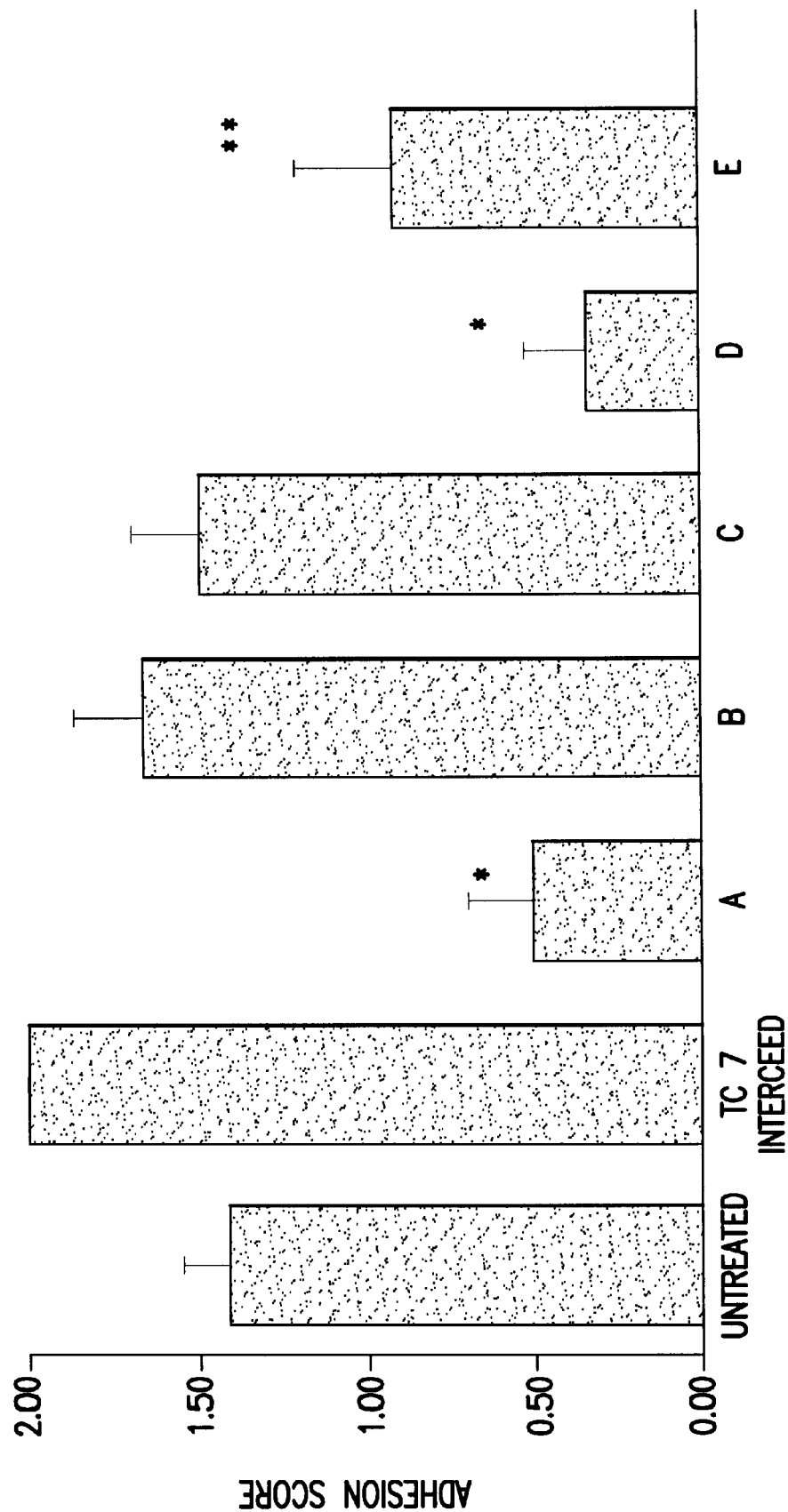

The results of the mean of adhesion score are summarized in the Table 4 and in FIG. 11.

Figure 12:
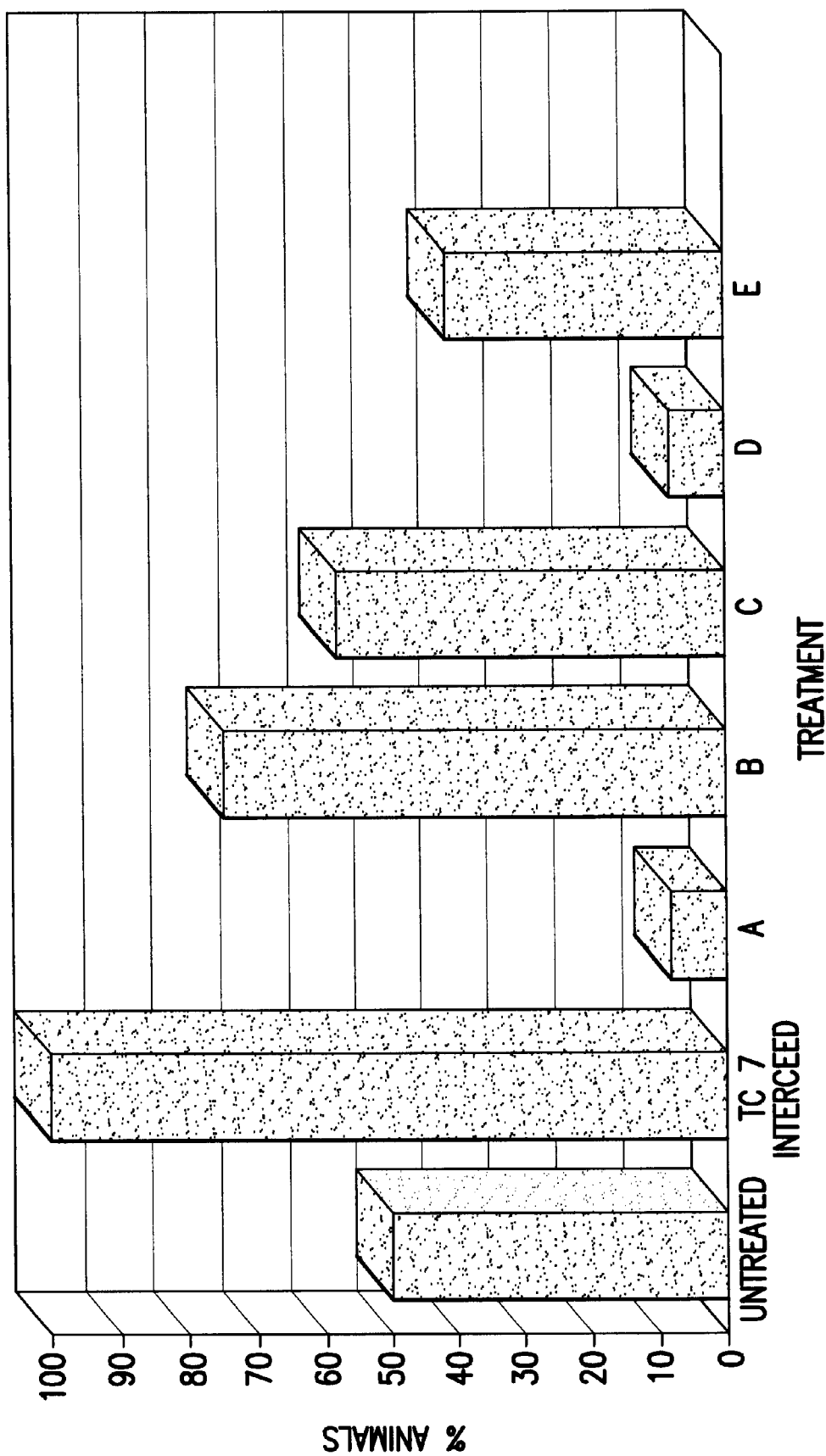

The percentage of animals with adhesion grade=2 in each treatment group was consistent with the data above: ACP batches A and batches D gave the lower percentage of adhesions grade=2 (8.33%) in comparison to ACP batch C (58.33%) untreated control (50%), and TC 7 INTERCEED (100%). The percentage of animals with significant adhesions is summarized in the Table 5 and FIG. 12.

Histomorphological Observation:

At microscope observation the ACP batches A and D showed the lowest tissue inflammatory reaction. In the majority of the samples the thickness of granulation tissue was very low and no unfavorable reaction was noted on the surface of the two hepatic lobes (lower and upper). The collagen fibrils began to organize and the healing process was completed. ACP batch E showed comprehensively moderate inflammatory tissue reaction whereas ACP batch B showed more remarkable tissue reaction. An inflammatory reaction associated with considerable presence of collagen fibers on the hepatic surface of the animals treated with TC7 INTERCEED. A low inflammatory reaction was noted to in the untreated control, however, the two hepatic lobes were completed attached.

Discussion:

Various batches of ACP gel, an internal ester of Hyaluronic Acid, with different physico-chemical properties were investigated in order to characterize a device able to prevent or reduce postsurgical adhesions. The data from this experiment performed in a rat liver lesion model, suggest that among different batches tested, two of them decreased the risk of postsurgical adhesions between two anatomical adjacent surfaces (hepatic lobes) and competed favorably with the control material used, TC7 INTERCEED and a group of untreated animals. Moreover, the two biomaterials shown good intercompatibility and a very low inflammatory tissue response.

TABLE 4

Degree of postsurgical adhesions in a rat liver abrasion model: mean ± standard error mean of adhesions score 14 days after surgery

| Treatment | No. of Animals | Mean ± Standard error mean of Adhesion Score |
| --- | --- | --- |
| Untreated (Sham Operated) | 24 | 1.42 ± 0.13 |
| TC 7 INTERCEED | 12 | 2.00 ± 0.00 |
| ACP gel — A | 12 | 0.50 ± 0.19* |
| ACP gel — B | 12 | 1.67 ± 0.19 |
| ACP gel — C | 12 | 1.50 ± 0.19 |
| ACP gel — D | 12 | 0.33 ± 0.19* |
| ACP gel — E | 12 | 0.92 ± 0.29** |

*$p < 0.05$ vs. untreated (Sham Operated) and TC7 INTERCEED
**$p < 0.0$ vs. TC7 INTERCEED (Mann-Whitney Rank sum Test)

TABLE 5

Percentage of animals per treatment group with grade of adhesion = 2 (significant adhesions) 14 days after surgery

| Treatment | No. of Animals | Mean ± Standard error mean of Adhesion Score |
| --- | --- | --- |
| Untreated (Sham Operated) | 24 | 50 |
| TC 7 INTERCEED | 12 | 100 |
| ACP gel — A | 12 | 8.33 |
| ACP gel — B | 12 | 75 |

TABLE 5-continued

Percentage of animals per treatment group with grade of adhesion = 2 (significant adhesions) 14 days after surgery

| Treatment | No. of Animals | Mean ± Standard error mean of Adhesion Score |
| --- | --- | --- |
| ACP gel — C | 12 | 58.33 |
| ACP gel — D | 12 | 8.33 |
| ACP gel — E | 12 | 41.66 |

Study 9—Use of a Synthetic Device in Combination With Hyaluronic Acid (HA) And its Derivative in the Repair of Abdominal Wall Defects Using a Rabbit Abdominal Wall Model of Surgical Defect.

The aim of the present study was to compare the efficacy of hyaluronan-plasma-coated- and hyaluronan derivative physically-coated-synthetic devices (e-PTFE and polyester parietal mesh, respectively) to the same unmodified devices for the prevention of postsurgical adhesions.

Incisional hernia and the repair of eventration are significant clinical problems in abdominal surgery, occurring in a high percentage of laparotomy incisions.

The use of a synthetic surgical mesh is one of many options available for the repair of congenital or acquired defects located in the abdominal wall. Unfortunately, the surgical application of synthetic devices is correlated, in a high percentage of cases, to the risk of post-surgical adhesions with the intestinal loops and the endo-abdominal organs, infections and foreign body reaction. Consequently the complications are: intestinal obstruction, chronic pelvic pain, intestine perforation and disorders of bowel movements.

Ideal prosthetic materials should have the following specific requirements: be non reactive, in order to limit any inflammatory response and other complications, assuring high tensile strength and absence of recurrence, limit adhesion formation.

The most frequently used prosthetic materials are various polypropylene meshes (MARLEX®, PROLENE®), polyester meshes (MERSILENE) and expanded Polytetrafluoroethylene. They offer a good tensile strength but few of them can be used in direct contact with the abdominal viscera.

The objective of this study was to evaluate, following surgical implant, possible differences in terms of adhesion prevention between two synthetic non-absorbable devices, e-PTFE and polyester parietal mesh, frequently used in the abdominal defect repair, and the same devices in combination with biodegradable materials such as hyaluronic acid and its derivatives.

The experiment was performed in a well standardized animal model, a rabbit abdominal wall defect. The materials were placed in direct contact with the visceral organs, hepatic organ and intestinal loops after removal of the omentum. With gross observations the presence of hyaluronic acid modulated the wound healing process with a complete regrowth of the mesothelial layer and reperitoneization of the synthetic component with absence of significant postsurgical adhesions.

Materials And Methods:

| NAME | e-PTFE + HA plasma coated | e-PTFE + HA plasma coated + HYAFF ® 11p80 extrusion |
|---|---|---|
| SUPPLIER | Gore/FAB | Gore/FAB |
| BATCH NUMBER | 11059-019 (Gore)-001/97 (Fab) | — |
| EXP. DATE | Jan. 10, 2002 | — |
| STORAGE | R. t° | — |
| STERILE BY | Steam | — |

| NAME | Polyester parietal mesh + HA plasma coated |
|---|---|
| SUPPLIER | Cogent/FAB |
| BATCH NUMBER | Experimental batch |
| EXP. DATE | — |
| STORAGE | R. t° |
| STERILE BY | Steam |

| NAME | e-PTFE | Polyester parietal mesh |
|---|---|---|
| SUPPLIER | GORE | Cogent — France |
| BATCH NUMBER | 11059-019 | Experiment batch |
| EXP. DATE | Jan. 10, 2002 | — |
| STORAGE | R. t | R. t |
| STERILE BY | Steam | Gamma ray |

The experimental materials were obtained by a HA plasma-coating process on e-PTFE and on polyester parietal mesh. The control material e-PTFE is a non-absorbable biomaterial while the polyester parietal mesh is a polyester non-absorbable mesh. Both devices are widely used in abdominal surgery.

Experimental Design and Surgical Technique:

A total number of 48 male New Zealand White rabbits, 3–4 months in age and 3 kg in weight, were randomly assigned in according to the following scheme:

| Group | Number of animals | Treatment | Dose |
|---|---|---|---|
| 1. Control | 12 | e-PTFE | 4.5 × 3.5 cm |
| 2. Control | 12 | polyester parietal mesh | 4.5 × 3.5 cm |
| 3. Treated | 12 | polyester parietal mesh + HA plasma-coated | 4.5 × 3.5 cm |
| 2. Treated | 12 | e-PTFE + HA plasma-coated | 4.5 × 3.5 cm |
| 3. Treated | 12 | e-PTFE + HA plasma-coated + HYAFF 11p80 film | 4.5 × 3.5 cm |

On the day of the surgical procedure, each rabbit was weighed and anesthetized by IM injection (4 ml) of a pre-mixed solution of Ketamine/Xylazine obtained mixing 10 ml of Ketamine (50 mg/ml) and 5 ml of Xylazine (20 mg/ml). Additionally an antibiotic, 5 mg/kg of enrofloxacin, was administered prophylactically.

The rabbits then were placed in supine position, shaved on the abdomino pelvic area, prepped with iodine solution and ethanol and draped in sterile fashion. A standardized surgical injury was performed according to the following steps:

1) Mid line laparotomy was performed beginning approximately 5 cm below the xiphoid process and continuing caudally for 5 cm.
2) After exposure of the peritoneum by means of an electrosurgical scalpel, both margins of the rectum abdominis muscle were removed for 1 cm. The result was a full thickness parietal defect approximately of 4×3 cm.
3) The omentum was totally removed and ligature was performed using DEXON II 3-0 suture (Davis Geck—American Cynamid Company, Wayne N.J., USA) with accurate hemostasis using a bipolar electrocoagulator.
4) The superior fascia of the rectum muscle was exposed and the muscular plane was isolated in order to fix the mesh.
5) e-PTFE and e-PTFE plasma-coated were sutured by 2-0 non-absorbable mono-filament GORE-TEX® suture. Polyester parietal mesh and polyester parietal mesh plasma-coated were sutured by 3-0 non-absorbable polyester suture. The superior side of the epoxy e-PTFE and the polyester parietal meshes were fixed to the xiphoid process and then sutured above the fascial plane by continuous suture.
6) The superficial muscular fascia was closed by continuous bioabsorbable suture (DEXON II 3-0 suture).
7) The skin layer was closed using continuous silk 3-0 suture (Ethicon).

At the end of surgery the external suture line was disinfected with betadine, and an analgesic (Nefopam 0.8 mg/kg) was administered to each animal, and a buster dog collar was applied in order to prevent bites along the suture line.

Observations and Determinations

Assessment of Adhesions:

Two months after the procedure, animals was euthanized with $CO_2$ asphyxiation, a laparotomy was performed and in the, surgical area of implant the following gross observations were made: evaluation of the device'stability, possible retraction, presence of adverse events (seroma, flogosis, inflammatory reaction) adhesion grade.

The adhesion grade was blindly evaluated according to the following scoring system:

| DESCRIPTION | | SCORE |
|---|---|---|
| EXTENT | NO INVOLVEMENT | 0 |
| | <25% SITE INVOLVED | 1 |
| | <50% SITE INVOLVED | 2 |
| | <75% SITE INVOLVED | 3 |
| | <100% SITE INVOLVED | 4 |
| TYPE | NONE | 0 |
| | FILMY, TRANSPARENT, AVASCULAR | 1 |
| | OPAQUE, TRANSLUCENT, AVASCULAR | 2 |
| | OPAQUE, CAPILLARIES PRESENT | 3 |
| | OPAQUE, LARGER VESSELS PRESENT | 4 |
| TENACITY | NONE | 0 |
| | ADHESION FALL APART | 1 |
| | ADHESION LYSED WITH TRACTION | 2 |
| | ADHESION REQUIRE SHARP DISSECTION | 3 |
| TOTAL POSSIBLE | | 11 |

At the end of the macroscopic observations, the surgical area was completely removed and fixed in 10% formalin. Successively three different biopsies deriving from superior, central, and inferior areas, including device and peritoneum, were taken and stained with Hematoxylin and Eosin and Mallory's trichrome. Histological analysis was performed to evaluate: giant cellular reaction, fibrosis, granulation tissue, and granulomatosis according to a 0 to 3 qualitative scale.

Statistical Methods:

A statistical analysis was applied using the Kruskal Wallis non-parametric Test for adhesion and histologic scores to compare treatment and control groups.

Significant differences were considered at $P<0.05$. Results are expressed as means±sem.

Results:

Three animals with e-PTFE+Plasma HA treated devices showed complications 20–40 days following surgery. They presented intestinal hernia through the muscular fascia incision due to breaking of suture resulting in two cases in slight necrosis. In two of these animals absence no further abnormality was detected in the abdomen or the thorax whereas one animal presented peritonitis due to infection during surgical procedure.

At the time of second look laparotomy all devices were incorporated in the newly-grown mesotelial layer, no evidence of seroma or subcutaneous abscess were present.

The Hyaluronan plasma-coated e-PTFE treatment group showed the lowest incidence of postsurgical adhesions. Only one animal showed a filmy and avascular adhesion between abdominal wall and intestinal loops. No adhesions were seen with the liver and no adhesions were seen in the remaining 11 animals. The resulting total adhesion score was 0.33±0.33.

Four animals (33%) of the e-PFTE control group developed clinically significant adhesions between. abdominal wall and the liver or intestinal loops. No adhesions were seen in the remaining 8 animals, with a total score of 3.00±1.31.

The Hyaluronan plasma-coated polyester parietal mesh showed a low to moderate incidence of adhesions (33% of the total animals). The resulting total adhesion score was 2.50±1.08 with significant differences ($p<0.05$) in comparison to the uncoated polyester parietal mesh control group that showed 66.6% of incidence with a total score of 6.25±1.39.

Figure 13:
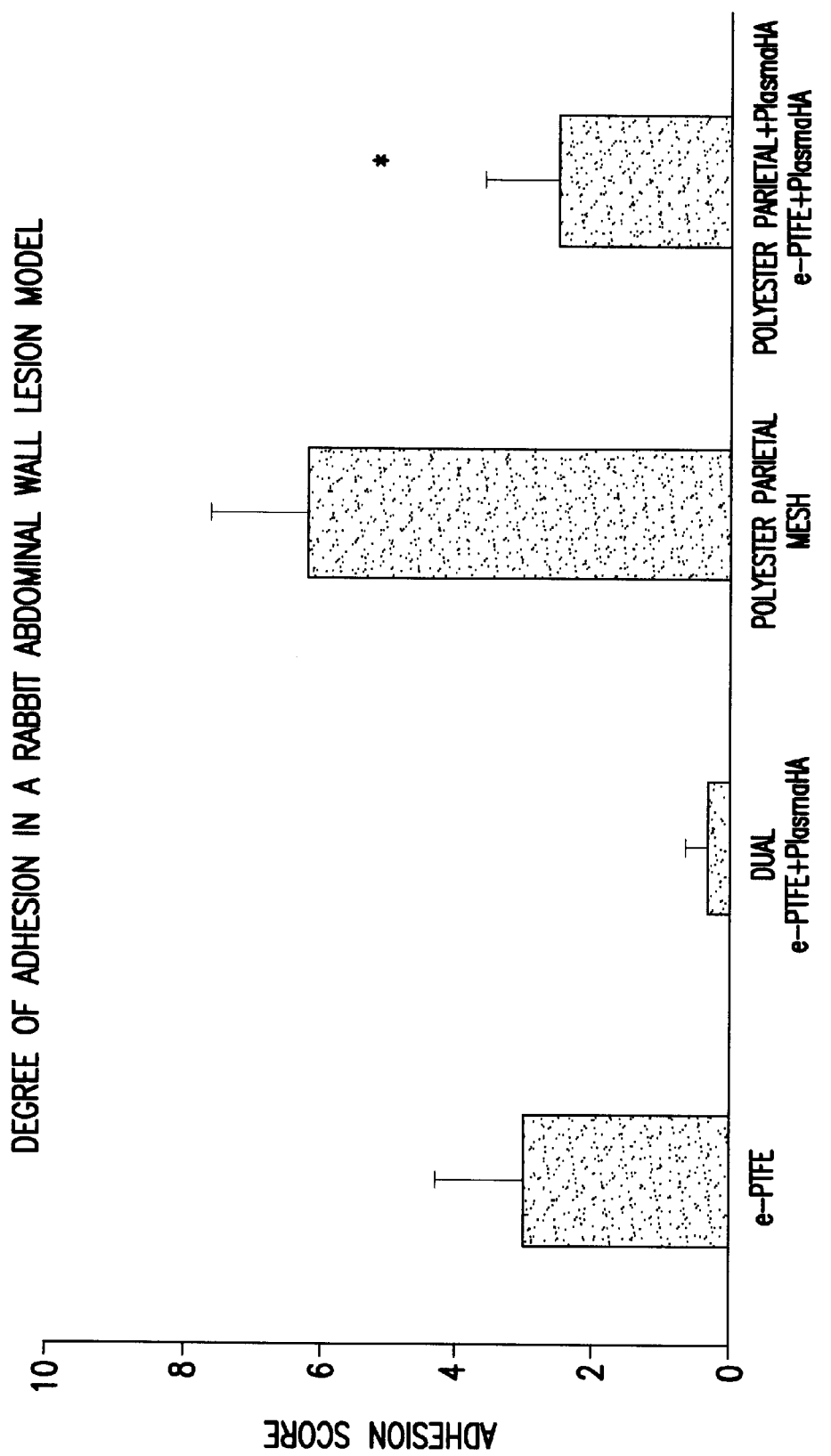

Data are summarized in Table 6 and FIG. 13.

Discussion:

An ideal synthetic prosthetic material for use in abdomino-pelvic surgery i.e. in large hernia repair should allow for particular features: maximal tissue incorporation while assuring high tensile strength, modulation of inflammatory tissue reaction and reduction of the incidence of severe intraperitoneal adhesions associated with bowel obstruction. Synthetic prosthesis are widely used in this kind of surgery i.e. polyester or polypropylene meshes, but few of them seem to be able to reduce the formation of adhesions. e-PTFE meshes are gaining popularity because of an apparent associated reduction in tissue reactivity and consequently adhesion formation. Many reports resulting from preclinical trial have demonstrated that e-PTFE devices resulted in fewer adhesions to underlying organs when compared to polyester and polypropylene meshes.

These experiments demonstrate that combinations of a e-PTFE biomaterial with a degradable biopolymer (Hyaluronan and its derivatives) produced by plasma-coating can further decrease the risk of adhesions. Additionally an open mesh, polyester parietal mesh, treated with Hyaluronic Acid plasma-coating can significantly reduce the incidence of postsurgical adhesions.

TABLE 6

| No Animal | Treatment | Extent | Type | Tenacity | Total Score |
|---|---|---|---|---|---|
| 1 | e-PTFE | 0 | 0 | 0 | 0 |
| 2 |  | 0 | 0 | 0 | 0 |
| 3 |  | 3 | 4 | 3 | 10 |
| 4 |  | 0 | 0 | 0 | 0 |
| 10 |  | 2 | 3 | 3 | 8 |
| 11 |  | 4 | 4 | 3 | 11 |
| 18 |  | 0 | 0 | 0 | 0 |
| 19 |  | 0 | 0 | 0 | 0 |
| 23 |  | 0 | 0 | 0 | 0 |
| 24 |  | 0 | 0 | 0 | 0 |
| 26 |  | 2 | 3 | 2 | 7 |
| 27 |  | 0 | 0 | 0 | 0 |
| Mean |  | 0.92 | 1.17 | 0.92 | 3.00 |
| sem |  | 0.42 | 0.51 | 0.40 | 1.31 |
| 7 | e-PTFE | 1 | 1 | 2 | 4 |
| 8 | plasmaHA | 0 | 0 | 0 | 0 |
| 9 |  | 0 | 0 | 0 | 0 |
| 12 |  | 0 | 0 | 0 | 0 |
| 13 |  | 0 | 0 | 0 | 0 |
| 25 |  | 0 | 0 | 0 | 0 |
| 31 |  | 0 | 0 | 0 | 0 |
| 32 |  | 0 | 0 | 0 | 0 |
| 33 |  | 0 | 0 | 0 | 0 |
| 34 |  | 0 | 0 | 0 | 0 |
| 37 |  | 0 | 0 | 0 | 0 |
| 38 |  | 0 | 0 | 0 | 0 |
| Mean |  | 0.08 | 0.08 | 0.17 | 0.33 |
| sem |  | 0.08 | 0.08 | 0.17 | 0.33 |
| 5 | polyester | 0 | 0 | 0 | 0 |
| 6 | parietal mesh | 0 | 0 | 0 | 0 |
| 14 |  | 3 | 4 | 3 | 10 |
| 15 |  | 4 | 3 | 3 | 10 |
| 16 |  | 1 | 4 | 3 | 8 |
| 17 |  | 0 | 0 | 0 | 0 |
| 20 |  | 2 | 2 | 3 | 7 |
| 21 |  | 4 | 4 | 3 | 11 |
| 22 |  | 4 | 4 | 3 | 11 |
| 28 |  | 0 | 0 | 0 | 0 |
| 29 |  | 1 | 3 | 3 | 7 |
| 30 |  | 4 | 4 | 3 | 11 |
| Mean |  | 1.92 | 2.33 | 2.00 | 6.25 |
| sem |  | 0.51 | 0.53 | 0.43 | 1.39 |
| 35 | polyester | 1 | 3 | 2 | 6 |
| 36 | parietal mesh | 2 | 3 | 3 | 8 |
| 39 | plasmaHA | 0 | 0 | 0 | 0 |
| 40 |  | 0 | 0 | 0 | 0 |
| 41 |  | 2 | 3 | 3 | 8 |
| 42 |  | 2 | 3 | 0 | 8 |
| 43 |  | 0 | 0 | 0 | 0 |
| 44 |  | 0 | 0 | 0 | 0 |
| 45 |  | 0 | 0 | 0 | 0 |
| 46 |  | 0 | 0 | 0 | 0 |
| 47 |  | 0 | 0 | 0 | 0 |
| 48 |  | 0 | 0 | 0 | 0 |
| Mean |  | 0.58 | 1.00 | 0.92 | 2.50* |
| sem |  | 0.26 | 0.43 | 0.40 | 1.08 |

*$p < 0.05$ vs. Parietex. Kruskal Wallis non-parametric Test

Study 10—Evaluation of the Clinical Performance and Safety of HYAFF 11p80-F and HYAFF 11p80-NW an HA Based Sinus Liner, in Edoscopic Surgery of Paranasal Sinuses Endoscopic sinus surgery has rapidly evolved over the last decade as the preferred method of surgical treatment for chronic sinus disease. Endoscopic sinus surgery involves the removal of diseased mucosal lining and polyps in the osteal meatal complex. The intent of this minimally invasive technique is to re-establish ventilation in the sinuses and restore a healthy mucosal lining. The leading post operative complication of sinus surgery is post operative adhesion formation in the sinuses, especially in the middle meatal area. When adhesion formation occurs post operatively, the sinus ostia is once again blocked and chronic infection is likely to re-occur. The acceleration of healing in the surgical area should reduce the formation of adhesions.

The primary objective of the study was to evaluate whether a film of the 80% benzyl ester of HA (HYAFF 11p80-F) and a non-woven fabric of the 80% benzyl ester of HA (HYAFF 11p80-NW) in predetermined forms used in the ethmoidectomy site (sinus mucosa) subsequent to endoscopic sinus surgery is effective in decreasing adhesion formation and reducing time of healing in the sinus mucosa.

Secondary objective was to evaluate the safety of HYAFF 11p80-F and HYAFF 11p80-NW.

Experimental Design:

The study was an open, controlled, randomized, monocentre study. Fifteen patients subjected to endoscopic sinus surgery were enrolled. The patients were randomized to three groups:

A) patients treated with HYAFF 11p80-F and standard post-operative care;
B) patients treated with HYAFF 11p80-NW and standard post-operative care; and
C) patients treated with only post-operative care (control group).

Patients Selection Criteria:

The patients were enrolled, after written informed consent, according to the following admission criteria:

A) Inclusion Criteria

1) Diagnosis of chronic sinusitis with or without unilateral or bilateral polyposis, following a coronal CT scan of paranasal sinuses, which required functional endoscopic surgery.
2) Adequate medical treatment including antibiotics, nasal steroids, nasal decongestants, mucolytics for one or all of these conditions; nasal obstruction and stuffiness, rhinorrhea, postnasal drainage, facial pains.
3) Patients over 18 years of age.
4) Patient's written informed consent obtained.

B) Exclusion Criteria

1) Previous surgery on sinuses
2) Mycotic sinusitis
3) History of facial trauma
4) Known history of poor compliance with medical treatment
5) Patients suffering from immunodeficiency
6) Patients suffering from diabetes
7) Patients suffering from cystic fibrosis
8) Patients suffering from bronchial asthma
9) Patients suffering from asthma, nasal polyposis and aspirin allergy
10) Pregnancy
11) Patients with diagnosed cancer Additionally, patients were considered drop outs in the occurrence of one of the following situations:

1) Systemic administration of antibiotic and/or cortisonic therapy up to one week from operation.
2) Patients that had the middle turbinate totally removed during the operation.
3) Patients that had septoplasty or rhinoplasty done at the same time as the operation.

C) Drop-out

Patients were able drop out at their own request or at the discretion of the Investigator for violations to the study protocol, adverse events, poor compliance of the patient, lack of response to the experimental treatment, etc.

Additionally, patients who did not return at two consecutive control visits were excluded from the study.

Drop-out patients were not being replaced.

Surgical, Experimental and Control Procedure:

The surgery technique used in the study is the Functional Endoscopic Sinus Surgery (ESS) without total removal of middle turbinate. After the ESS procedure, patients randomized into the experimental group were treated with HYAFF 11p80-F and HYAFF 11p80-NW as appropriate by having the sinus liner placed over the areas of denuded bone and/or where the musosal lining had been substantially disturbed by disease and/or surgery. This was only performed after irrigation of the post-surgical site. Patients who had previous sinus surgery were not included in this study.

End Points for the Evaluation of Performance:

At each control visit, the following were assessed:

a) Post-operative Evaluation

The presence or absence and the percentage (if present) of adhesion and crusting; residual presence of the experimental material.

b) Procedures Done During Visit

Removal of adhesions, crusts, blood clots, if present; and extensive lavage.

c) Photograph of the Surgical Site

A photograph of the surgical site was taken in order to determine the healing patterns of each patient. The surgeon was asked to rank the observations to a provided numeric scale ranging from 0 to 5.

d) Patient's Comment on Quality of Healing

A subjective assessment of the quality of healing was requested from the patient. The patient gave an assessment on quality of healing by referring to symptoms such as facial pain, rhinorrhea, etc. This assessment was required at the preoperative visit, 4°, 5° and 6° control.

After surgery, the patient was requested to return for the control visits at 1, 8, 22, 50, 110 and 200 days. At the end of the follow up period, a global clinical assessment for performance of the device under investigation was requested from the Investigator.

All data analysis was performed using the SAS software (SAS Institute, Cary, N.C.).

Results

Patient Population:

A total of 15 patients were enrolled. The age of the patients (13 males and 2 females) averaged 14.36 years (sd=16.64 years).

Safety of HYAFF 11p80-F and -NW:

No severe adverse events occurred in the 15 patients enrolled in the study. No adverse event was recorded in the experimental group, or in the control group. Furthermore, no post-operative complications were recorded during the study.

Table 7 reports the clinician's comments on the safety of the devices under investigation. In the case of HYAFF 11p80-F and HYAFF 11p80-NW, tolerability was rated very good in the totality of the patients treated (i.e., 3/3 for HYAFF 11p80-F and 6/6 for HYAFF 11p80-NW).

Figure 14:
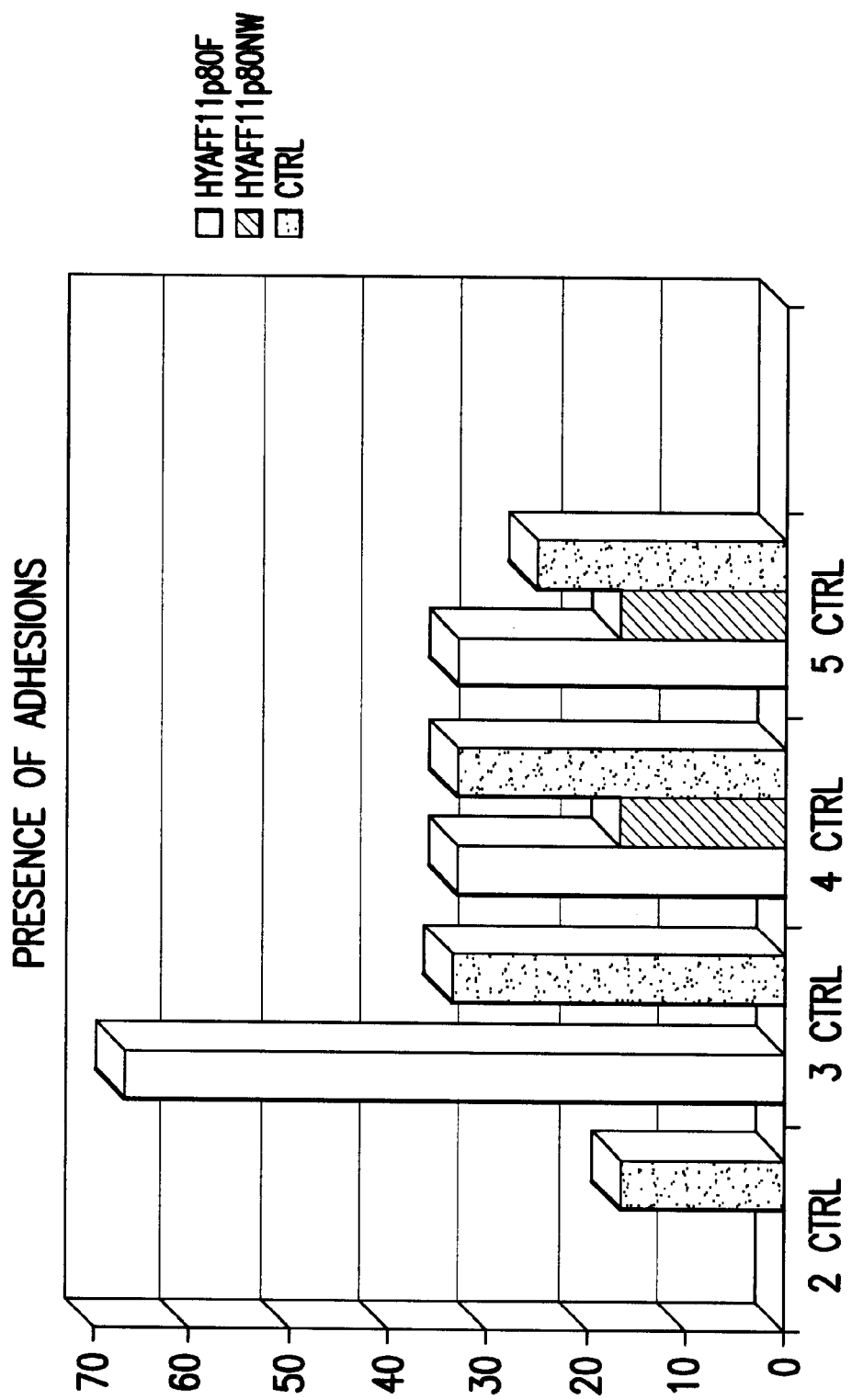

Post-Operative Evaluation:

The presence of adhesions in the three groups is recorded in FIG. 14. Throughout the study, patients treated with HYAFF 11p80-NW had either no adhesions (as in the first 2 control visits) or had less adhesions with respect to the other treatment groups. At the third control visit, 100% of the HYAFF 11p80-NW treated patients were free from adhesions, while 33% of patients in Group A (HYAFF 11p80-F) and 66.7% of patients in group C (control) were free from adhesions.

Figure 15:
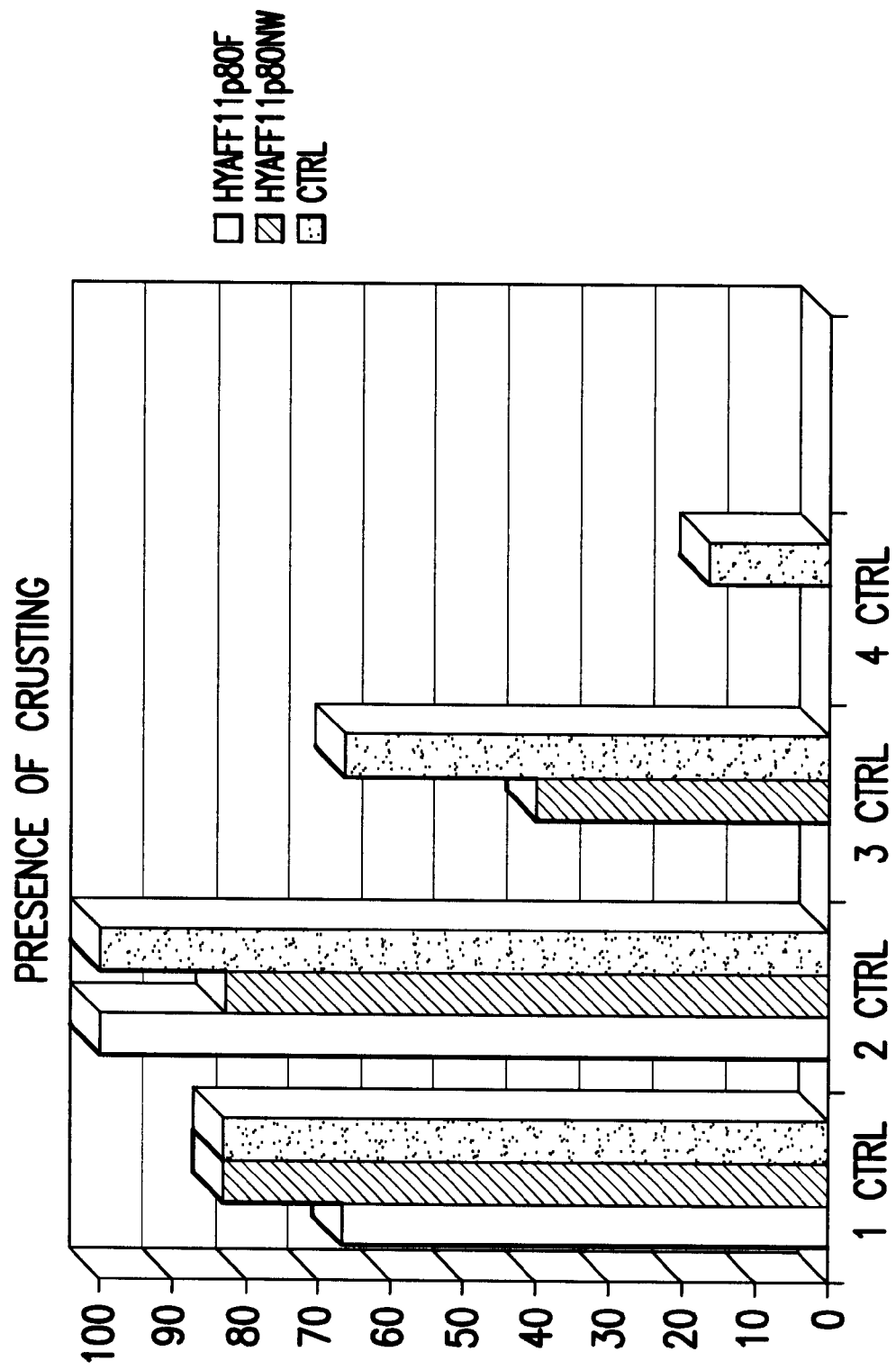
Figure 16:
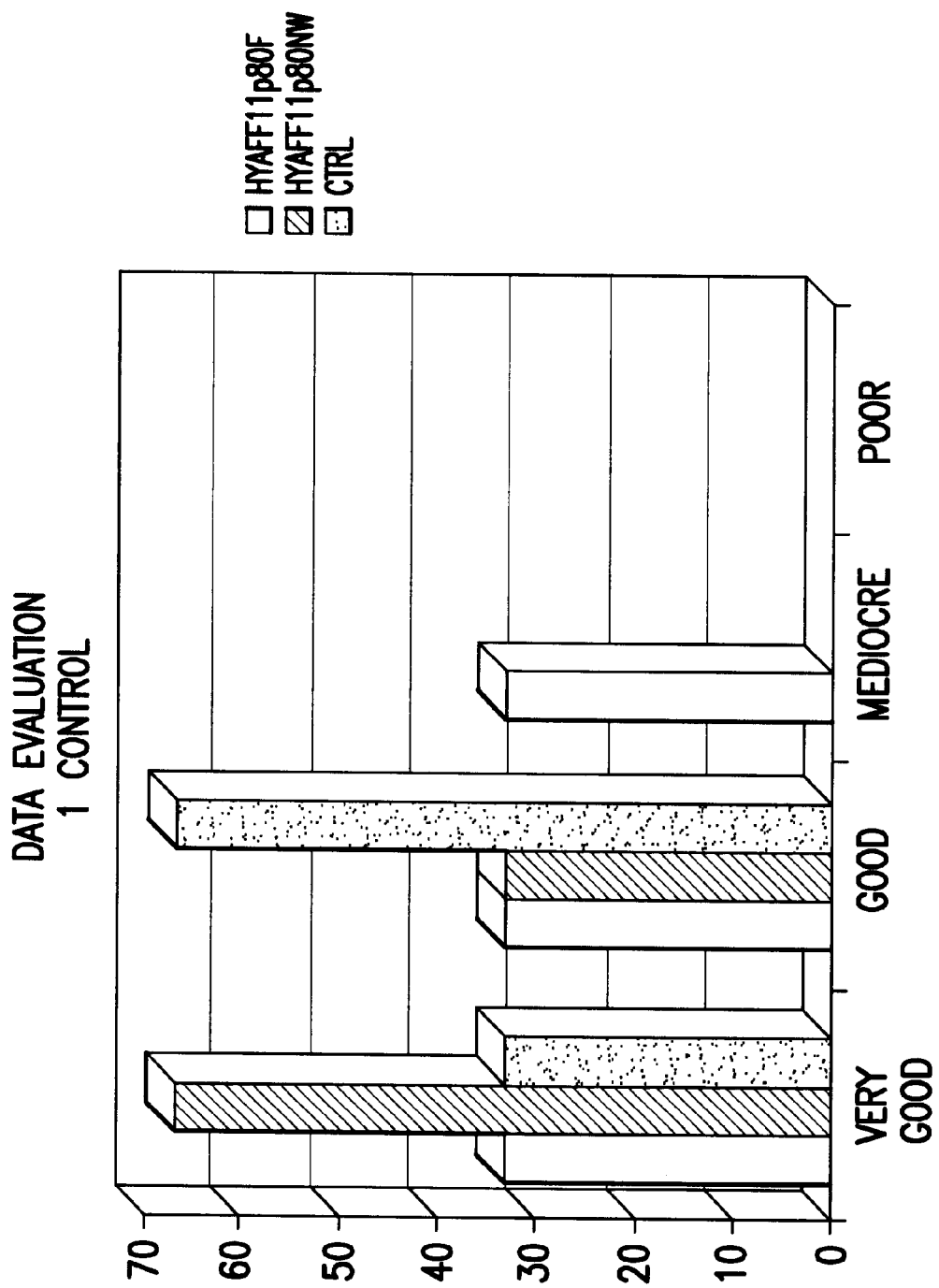
Figure 17:
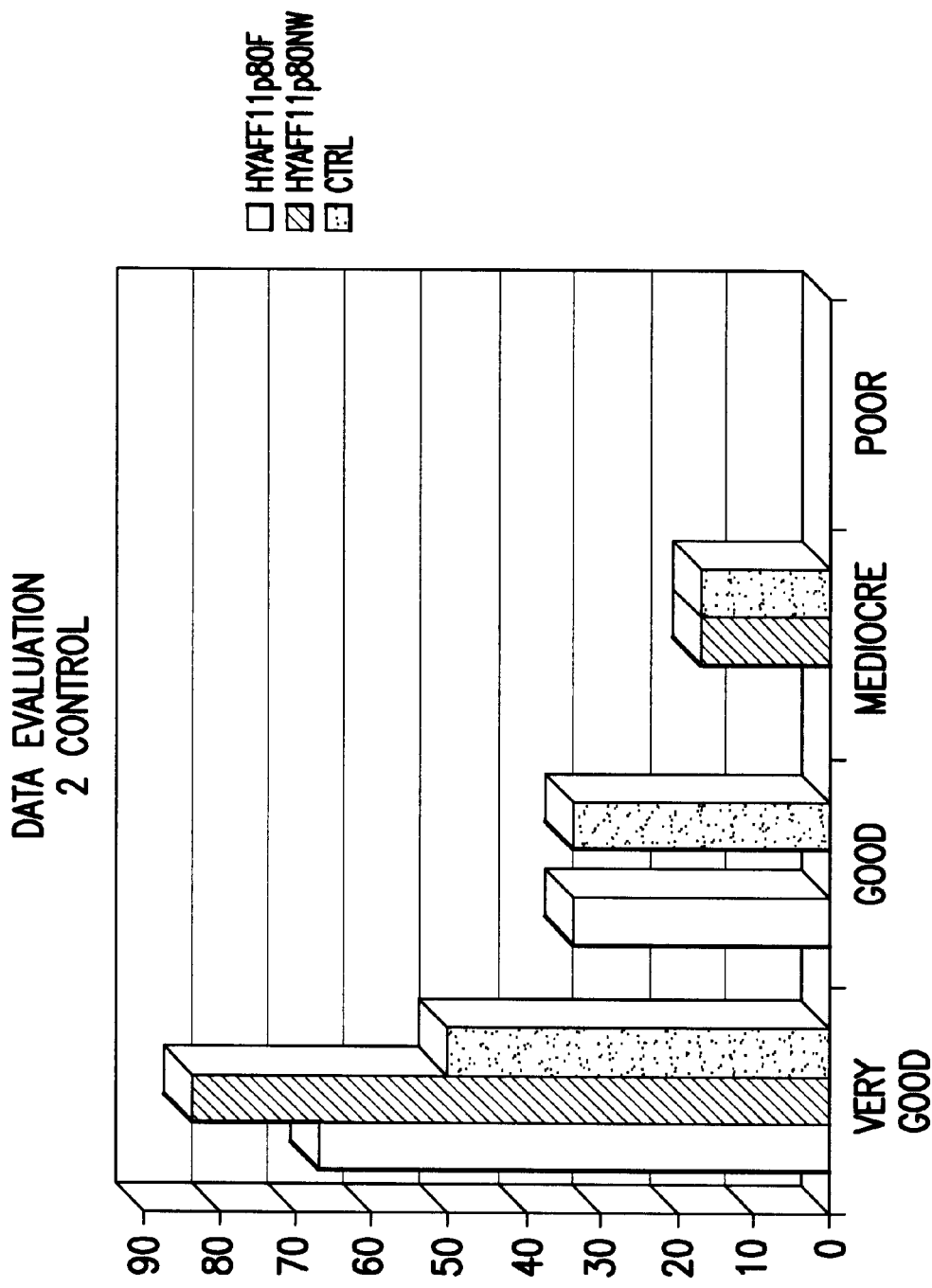
Figure 18:
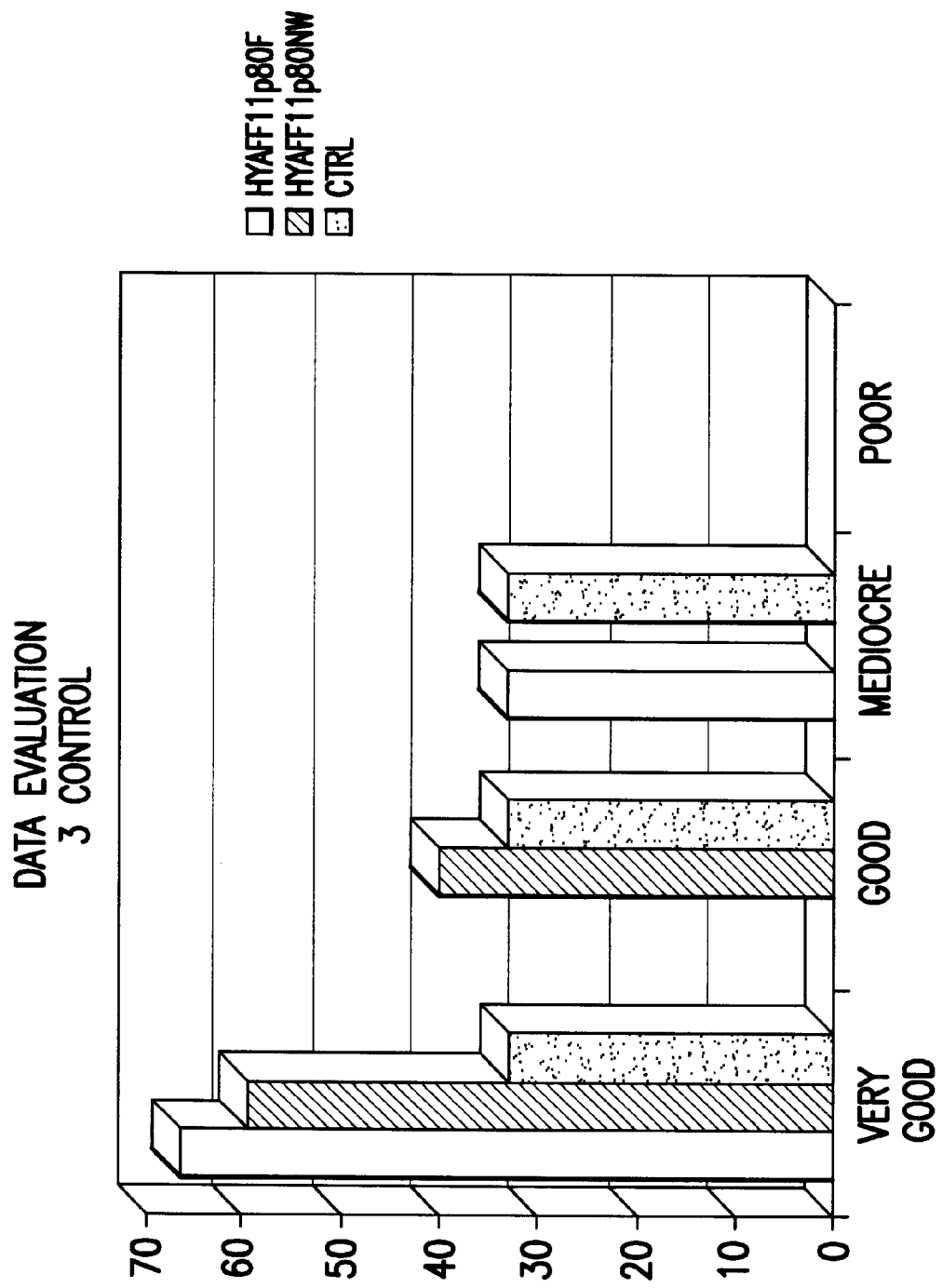
Figure 19:
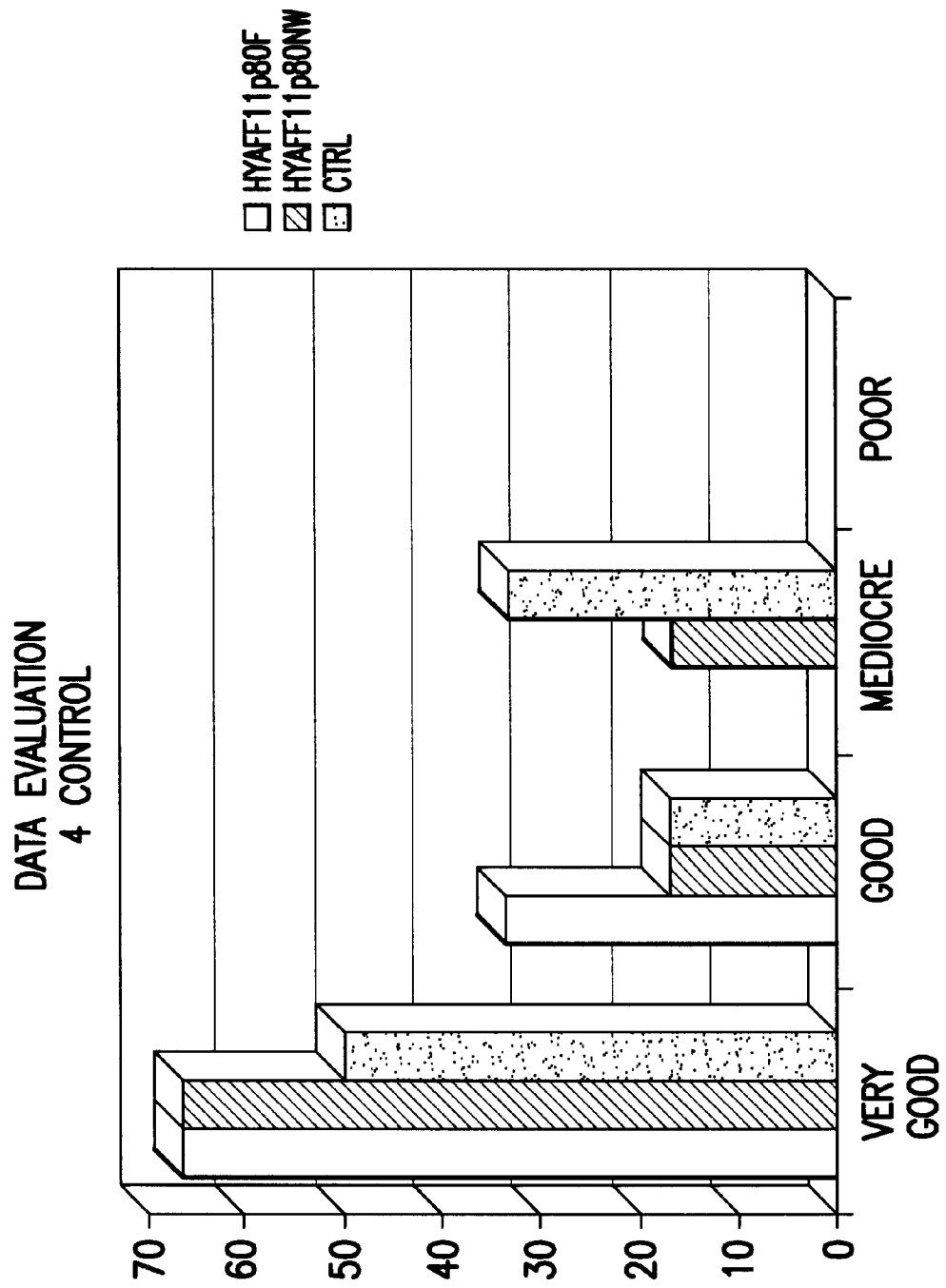
Figure 20:
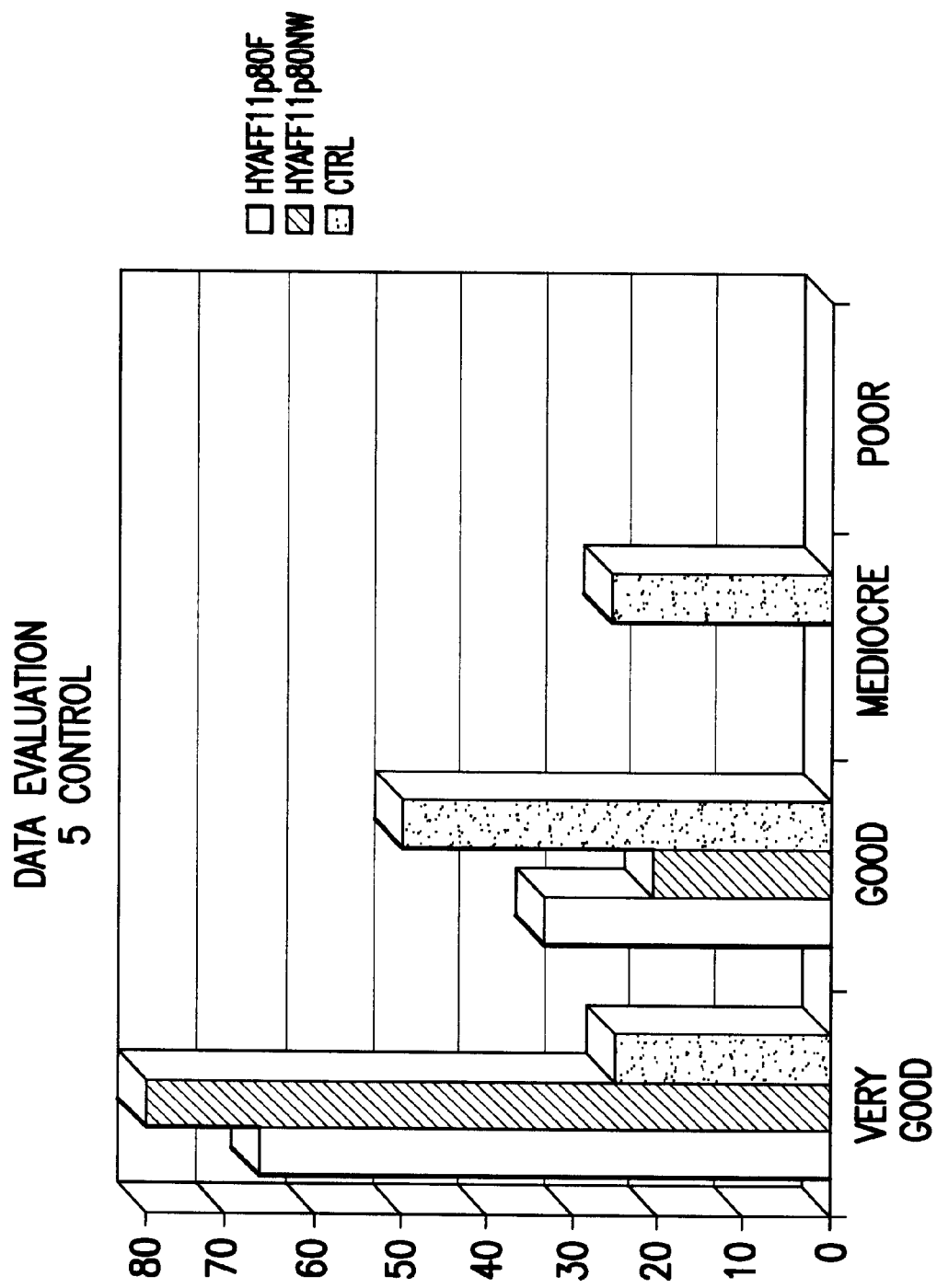
Figure 21:
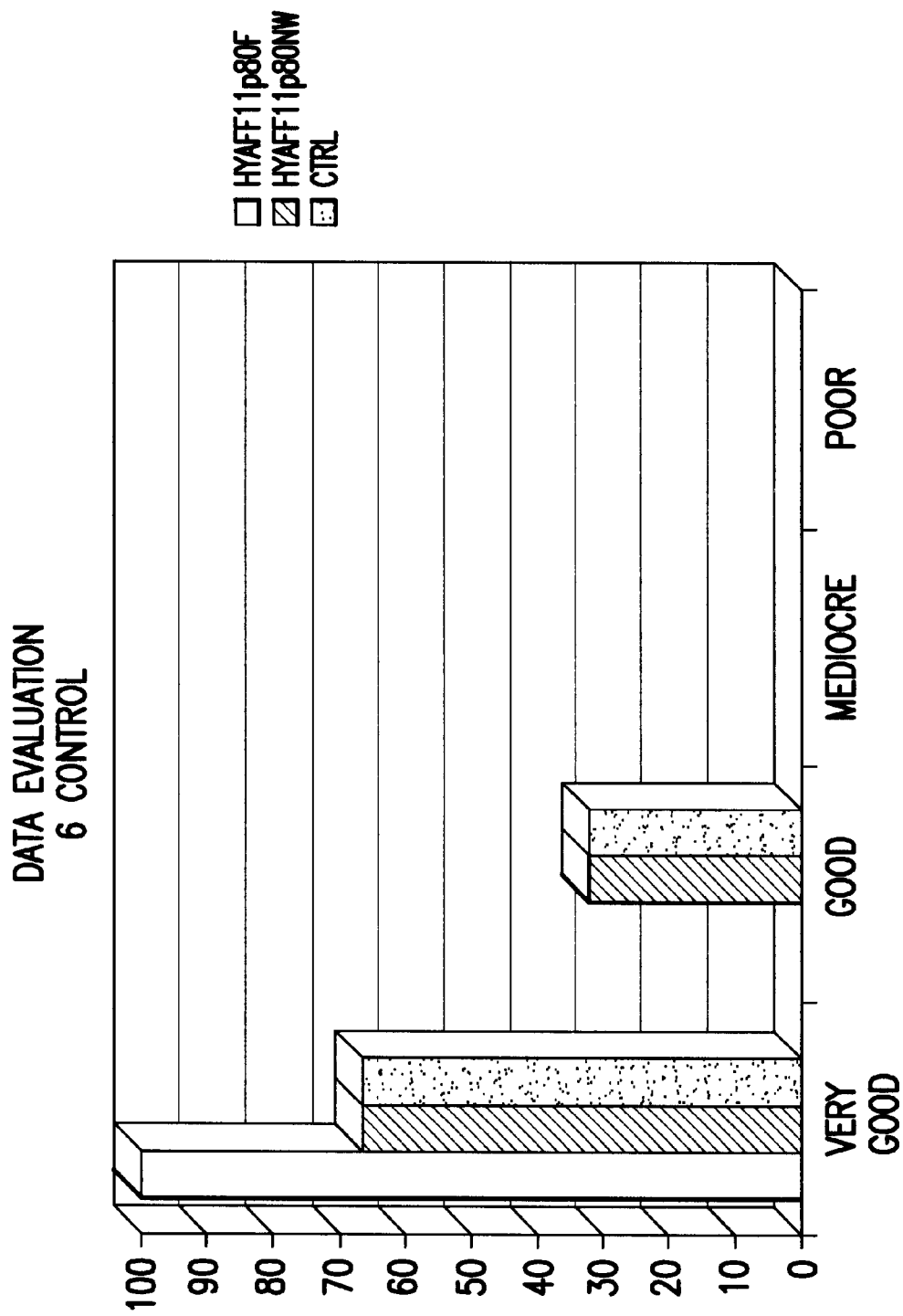

The reduction of crusting was more substantially pronounced in the group receiving HYAFF 11p80-NW, especially after the third visit (see FIG. 15). Only at the $6^{th}$ visit, were patients in the control group free from crusting. With both presentations of the device (HYAFF 11p80-F and HYAFF 11p80-NW), patients were free from crusting at earlier time points (after the second visit for HYAFF 11p80-F and after the third visit for HYAFF 11p80-NW), respectively).

FIGS. 16–21 report the surgeon's observations at each visit on the quality of the healing process. Throughout the study conduct, the surgeon's assessment of patients treated with HYAFF 11p80-NW was either "very good" or "good". At every control visit, the percentage of observations which have been rated "very good" in the HYAFF 11p80-NW group is always greater than 66%.

The observations performed by the second investigator, blinded to the treatment, on a more limited amount of patients are substantially in agreement with those of the first surgeon.

Figure 22:
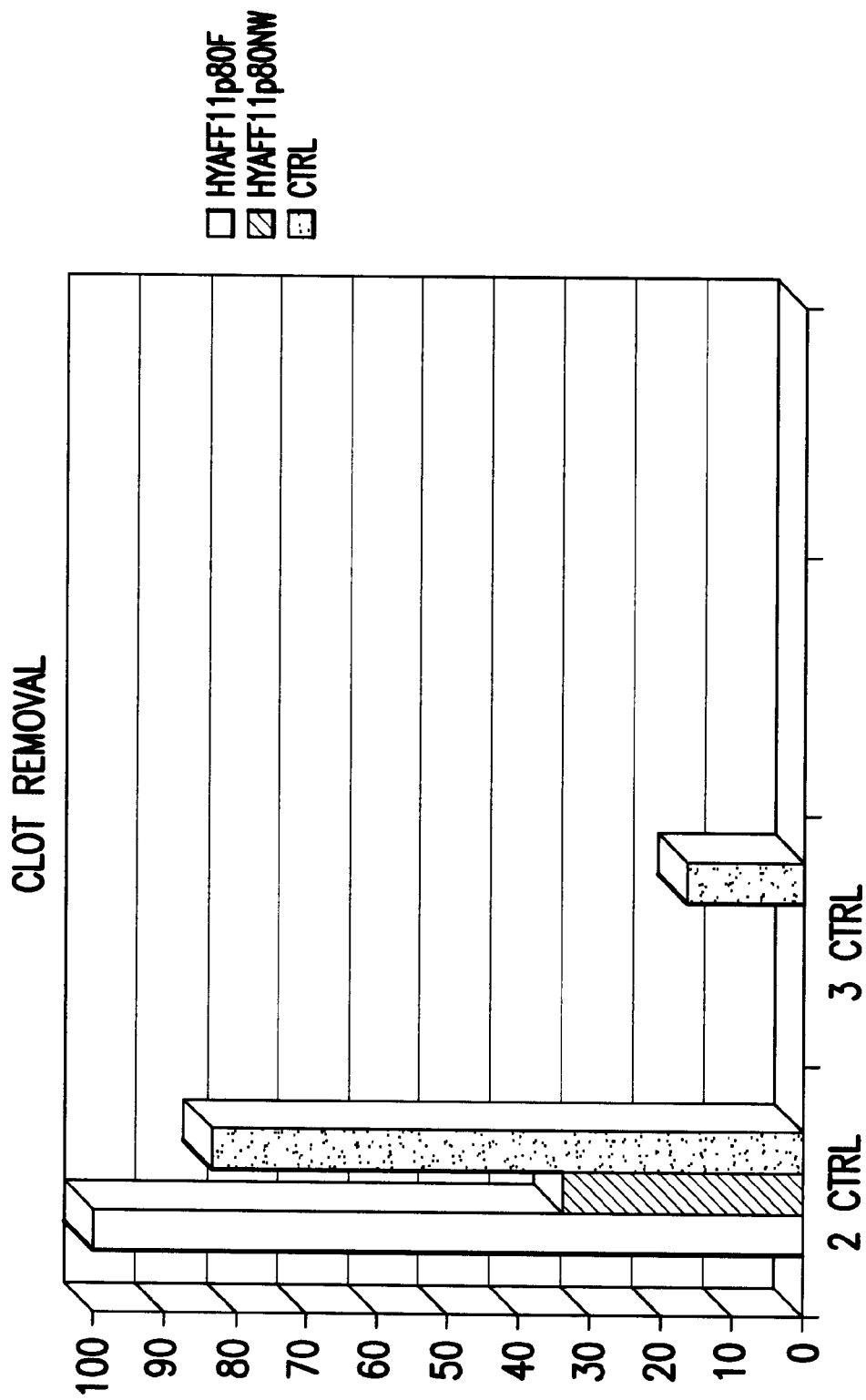
Figure 23:
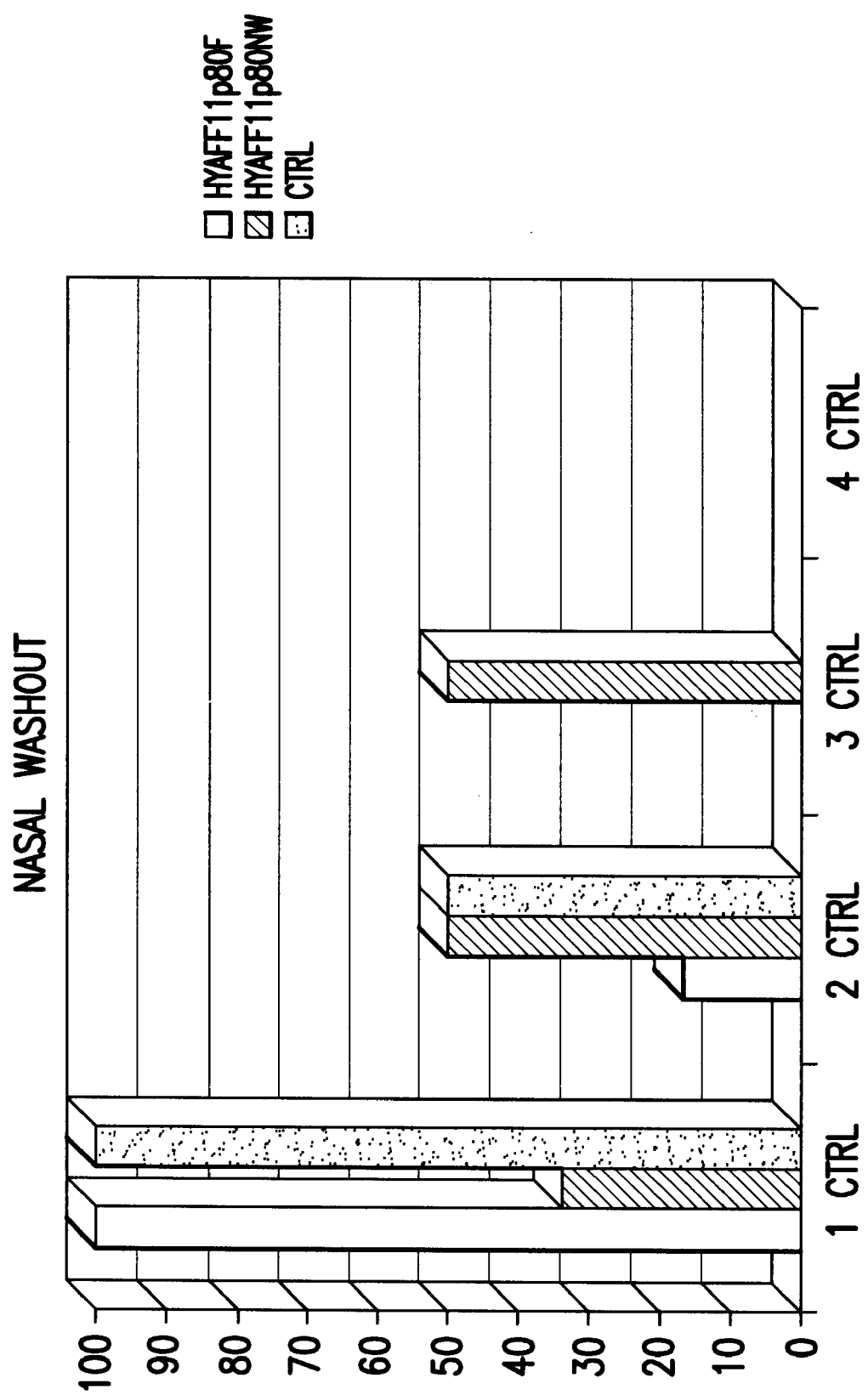

FIGS. 22 and 23 indicate an increased requirement for removal of adhesions, removal of crusts and lavage in the control group compared to the HYAFF 11p80-NW group. No difference was observed at the different time points between groups B and C with respect to the removal of blood clots.

Clinical Global Assessment of HYAFF 11p80-F and HYAFF 11p80-NW:

The final evaluation of the performance, handling properties, ease of removal and tolerability of HYAFF 11p80-F and -NW are classified as very good, fair and poor. Results of such assessment are reported in Table 7. The performances of the devices were rated very good in 5/6 patients of the HYAFF 11p80-NW group and 1/3 of the HYAFF 11p80-F group. The performances in the remaining HYAFF 11p80-NW patient and 2/3 HYAFF 11p80-F patients were considered good. Tolerability of HYAFF 11p80-F and -NW was considered very good in all patients. Handling properties of HYAFF 11p80-NW were considered very good. On the other hand, handling properties of HYAFF 11p80-F were considered poor: this observation led to the decision of removing this group from the study.

Figure 24:
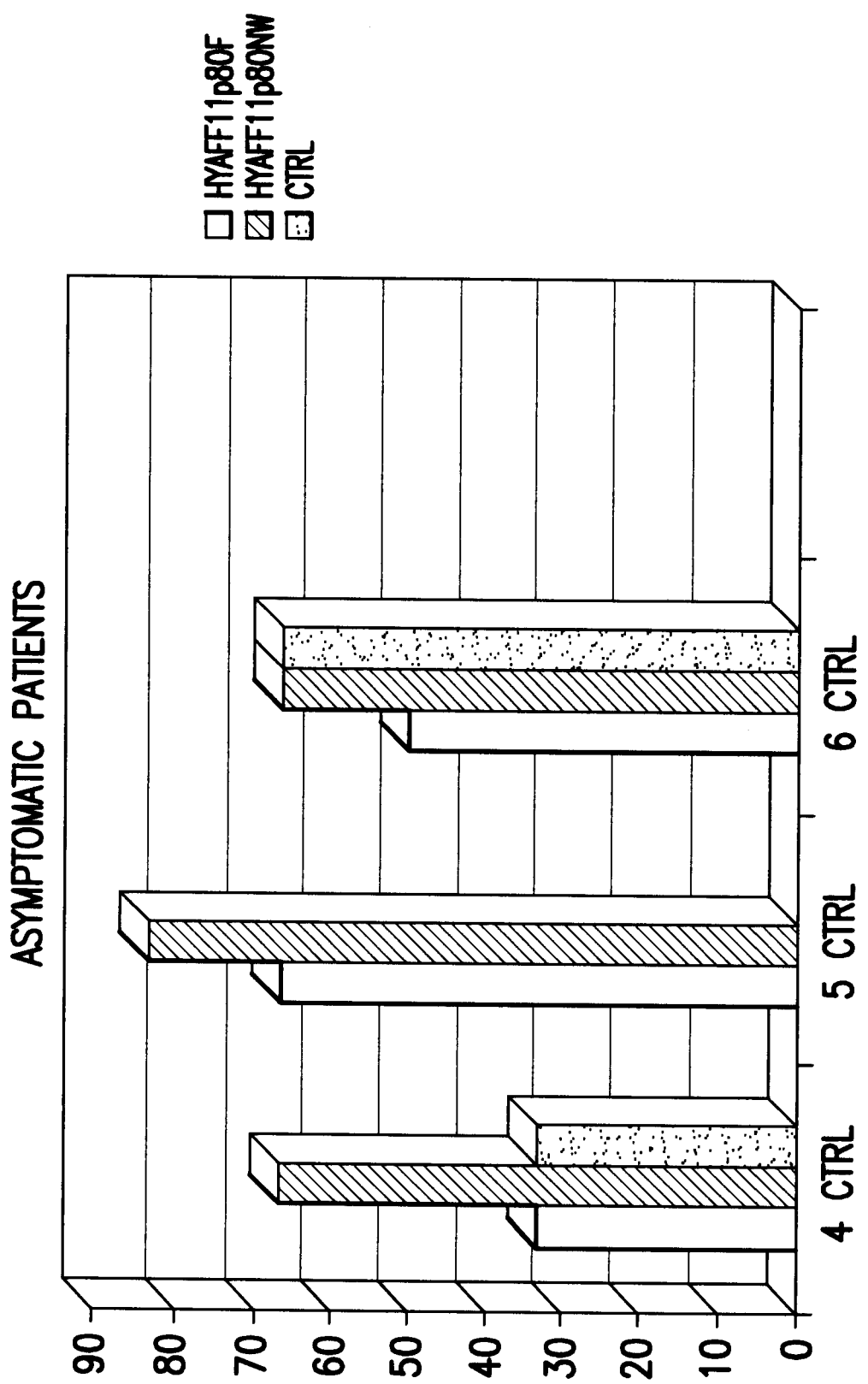

FIG. 24 reports the percentage of asymptotic patients. The highest percentage of asymptomatic patients belongs to group B (HYAFF 11p80-NW).

Conclusion:

The main findings of this study show, HYAFF 11p80-F and -NW is very well tolerated by the patients. No adverse events and no post-surgical complications were recorded during the study. Patient assessment of the tolerability of the device was very good. Another interesting result of this study is that the healing process of the surgical sinus cavity, as assessed by post operative evaluation, is enhanced in patients treated with HYAFF 11p80-F and -NW. In particular, a lower percentage of adhesions and crusting and a higher percentage of asymptomic patients was observed in the experimental group with respect to the control group.

On the other hand, control patients required more frequent and more extensive post-surgical treatments and wash-outs. As a consequence, the use of a sinus liner should reduce the number and the duration of the control visits required. Finally, the number of patients reporting a reduction in the frequency and the severity of symptoms which were present prior to surgery was higher in the HYAFF 11p80-F and -NW treated groups with respect to the control group.

The present studies show that HYAFF 11p80-NW can be used as a sinus liner to prevent occurrence and reduce severity of post-surgical adhesions in endoscopic surgery of the paranasal sinuses.

This study further shows that the healing process of the surgical sinus cavity, as assessed by post operative evaluation, is enhanced in patients who received the application of HYAFF 11p80-F and -NW. In particular, a lower percentage of adhesions and a higher percentage of asymptomic patients was observed in the experimental group compared to the control group.

TABLE 7

GLOBAL CLINICAL ASSESSMENT ON PERFORMANCE AND SAFETY OF HYAFF 11p80-F AND HYAFF 11p80-NW

|  | HYAFF 11p80-F | HYAFF 11p80-NW | TOTAL |
| --- | --- | --- | --- |
| PERFORMANCE |  |  |  |
| Very Good | 1 | 5 | 6 |
| Good | 2 | 1 | 3 |
| HANDLING |  |  |  |
| Very Good | — | 6 | 6 |
| Good | 3 | — | 3 |
| REMOVAL |  |  |  |
| Very Good | 2 | 2 | 4 |
| Good | — | 2 | 2 |
| Fair | 1 | 2 | 3 |
| TOLERABILITY |  |  |  |
| Very Good | 3 | 6 | 9 |

Study 11—Effect of HYAFF™ and ACP Biomaterials on the Prevention of Post Surgical Adhesion Formation in a Rat Liver Abrasion Model The aim of the present study was to test two batches of an internal ester of Hyaluronic Acid (ACP gel) and a continuous membrane of HYAFF™ 11, the benzyl ester of Hyaluronic Acid, to evaluate their effect in the prevention of adhesions. The performances of the test materails were assessed in comparison to a high viscous solution of Hyaluronic Acid high molecular weight.

Experimental Design:

Two batches of ACP gel and a commercial preparation of HYAPF™ 11 membrane were provided. Adhesions were evaluated after 14 days.

A total number of 60 animals were used according with following scheme:

| No | Group | Treatment | Number of Animals |
| --- | --- | --- | --- |
| 1 | Sham operated | Untreated | 12 |
| 2 | Control | HYAL | 12 |
| 3 | Treated | ACP gel — A | 12 |
| 4 | Treated | ACP gel — B | 12 |
| 5 | Treated | HALOBARRIER 20 | 12 |

Preparation of the Animals:

Animals were anesthetized by i.m. injection of a solution of Ketamine+Xylazime (4.5 mg,+0.8 mg/100 g of body weight), shaved and then disinfected with iodine solution and ethanol. Following laparotomy on the left side, the left lobe of the liver was reflected upwards and the inner surfaces of the left and medial lobes of the liver were abraded by gentle rubbing with a wooden applicator until evidence of bleeding or serous exudate was obtained.

Administration of Materials:

After hemostasis obtained with TABOTAMP, ACP gels and HYAL were administered in a standard volume of 2 ml. Transprocess was applied over the injury area in a size 2 cm×2 cm.

The surgical site was closed in two layers with 3.0 silk sutures.

At the end of surgery an antibiotic (Procacillina subcutaneous 30,000 I.U./rat) and an analgesic (Nefam, 0.02 ml/rat sub-cutaneously corresponding to 0.4 mg) were administered for 4 days.

Observations and Determinations

Adhesion Grade:

At the termination of the experiment, animals were euthanized by $CO_2$.

The adhesions formed were evaluated by gross observation according to the following adhesion score:

0=No adhesions.
1=Low to moderate adhesions.
2=Marked adhesions and tissue damage.

The resorbability of the materials was evaluated by visual assessment of the presence of the materials and, furthermore, the site of treatment photographed.

After gross observations, the entire liver was surgically removed and placed in 10% buffered formalin for 48 hours. After fixation, a 2.0 mm cross section including the abraded area was removed from the liver by using a dissecting blade. The specimen so obtained was subjected to histological analysis.

Percent of Animals With Adhesion Grade=2:

An adjunctive evaluation of percentage of animals with adhesion grade=2, in each treatment group, was made.

Histological Analysis:

Specimens were fixed in neutral buffered formalin 10% and subsequently dehydrated and embedded in paraffin by standard techniques. 8 μm sections were stained with Ematoxilin/Eosin and Mallory's trichrome for evaluation of tissue inflammatory reaction and material.

Results:

The placement of the biomaterials was easily accomplished. ACP gels and HYALOBARRIER 20 did not move after placement. Hyaluronic Acid due to its low viscosity dispersed quickly from hepatic lobe. A total number of 4 animals died between 1 and 2 days after surgery. Necropsy showed internal haemorrhage in the two animals treated with Hyaluronic Acid. The remaining two animals showed breaking of suture close to the laparotomy with leackage of the internal organs.

Gross Observation, Evaluation of Adhesion Formation:

At the time of evaluations (10–14 days after the application) ACP treatments and control substances were completely absorbed and HYALOBARRIER 20 treatment was still present.

Adhesion formation: the ACP 5% gels batches A, B and HYALOBARRIER 20, showed a remarkable reduction of postsurgical adhesions formation compared to HYAL and untreated controls. Statistical analysis showed significant differences (P<0.05).

Figure 25:
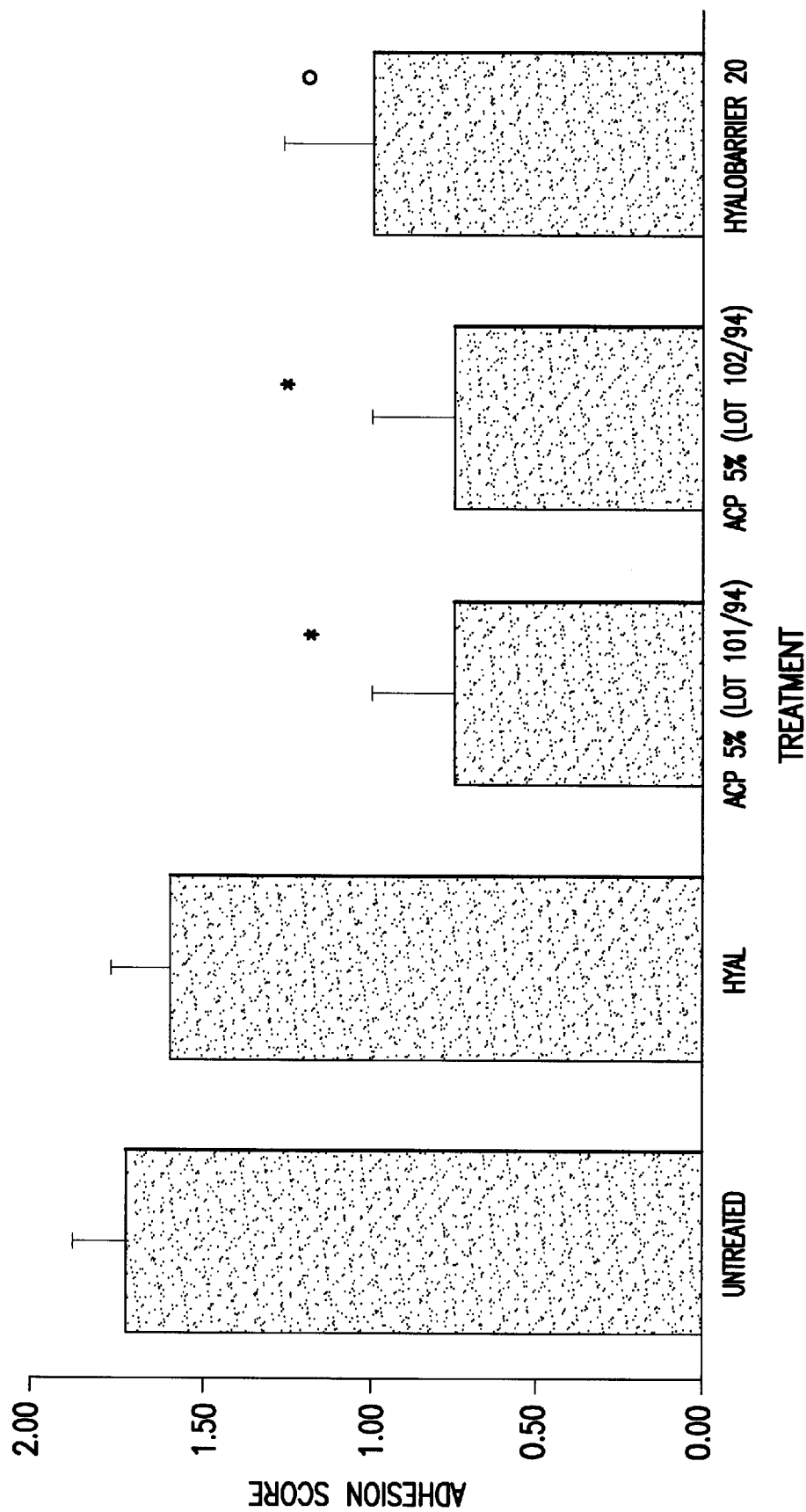

The results of the mean of adhesion score are summarize in the Table 8 and in FIG. 25.

Figure 26:
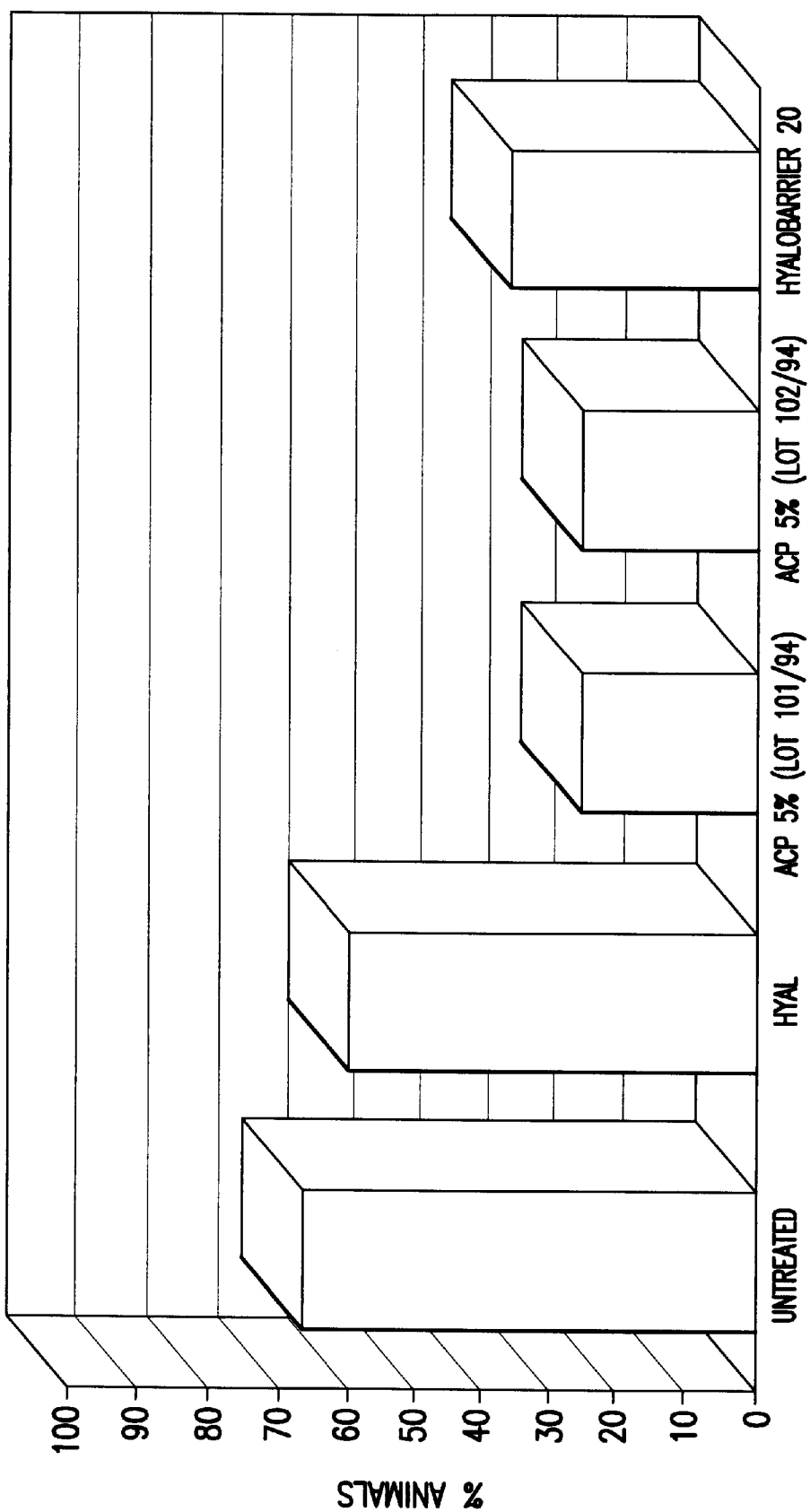

The percentage of animals with adhesion grade=2 in each treatment group confirmed the results above: ACP batch A and batch B had the lower percentage of adhesions grade=2 (25%) and HYALOBARRIER 20 showed a percentage of 36%. The values of Hyaluronate derivatives compared favorably to the HYAL at 60% and untreated control at 66%. The percentage of animals with significant adhesions is summarized in the Table 9 and FIG. 26.

Histomorphological Observation:

With microscope observations the ACP batches A and B showed the lowest tissue inflammatory reaction. In the majority of the samples the thickness of granulation tissue was very low and no unfavourable reaction was noted on the surface of the two hepatic lobes (lower and upper). Fibrills collagens began to organize and the healing process was completed. HYALOBARRIER 20 showed a moderate tissue reaction. The thickness of granulation tissue was slightly higher than ACP treatments but the membrane kept the two lobes separated. A moderate inflammatory reaction was observed with the HYAL treatments and untreated control, however in many cases hepatic lobes were completely attached.

Discussion:

Two batches of ACP gel (an internal ester of Hyaluronic Acid), and a continuous HYAFF 11 derivative membrane, 20 μm thick, with different physico-chemical properties were investigated in order to characterize a device able to prevent or reduce postsurgical adhesions. The data from this experiment indicate that devices made from derivatives of Hyaluronic Acid decreased the risk of postsurgical adhesions between two anatomical adjacent surfaces (hepatic lobes) and compared favorably with the Control material (HYAL, Hyaluronic acid M.W. 800,000) and untreated group (sham operated). Moreover the biomaterials showed good biocompatibility and a very low inflammatory tissue response.

TABLE 8

Degree of adhesion in a rat liver abrasion model: Mean ± standard error mean of adhesion score 14–16 days after surgery.

| Treatment | No. of Animals | Mean ± Standard error mean of Adhesion Score |
|---|---|---|
| Untreated | 11 | 1.73 ± 0.15 |
| HYAL ® | 10 | 1.60 ± 0.16 |
| ACP gel — A | 12 | 0.75 ± 0.25* |
| ACP gel — B | 12 | 0.75 ± 0.25* |
| Hyaloarrier 20 | 11 | 1.00 ± 0.27** |

*p < 0.05 vs. untreated (sham operated) and HYAL ®
**p < 0.05 vs. untreated (sham operated)

TABLE 9

Percentage of animals per treatment group with grade of adhesion = 2 (significant adhesions) 14–16 days after surgery.

| Treatment | No. of Animals | Percentage of Animals |
|---|---|---|
| Untreated | 11 | 66.7 |
| HYAL ® | 10 | 60 |
| ACP gel — A | 12 | 25 |
| ACP gel — B | 12 | 25 |
| HYALOARRIER 20 | 11 | 36 |

Study 12—ACP-Hyalogel Barrier in Laparoscopic Adhesion Prevention in the Rabbit Uterine Horn Model The aim of this study was to compare a hyaluronate derivative biomaterial, ACP Hyalogel barrier and an absorbable oxidized cellulose barrier (TC7 INTERCEED) in their ability to prevent adhesion formation after peritoneal and uterine injuries inflicted by laparoscopy, and to assess the histology of adhesions in presence of different substance.

Experimental Design:

ACP Hyalogel barrier (FAB Abano Terme Italy) was prepared by hydration of the powder in order to obtain a concentration of 6%. The relative cross-linking level was 5%, the transparent gel had a viscosity of 450 Paxsec. The gel was steam sterilized in 5 ml glass syringes.

Oxidized regenerated cellulose (TC7 INTERCEED) was purchased from Ethicon, Sommerville, N.J. U.S.

Sixty-four adult female New Zealand White rabbits, sexually matured, weighing 2.5 to 3.0 Kg and 3–4 months aged, were housed under controlled environmental conditions at the Fidia Research Laboratories Animal Care.

At the time of surgery animals were anesthetized with 50 mg/kg Ketamine (Ketavet, Gellini Pharmaceutical Aprilia, Italy) and 1.6 mg/kg xylazine (Rompun Bayer AG Leverkusen, Germany). Additionally 5 mg/kg enrofloxacin (Baytril, Bayer AG Leverkusen, Germany) was administered by sc injection before surgery. The rabbits were then placed in the supine position, shaved on the abdomino-pelvic area, prepped with iodine solution and ethanol then draped in sterile fashion.

A Verres needle 1.2 mm diameter was inserted in the abdominal cavity entering the abdominal wall in the midline for carbon dioxide gas insufflation using an automatic laparoinsufflator (Storz, Tuttlingen, Germany)(intraabdominal pressure 8–12 mm Hg in flow 3 L/min). A 4.5 mm diameter trocar was inserted entering the abdominal wall at the same position. A 4 mm diameter, 18 cm length, artoscope (Storz) was inserted in the cavity through the trocar with the aid of Zenon 300 W light source. All surgical procedures were performed by means of an endoscopic microcamera (Mono CCD Endocam, Storz). Following inspection of the abdomen, laparoscopic scissors and atraumatic forceps of 5 mm diameter were inserted without trocar through two lateral incisions.

A standardized injury was induced according to the following steps:
(1) a 2 $cm^2$ area of the right uterine mesometrium was denuded; (2) the medial right uterine horn was crushed for 30 seconds with forceps; (3) a 1 cm incision was made in the distal right uterine horn; (4) a 5 $cm^2$ area of the peritoneum of the abdominal wall in front of the previous lesions was denuded.

Accurate hemostatis was obtained by monopolar electrocoagulation.

The animals were randomized into three groups: 22 animals received no treatment (Group 1, untreated control), in 20 animals TC7 INTERCEED was used (Group 2). The material according to the size and shape of injury was carefully folded before use to be inserted through a lateral abdominal incision. The barrier was unfolded inside the peritoneal cavity by means of forceps and applied on the lesion. In Group 3 (22 animals), 5 ml of ACP gel were injected by means of a glass syringe with a 18 gauge needle inserted in the abdomen. The gel was uniformly distributed on all of the injured areas. At the end of surgery all rabbits were treated with 0.8 mg/kg Nefopam (Nefam, Farma-Biafini Naples, Italy).

Six weeks later animals were euthanized by $CO_2$ asphyxiation: a laparatomy was performed; and the adhesion grade was blindly evaluated according to Blauer's scoring system: 0=No adhesions; 1=Thin or narrow, easily separable adhesions; 2=Thick adhesions, limited to one area; 3=Thick and widespread adhesions; 4=Thick and widespread adhesions, plus adhesions of viscera to anterior and/or posterior abdominal wall. A biopsy of adhesions was performed in some animals where moderate and severe adhesions were present. Tissue was removed and fixed in 10% formalin, and stained with hematoxylin and eosin. Histological analysis evaluated for giant cellular reaction, fibrosis, granulation tissue, fat necrosis and granulomatosis, according to a 0 to 3 scale.

A statistical analysis was applied using the Kruskall Wallis non-parametric test for adhesion score and the Mann Whitney U test for histological scores to compare treatment and control groups. Significant differences were considered at $P<0.05$. Data are expressed as means±sem.

Results:

Three animals died 4 and 5 days after surgery, (2 of the ACP group an 1 of the untreated group). Two rabbits presented an intestinal stenosis due to electrical injury. The third rabbit died of intestinal hernia through the laparoscopic incision of the abdominal wall (laparocele) resulting in necrosis of the tissue.

At the end of the second-look laparotomy ACP gel was completely absorbed whereas in the TC7 INTERCEED control group remnants of biomaterial were present.

The ACP treatment group showed the lowest incidence of postsurgical adhesions as compared to INTERCEED and untreated control group. The adhesions scores were respectively 1.25±0.28 (ACP), 2.45±0.22 (TC7 INTERCEED) and 2.24±0.26 (untreated) (Table. 10).

Statistically significant differences were noted between ACP vs. untreated control (P=0.0058) and ACP vs. INTERCEED (P=0.003) but not between TC7 INTERCEED and untreated control (P=0.01712) High grade adhesions (score$\geq 2$) were noted in 35% of ACP-treated, in 66% of control rabbits and in 85% of TC7 INTERCEED-treated animals.

The ACP biomaterial was applied exerting a moderate pressure on the syringe and it stayed in place after administration.

No adhesions were observed in the left uterine horn were no trauma had been induced.

The histological findings of severe adhesions showed no significant difference among the groups with respect to flogosis, granulation tissue, fat necrosis and giant cells. The ACP treated group showed the lowest score of fibrosis, and significant differences were noted between ACP gel group and TC 7 INTERCEED group (p=0.031). The analysis of macrophage presence showed differences between untreated and ACP groups vs. TC7 INTERCEED group (p=0.014). Total absence of granulomatosis was found in all treatments (Table 11).

TABLE 10

Adhesion score and percentage of animals with adhesion score $\geq 2$ in each treatment group.

| Treatment | No of Rabbits | Score 0 | 1 | 2 | 3 | 4 | Mean ± SEM | % Animals score $\geq 2$ |
|---|---|---|---|---|---|---|---|---|
| Control (untreated) | 21 | 1 | 6 | 4 | 7 | 3 | 2.24 ± 0.26 | 66% |
| TC 7 INTERCEED | 20 | — | 3 | 9 | 4 | 4 | 2.45 ± 0.22 | 85% |
| ACP gel | 20 | 7 | 6 | 3 | 3 | 1 | 1.25 ± 0.28* | 35% |

*P < 0.05 ACP vs. untreated and TC7 INTERCEED (non-parametric Kruskal Wallis test)

TABLE 11

Histologic Features of Severe Adhesions Biopsies

| Histologic Feature | Group | Score 0 | 1 | 2 | 3 | Mean ± SEM |
|---|---|---|---|---|---|---|
| Flogosis | Untreated | 5 | 5 | 1 | 0 | 0.64 ± 0.2 |
| | TC7 | 7 | 9 | 0 | 0 | 0.56 ± 0.13 |
| | INTERCEED ACP gel | 5 | 5 | 0 | 1 | 0.73 ± 0.27 |
| Granulation tissue | Untreated | 6 | 5 | 0 | 0 | 0.45 ± 0.16 |
| | TC7 | 13 | 2 | 0 | 1 | 0.31 ± 0.20 |
| | INTERCEED ACP gel | 5 | 5 | 0 | 1 | 0.73 ± 0.27 |
| Giant cells | Untreated | 3 | 1 | 0 | 4 | 1.36 ± 0.41 |
| | TC7 | 4 | 3 | 3 | 6 | 1.69 ± 0.31 |
| | INTERCEED ACP Gel | 3 | 6 | 1 | 1 | 1.00 ± 0.27 |
| Fibrosis | Untreated | 8 | 3 | 0 | 0 | 0.27 ± 0.14 |
| | TC7 | 8 | 5 | 1 | 2 | 0.81 ± 0.26 |
| | INTERCEED ACP gel | 10 | 1 | 0 | 0 | 0.09 ± 0.09* |
| Fat necrosis | Untreated | 7 | 1 | 0 | 3 | 0.91 ± 0.41 |
| | TC7 | 12 | 1 | 1 | 2 | 0.56 ± 0.27 |
| | INTERCEED ACP gel | 8 | 2 | 0 | 1 | 0.45 ± 0.28 |
| Macrophages | Untreated | 9 | 2 | 0 | 0 | 0.18 ± 0.12 |
| | TC7 | 6 | 3 | 5 | 2 | 1.19 ± 0.28 |
| | INTERCEED ACP gel | 9 | 2 | 0 | 0 | 0.18 ± 0.12* |

*P < 0.05 ACP gel vs. TC7 INTERCEED (Mann Whitney U test)

Discussion:

The results of this study show that ACP gel reduces significantly post surgical adhesions formation compared to an oxidized regenerated cellulose and to no anti-adhesive treatment at all. The efficacy of the hyaluronan based gel may be due to several features of the material: ACP is highly viscous and conformable to the uterine and abdomino-pelvic surfaces and it remains adherent to the tissue for a suitable period before degradation.

Study 13—Cross-linked Hyaluronan in Adhesion Prevention After Flexor Tendon Surgery in Rabbits The aim of the present study is to evaluate these new preparations in an experimental model for biomechanical characterization of postoperative adhesions after flexor tendon repair in rabbit digits.

Experimental Design

Surgical Procedure:

Thirty rabbits of the same breed (Swedish loop) and of both sexes (3.0–4.8 kg) were used.

The third digit on both hindpaws were used for tenotomy followed by tendon repair and finally application of either a hyaluronate derivative or buffered saline solution in a randomized fashion.

The rabbits were given anesthesia with fentanyl-fluanisone (Hypnorm Vet, Janssen, Belgium) 0.3 ml/kg b.w. i.m. and midazolam (Dormicum, Roche, Switzerland) 2 mg/kg b.w. i.m. Cefuroxime (Zinacef, Glaxo, England) 100 mg, was given i.v. for prophylaxis against infection.

Both hindpaws were shaved and prepared in the usual sterile fashion. All operations were performed under microscope using microsurgical instruments. The operation started with the left hindpaw. A proximal tenotomy of the flexor digitorum fibularis (FDF) and the flexor digitorom superficialis (FDS) was performed above the ankle of the hindleg to relieve tension of the distal experimental tenotomy and tenorrhaphy to be done in the digit. A longitudinal skin incision was then made plantarly in the third digit along the proximal phalanx and continued through the flexortendon sheath. The pulleys were left intact. The FDS tendon was resected between the anular plantar ligament and the first anular digital ligament. The FDF tendon was severed and then sutured using a modified Kessler suture (5-0 PROLENE monofilament, V-18 needle, Ethicon) followed by a continuous adaptation suture of the tendon ends (7-0 Nylon monofilament, S&T). The same surgical procedure was performed with the right hindpaw.

In the control digit the sheath was closed and buffered saline solution was flushed through the tendon sheath. In the experimental digit, the test substance was placed around the tendon repair. Solid test substance was placed before closure of the tendon sheath and buffered saline solution was flushed through the tendon sheath. Viscous test substance was injected into the tendon sheath with a catheter after closure of the sheath. Injection was continued until the sheath was filled (approximately 1 ml).

The animals were killed two weeks after tendons surgery with an overdose of pentobarbital and the digits were taken for examination. The skin was removed and all structures divided at the proximal level of the metatarsal bone. After removal, the digits were examined in a test instrument.

Test Material:

Three different hyaluronan derivatives were used, two solid woven preparations: Hyaff 11—large mesh (hyaff 11 lm) and a fine mesh of (HYAFF 11 fm) (Hyalonect diHyaff 11), and one liquid preparation: ACP 5 (50mg/ml). Ten rabbits were used for each type of test substance.

Test Instrument:

An instrument which was capable of pulling the flexor tendon with increasing force and simultaneously performing a continuous registration of the resulting flexion of the DIP joint, tendon excursion and force was used. The digit was mounted on the instrument by fixation of the middle phalanx and metatarsal to the instrument so as not to interfere with the tendon gliding. The proximal interphalangeal joint was immobilized in 90 degrees of flexion and the metatarsophalangeal joint in a straight position. The proximal end of the FDF tendon was clamped and connected to an electric motor, which was run at a constant speed of 14 mm/min. A precision potentiometer measured angular rotation. A strain-gauge instrument measured the tension. All measurements were graphically registered using a computerized program (Lab View). The test was run until full DIP joint motion and rupture of the tendon repair occurred. The maximum tensile load during flexion to reach an angular rotation of 50 degrees in the DIP joint was registered (MTL50). This value represents the resistance that must be overcome to achieve full flexion of the DIP joint and can be used to determine the functional hindrance caused by adhesions.

Statistics:

The effect of each hyaluronan preparation versus the contralateral saline solution regarding adhesion preventive effect and the tensile strength of the tendon repair was evaluated using the Wilcoxon Signed-Rank test.

Results:

The animals tolerated the surgical procedure well and the wounds appeared macroscopically free of infection, except in two animals, which had subcutaneous infections but without involvement of the tendon sheath. A total of 60 digits were operated. In two of these there were ruptures of the tendon repairs but no sign of infection.

All the tested substances showed better mean values of MTL50 compared to the control digits (Hyaff 11—large mesh, p=0.241, Hyalonect diHyaff 11, p=0.126 and ACP 5, p=0.284) (Table 12). Hyaff 11—large mesh and ACP 5 showed a significant lower tensile strength of the tendon repair compared to the control digits (p=0.049; p=0/028) (Table 13). No impairment of tensile strength of the tendon repair was seen with Hyalonect diHyaff 11.

There was a large interanimal variation in the extent of adhesions formed. Restrictive adhesions are defined as MTL 50≧4.5 N. According to this definition 16 adhesion formers and 14 non-adhesive formers were found among the animals treated. Hyalonect diHyaff 11 showed significant adhesions preventive effect in adhesion forming animals (p=0.043) (Table 12).

Discussion:

The results of the present study show that Hyalonect diHyaff 11 combined the best mean value for adhesion preventive effect compared to saline solution and no simultaneous impairment of tensile strength of the tendon repair. A number of animals, close to 50%, did not form restrictive adhesions in either digit. In evaluating the results in the group of animals in which restrictive adhesions actually did form, Hyalonect diHyaff 11 showed a significant adhesion preventive effect. Among the animals tested with Hyaff 11 1 m only two animals appeared as adhesion formers and the results for this substance is therefore not conclusive.

The solid hyaluronan preparations were presented as woven material with either large or fine mesh. As the fine mesh material (Hyalonect diHyaff 11) presented the best results, the size of the mesh may be of importance.

TABLE 12

Evaluation of adhesion formation 15 days postop.

| Exp Material | MTL 50 | | MTL 50 ≦ 4.5N | | MTL 50 > 4.5N | |
| --- | --- | --- | --- | --- | --- | --- |
| | Exp | Control | Exp | Control | Exp | Control |
| ACP5 | 6.4 | 8.1 | 3.4 | 1.0 | 6.7 | 8.9 |
| HYAFF 11 lm | 2.6 | 4.0 | 1.4 | 1.5 | 7.4 | 14.3 |
| Hyalonect fm | 2.7 | 4.6 | 1.8 | 1.0 | 3.6 | 8.1 |

TABLE 13

Tensile strength of tendon repair 15 days postop

| Exp material | Exp digit | Control digit |
| --- | --- | --- |
| ACP 5 | 9.2 ± 5.7 | 13.9 ± 5.0 |
| Hyaff 11 lm | 10.7 ± 2.2 | 13.2 ± 3.5 |
| Hyalonect fm | 11.4 ± 1.3 | 11.9 ± 5.3 |

Study 14—HYALOBARRIER 20 and 50 in Adhesion Prevention After Flexor Tendon Surgery in Rabbits The aim of the present study is to evaluate two new membranes made from HYAFF 11 and having a thickness of 20 $\mu$m or 50 $\mu$m (HYALOBARRIER 20 and 50, respectively), in an experimental model for biomechanical characterization of postoperative adhesions after flexor tendon repair in rabbit digits.

Experimental Design:

Twenty rabbits of the same breed (Swedish loop) and of both sexes (3.1–4.7 kg) were used. The third digit on both hindpaws were used for tenotomy followed by tendon repair and finally application of either a hyaluronate derivative or buffered saline solution in a randomized fashion.

The rabbits were given anesthesia with fentanyl-fluanisone (Hypnorm Vet, Janssen, Belgium) 0.3 ml/kg b.w. i.m. and midazolam (Dormicum, Roche, Switzerland) 2 mg/kg b.w. i.m. Cefuroxime (Zinacef, Glaxo, England) 100 mg was given i.v. for prophylaxis against infection.

Both hindpaws were shaved and prepared in the usual sterile fashion. All operations were performed under microscope using microsurgical instruments. The operation started with the left hindpaw. A proximal tenotomy of the flexor digitorum fibularis (FDF) and the flexor digitorum superficialis (FDS) was performed above the ankle of the hindleg to relieve tension on the distal experimental tenotomy and tenorrhaphy to be done in the digit. A longitudinal skin incision was then made plantarly in the third digit along the proximal phalanx and continued through the flexor tendon sheath. The pulleys were left intact. The FDS tendon was resected between the anular plantar ligament and the first anular digital ligament. The FDF tendon was severed and then sutured using a modified Kessler suture (5-0 PROLENE monofilament, V-18 needle, Ethicon) followed by a continuous adaptation suture of the tendon ends (7-0 Nylon monofilament, S&T). The same surgical procedure was performed in the right hindpaw. In the control digit, the sheath was closed and buffered saline solution was flushed through the tendon sheath. In the experimental digit, the test substance was placed around the tendon repair before closure of the tendon sheath. Buffered saline solution was flushed through the tendon sheath.

The animals were killed two weeks after tendon surgery with an overdose of pentobarbital and the digits were taken for examination. The skin was removed and all structures divided at the proximal level of the metatarsal bone. After removal, the digits were examined in a test instrument.

Test Material. One hyaluronan derivative (HYALOBARRIER) with two different thicknesses (20 and 50 $\mu$m) was used. Ten rabbits were used for each type of test substance.

Test Instrument. An instrument which was capable of pulling the flexor tendon with increasing force and simultaneously performing a continuous registration of the resulting flexion of the DIP joint, tendon excursion and force was used. The digit was mounted on the instrument by fixation of the middle phalanx and metatarsal to the instrument so as not to interfere with the tendon gliding. The proximal interphalangeal joint was immobilized in 90 degrees of flexion and the metatarsophalangeal joint in straight position. The proximal end of the FDF tendon was clamped and connected to an electric motor, which was run at a constant speed of 14 mm/min. A precision potentiometer measured angular rotation. A straingauge instrument measured the tension. All measurements were graphically registered using a computerized program (Lab View). The test was run until full DIP joint motion and rupture of the tendon repair occurred. The maximum tensile load during flexion to reach an angular rotation of 50 degrees in the DIP joint was registered (MTL50). This value represents the resistance that must be overcome to achieve full physiologic flexion of the DIP joint and can be used to determine the functional hindrance caused by adhesions.

Statistics. The effect of each type of membrane versus the contralateral saline solution regarding adhesion preventive effect and the tensile strength of the tendon repair was evaluated using the Wilcoxon Signed-Rank test.

Results

The animals tolerated the surgical procedure well and the wounds appeared macroscopically free of infection. A total of 40 digits were operated. No ruptures of the tendon repairs were seen.

Both the tested substances showed better mean values of MTL50 compared to the control digits (HYALOBARRIER 20, p=0.879 and HYALOBARRIER 50, p=0.508) (Table 14). The membranes showed both a significant lower tensile strength of the tendon repair compared to the control digits (HYALOBARRIER 20, p=0.0002; HYALOBARRIER 50. p=0.005) (Table 15).

There was a large interanimal variation in the extent of adhesions formed. Restrictive adhesions are defined as MTL $50 \geq 4.5$ N while non-restrictive adhesions are those where MTL<4.5 N. According to this definition, 10 adhesion formers and 10 non-adhesion formers were found among the animals treated. The possible signs of adhesion preventive effect from treatment with membranes were more pronounced in the adhesion forming animals (HYALOBARRIER 20, four observations, P=0.4652; HYALOBARRIER 50, six observations, p=0.1159) (Table 14).

Discussion

The results of the present study showed adhesion preventive effects in adhesion forming animals. It has to be kept in mind though that the number of animals tested were limited and some animals did not form restrictive adhesions in either digit (close to 50%). There was a very significant simultaneous mild impairment of tensile strength of the tendon repair. The tested nonwoven solid diffusable membranes, therefore, seem not to be optimal as adhesion preventing devices.

TABLE 14

Evaluation of Adhesion Formation 15 Days Postop

| Exp. Material | MTL 50 | | MTL 50 4.5N | | MTL 50 > 4.5N | |
|---|---|---|---|---|---|---|
| | Exp | Control | Exp | Control | Exp | Control |
| HYALOBARRIER 20 | 2.6 | 4.6 | 2.0 | 1.3 | 5.0 | 12.3 |
| HYALOBARRIER 50 | 4.1 | 7.7 | 2.5 | 1.5 | 6.4 | 13.9 |

TABLE 15

TENSILE STRENGTH OF TENDON REPAIR 15 DAYS POSTOP

| Exp Material | Exp Digit | Control Digit |
|---|---|---|
| HYALOBARRIER 20 | 11.2 ± 2.6 | 17.9 ± 3.4 |
| HYALOBARRIER 50 | 13.4 ± 2.1 | 22.2 ± 8.3 |

Each of the publications referred to above is hereby incorporated by reference.

What is claimed is:

1. A composite biomaterial comprised of:
a benzyl ester of hyaluronic acid, wherein 80% of the carboxyl groups of hylauronic acid are esterified with a benzyl radical and up to 20% of the carboxyl groups are esterified with the alkyl radical of a C10 to C20 aliphatic alcohol, and
wherein said biomaterial is in the form of a gel, a flat membrane or mesh, a woven or non-woven tissue, or combinations thereof and wherein said biomaterials prevent the surgical adhesion of tissue.

2. The composite material according to claim 1 wherein said alcohol is stearyl or palmitic alcohol.

3. The composite material according to claim 1 which further comprises a non-biodegradable synthetic polymer.

4. The composite material according to claim 3, wherein said synthetic polymer is a member selected from the group consisting of polypropylene, polyethylene, polyester and polytetrafluoroethylene.

5. The biomaterial of claim 1 further comprising a biologically active agent.

6. The biomaterial of claim 5 wherein the biologically active agent is selected from the group consisting of steroidal and non-steroidal antiinflammatories, fibrinolytics, hemostatics, antithrombotics, growth factors, antitumorals, antibacterials, antivirals and antifungals.

7. The composite biomaterial according to claim 1, further comprising an auto-crosslinked derivative hyaluronic acid wherein 0.5 to 20% of the carboxyl groups of hyaluronic acid are cross-linked to the hydroxyl group of the same or different hyaluronic acid molecule.

8. The composite biomaterial according to claim 7, wherein said auto-crosslinked derivative has 4.5 to 5.0% of the carboxyl groups of the hyaluronic acid molecule cross-linked.

9. A method for preventing surgical adhesions of tissue which comprises applying to tissue involved in surgery a biomaterial comprised of:
a benzyl ester of hyaluronic acid wherein 80% of the carboxyl groups of hyaluronic acid are esterified with a benzyl radical and up to 20% of the carboxyl groups are esterified with the alkyl radical of a $C_{10}$ to $C_{20}$ aliphatic alcohol.

10. The method according to claim 9, wherein said alcohol is stearyl or palmitic alcohol.

11. The method according to claim 9 wherein said biomaterial further comprises a non-biodegradable synthetic polymer.

12. The method according to claim 11, wherein said synthetic polymer is a member selected from the group consisting of polypropylene, polyethylene, polyester and polytetrafluoroetheylene.

13. The method of claim 9 wherein said surgery is selected from the group consisting of abdominal, laparoscopic, laparotomic, intestinal, gynecologic, abdominalpelvic, peritoneal, urogenital, orthopedic, spinal/dura mater, tendon/nerve, including carpal tunnel, cardiovascular, thoracic, ophthalmic, oncologic, plastic, esthetic, ENT, paranasal sinuses, and transplantation.

14. The method of claim 9, wherein said biomaterial further comprises an auto-crosslinked derivative hyaluronic acid wherein 0.5 to 20% of the carboxyl groups of hyaluronic acid are crosslinked to the same or different hyaluronic acid molecule.

15. The method according to claim 14, wherein said cross-linked derivative has 4.5 to 5% of the carboxyl groups of the hyaluronic acid molecule cross-linked.

* * * * *

UNITED STATES PATENT AND TRADEMARK OFFICE
CERTIFICATE OF CORRECTION

PATENT NO.         : 6,723,709 B1
APPLICATION NO.    : 09/031835
DATED              : April 20, 2004
INVENTOR(S)        : Daniele Pressato et al.

It is certified that error appears in the above-identified patent and that said Letters Patent is hereby corrected as shown below:

(30) Foreign Application Priority Data Please insert;

August 29, 1995 (IT) .............................PD95A000166
August 29, 1995 (IT) .............................PD95A000167

Signed and Sealed this

Twentieth Day of March, 2007

JON W. DUDAS
*Director of the United States Patent and Trademark Office*